(12) United States Patent
Aljuri et al.

(10) Patent No.: US 11,076,928 B2
(45) Date of Patent: Aug. 3, 2021

(54) SURGICAL DRAPE WITH CANOPY

(71) Applicant: PROCEPT BioRobotics Corporation, Redwood City, CA (US)

(72) Inventors: Nikolai Aljuri, Hillsborough, CA (US); Surag Mantri, East Palo Alto, CA (US); Matt Sprinkel, Redwood City, CA (US); James Badia, Redwood City, CA (US); Nishey Wanchoo, Foster City, CA (US); Mark Baerenrodt, Millbrae, CA (US); Kevin Staid, Lowell, MA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 0 days.

(21) Appl. No.: 16/785,355

(22) Filed: Feb. 7, 2020

(65) Prior Publication Data
US 2020/0170742 A1    Jun. 4, 2020

Related U.S. Application Data

(63) Continuation of application No. PCT/US2018/046254, filed on Aug. 10, 2018.
(Continued)

(51) Int. Cl.
*A61B 46/00* (2016.01)
*A61B 1/31* (2006.01)
(Continued)

(52) U.S. Cl.
CPC .............. *A61B 46/30* (2016.02); *A61B 46/10* (2016.02); *A61B 46/20* (2016.02); *A61B 46/40* (2016.02);
(Continued)

(58) Field of Classification Search
CPC ......... A61B 46/00; A61B 46/10; A61B 46/20; A61B 46/23; A61B 46/30; A61B 46/40;
(Continued)

(56) References Cited

U.S. PATENT DOCUMENTS

| 3,251,360 A | 5/1966 | Melges |
| 4,076,017 A | 2/1978 | Haswell |

(Continued)

FOREIGN PATENT DOCUMENTS

| WO | 2013130895 | 9/2013 |
| WO | 2017161331 | 9/2017 |

OTHER PUBLICATIONS

Microtek Medical, Lingeman Lithotomy Endoscopy Drape (see Additional Comments in Transmittal Letter).
(Continued)

*Primary Examiner* — Keri J Nelson
(74) *Attorney, Agent, or Firm* — FisherBroyles LLP; John Shimmick

(57) ABSTRACT

A surgical drape is configured for covering a patient and an ultrasonography probe during surgical treatment of the patient. The surgical drape may comprise a first portion that comprises a canopy portion. The canopy portion can be sized and shaped to at least partially cover a mechanical arm coupled to the ultrasonography probe and a proximal portion of the ultrasonography probe, and the canopy portion can be configured to move with the proximal portion of the ultrasonography probe when the ultrasonography probe is supported by the mechanical arm. A second portion can be coupled to the first portion, in which the second portion is sized and shaped to cover at least a portion of a torso of the patient.

29 Claims, 35 Drawing Sheets

Related U.S. Application Data

(60) Provisional application No. 62/671,320, filed on May 14, 2018, provisional application No. 62/543,893, filed on Aug. 10, 2017.

(51) Int. Cl.

| | | |
|---|---|---|
| *A61B 46/10* | (2016.01) | |
| *A61B 46/20* | (2016.01) | |
| *A61B 34/00* | (2016.01) | |
| *A61B 46/23* | (2016.01) | |
| *A61B 8/12* | (2006.01) | |

(52) U.S. Cl.
CPC . *A61B 1/31* (2013.01); *A61B 8/12* (2013.01); *A61B 34/74* (2016.02); *A61B 2046/236* (2016.02); *A61B 2217/005* (2013.01)

(58) Field of Classification Search
CPC .. A61B 1/31; A61B 8/12; A61B 34/74; A61B 2046/234; A61B 2046/236; A61B 2217/005
USPC ......................................... 128/849, 852–854
See application file for complete search history.

(56) References Cited

U.S. PATENT DOCUMENTS

| | | | |
|---|---|---|---|
| 4,690,137 A | 9/1987 | Starzmann | |
| 5,305,765 A | 4/1994 | Potts | |
| 5,388,593 A | 2/1995 | Thomalla | |
| 5,445,165 A | 8/1995 | Fenwick | |
| 5,778,889 A | 7/1998 | Jascomb | |
| 6,070,586 A | 6/2000 | Harroll | |
| 6,357,445 B1 | 3/2002 | Shaw | |
| 6,615,836 B1 | 9/2003 | Griesbach | |
| 6,938,639 B1 | 9/2005 | Robinson | |
| 7,727,244 B2 | 6/2010 | Orban, III | |
| 8,286,637 B2 * | 10/2012 | Kaska | A61B 46/10 128/852 |
| 8,739,797 B2 | 6/2014 | Bonutti | |
| 9,867,635 B2 | 1/2018 | Alvarez | |
| 2007/0102005 A1 | 5/2007 | Bonutti | |
| 2007/0175487 A1 | 8/2007 | Eid | |
| 2008/0023013 A1 | 1/2008 | Tuke | |
| 2014/0007886 A1 | 1/2014 | Singh | |
| 2014/0309649 A1 | 10/2014 | Alvarez | |
| 2015/0025539 A1 | 1/2015 | Alvarez | |
| 2015/0047647 A1 | 2/2015 | Winer | |
| 2015/0366544 A1 | 12/2015 | Yap | |
| 2016/0074268 A1 | 3/2016 | Breegi | |
| 2016/0166323 A1 * | 6/2016 | Tylka | A61B 46/10 128/852 |
| 2016/0213439 A1 | 7/2016 | Munson | |
| 2018/0289439 A1 * | 10/2018 | McGahan | A61B 46/00 |

OTHER PUBLICATIONS

Ecolab, Microtek Patient Drapes (see Additional Comments in Transmittal Letter).

International Search Report and Written Opinion for International Application No. PCT/US2018/046254, 18 pages (dated Dec. 12, 2018).

Uromax Surgical Table Specifications (obtained from www.surgicaltables.com; accessed Feb. 3, 2021) (Year: 2016).

Non-Final Office Action for U.S. Appl. No. 16/785,321, 29 pages (dated Jan. 21, 2021).

Non-Final Office Action for U.S. Appl. No. 16/785,377, 23 pages (dated Feb. 8, 2021).

Non-Final Office Action for U.S. Appl. No. 16/850,892, 33 pages (dated Feb. 8, 2021).

Amendment and Response to Non-Final Office Action for U.S. Appl. No. 16/785,321, 8 pages (dated May 20, 2021).

Amendment and Response to Non-Final Office Action for U.S. Appl. No. 16/785,377, 10 pages (dated May 20, 2021).

Amendment and Response to Non-Final Office Action for U.S. Appl. No. 16/850,892, 10 pages (dated May 25, 2021).

Office Action (Non-Final) for U.S. Appl. No. 16/785,321, 29 pages (dated Jun. 4, 2021).

Office Action (Final) for U.S. Appl. No. 16/785,377, 24 pages (dated Jun. 9, 2021).

\* cited by examiner

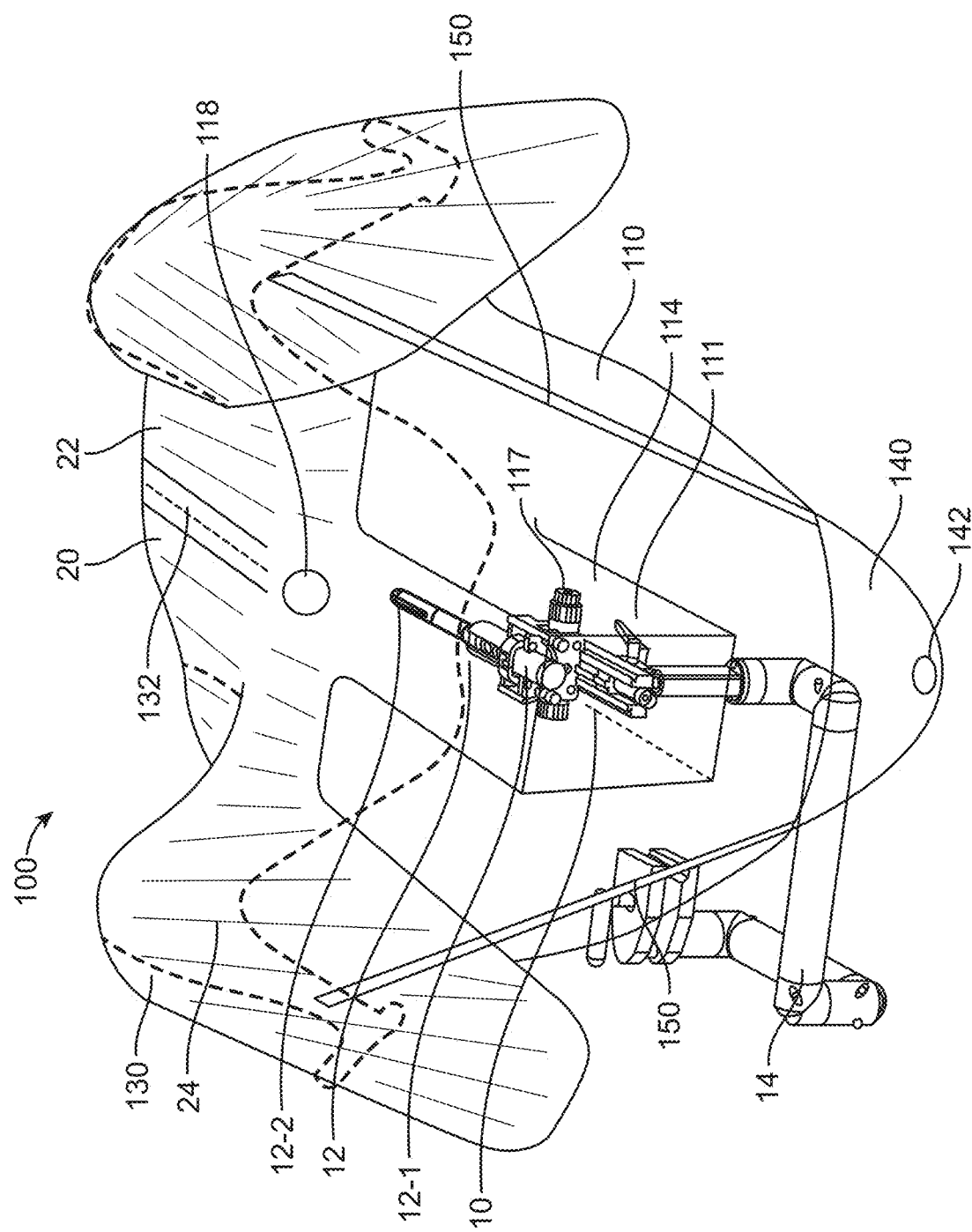

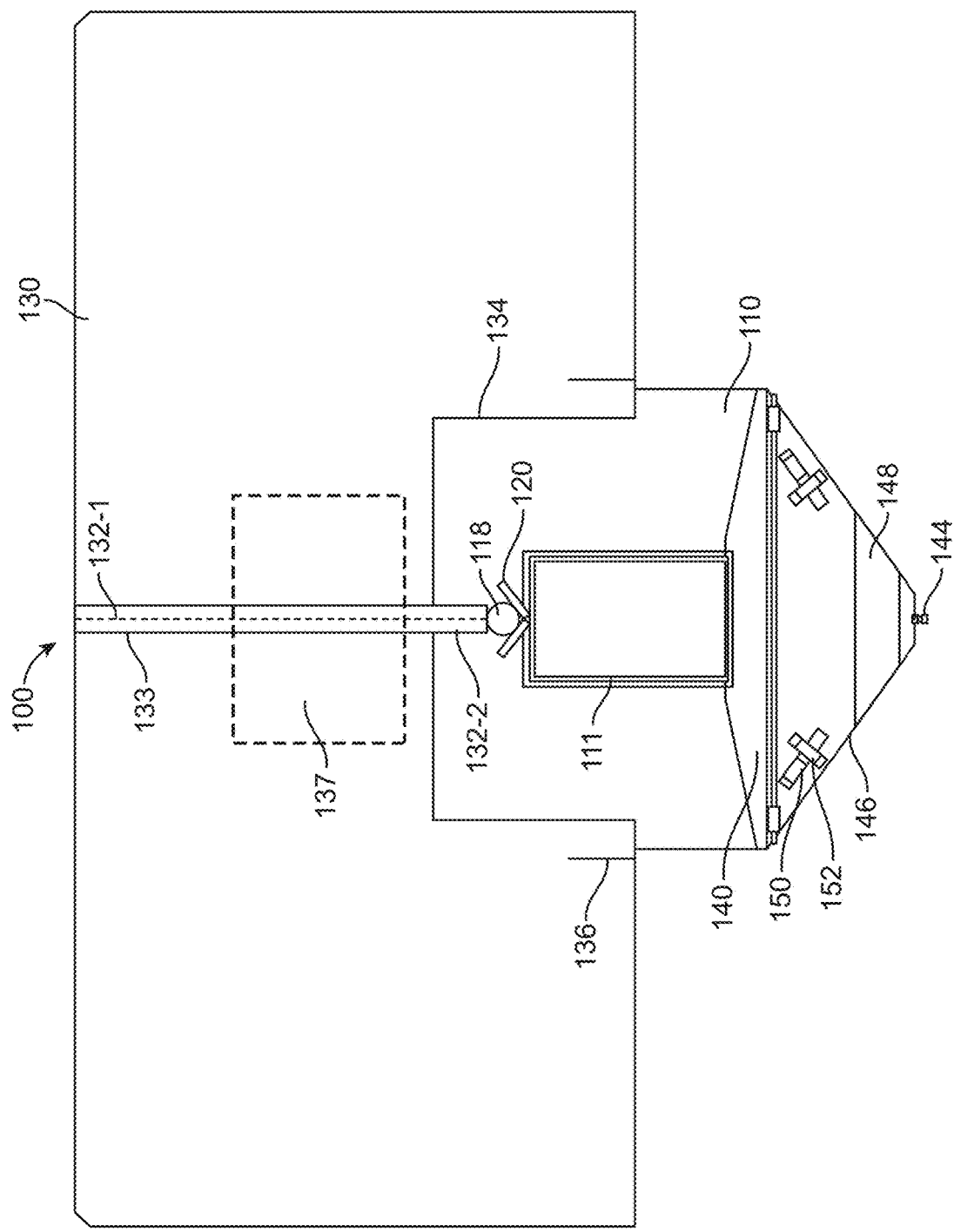

Step D

Step C

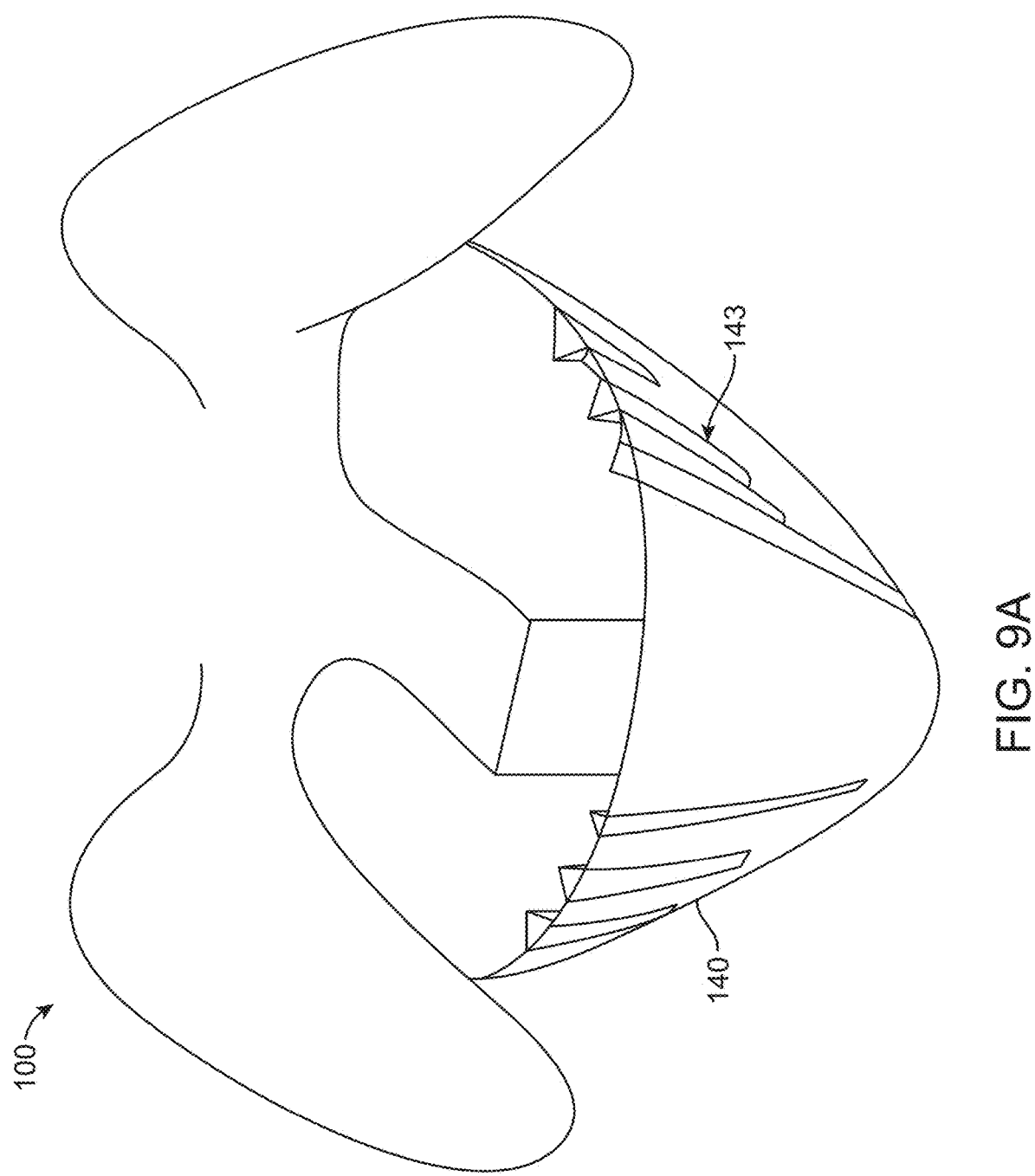

SURGICAL DRAPE WITH CANOPY

RELATED APPLICATIONS

The present application is a continuation of International Application No. PCT/US2018/046254, published as WO/2019/032986 on Feb. 14, 2019, and claims the benefit under 35 U.S.C. § 119(e) of U.S. Provisional Application No. 62/543,893, filed Aug. 10, 2017, and to United States Provisional Application, filed May 14, 2018, the entire disclosures of which are incorporated herein by reference.

BACKGROUND

Surgical systems and devices have been used in urological procedures on male patients. For example, in male urological procedures, a transrectal ultrasonography (TRUS) probe may be inserted into the rectum of the patient in conjunction with insertion of a handpiece into the urethra. During the surgical procedure, it is often necessary to cover or drape both the devices and the patient to protect them from contamination by blood or other bodily fluids. While surgical drapes are commonly used to cover a patient's body, conventional drapes and systems for providing a sterile barrier and for effective fluid management can be less than ideal in at least some respects. For example, conventional drapes for male urological surgical procedures may have a simple, generally flat shape that may not be well suited for use with some surgical systems and transrectal probes, and as such may impede the mobility of the TRUS probe or a mechanical arm coupled to the TRUS probe. Moreover, conventional drapes may be opaque and may not permit visibility of the surgical site while allowing freedom of movement of the TRUS probe. Also, prior surgical drapes can allow greater accumulation of surgical fluids than would be ideal in at least some instances. In some situations, the drape may sag due to the weight of a filled fluid bag attached thereto. Additionally, removal of the drape may be more difficult than would be ideal, for example after the urology procedure with surgical instruments (e.g. catheters) still in place or with a catheter securing or tensioning device placed on the patient.

In light of the above, it would be desirable to provide a drape that allows for improved ease of use with surgical instruments while reducing interference or impedance in the operation and movement of an imaging probe. Moreover, it would be desirable to provide surgical drapes having improved fluid management capability and that serve as a substantially transparent sterile barrier between the urethra and rectum during a urology procedure.

SUMMARY

Some embodiments of the present invention comprise an improved sterile drape system, and methods for draping or covering portions of a surgical system and a patient. The system, apparatus, and methods disclosed herein relate to a drape for protecting the patient and surgical system during urology procedures. Advantageously, some embodiments of the present invention allow a surgical system to be protected by a drape that provides improved visibility and monitoring of instruments inserted into surgical site while reducing interference or impedance in the operation and movement of an imaging probe of the surgical system. The embodiments disclosed herein can be advantageous in providing improved fluid management and provide decreased accumulation of fluids during urological surgical procedures.

A surgical drape may comprise a canopy portion configured for placement over a proximal portion of a transrectal device, in which the canopy portion comprises a canopy sized and shaped to receive the proximal portion of the transrectal device. The canopy portion may comprise a barrier material configured to allow manipulation of the proximal portion of the transrectal device through the canopy portion while maintaining a sterile surgical field above the transrectal device. The canopy portion may comprise a protrusion, such as a rectangular or curved protrusion on an upper sterile side, so as to define an underlying volume on a lower non-sterile side, sized and shaped to receive the proximal portion of the transrectal device. The canopy portion may comprise shaping elements to add stiffness to the canopy and allow the user to at least partially shape the canopy as desired to facilitate use of the canopy.

The surgical drape may comprise a torso portion sized and shaped to cover at least a portion of the torso of the patient. The drape may comprise an opening sized and shaped to allow surgical access to the urethra of the patient, in which the opening is located between the torso portion and the canopy portion and may correspond to a pelvic portion of the patient, although the opening can be located on the torso portion or the canopy portion or a pelvic portion of the drape extending between the canopy portion and the torso portion. The canopy portion can be configured to move with the proximal portion of the transrectal device while the opening remains in a fixed location on the patient.

The surgical drape may comprise a container portion connected to the canopy portion and the torso portion, in which the container portion is configured to collect and release fluids that drain from the canopy portion and optionally the torso portion. The canopy portion may comprise concave inverted portions near the protrusion, in order to direct fluid from the opening and the canopy portion toward the container portion. The container portion may comprise a porous structure upstream of a suction port, in which the porous structure comprises channels sized to inhibit passage of blood clots and tissue from the patient that could clog the suction port, and to pass surgical fluids such as saline and blood plasma to the suction port. The container portion may comprise stiffening elements to maintain the container portion in an open configuration. Each of the torso portion, the canopy portion, and the container portion may comprise flexible sheet material, such that the drape may comprise a compact sterile configuration for storage prior to use and an extended configuration when placed on the patient.

In one aspect, a surgical drape for covering a patient and a transrectal device during a surgical treatment of the patient is provided. In some embodiments, the drape comprises a canopy portion sized and shaped to at least partially cover a proximal portion of the transrectal device, the canopy portion configured to permit the user to manipulate the transrectal device through the canopy portion, and a torso portion coupled to the canopy portion, the torso portion sized and shaped to cover at least a portion of a torso of the patient.

In some embodiments, the canopy portion and the torso portion comprise a sterile barrier material to maintain sterility between a urethra and a rectum of the patient when a sterile urological probe has been inserted into the urethra of the patient and the transrectal probe has been inserted into a rectum of the patient. Optionally, the canopy portion can comprise an optically transmissive sterile barrier material that permits viewing of the proximal portion of the transrectal device through the optically transmissive sterile barrier material. Further, the optically transmissive material can comprise one or more of a transparent material, a translucent material, a semi-transparent material, or a semi-translucent material.

In some embodiments, the torso portion comprises an opaque material and optionally wherein the canopy portion comprises an opaque material. Further, the transrectal device can comprise one or more of a transrectal ultrasonography (TRUS) probe or a colonoscope.

In some embodiments, the first portion of the drape can comprise an opening sized to receive a penis of the patient from a non-sterile side of the surgical drape so as to extend a portion of the penis to a sterile side of the drape and to receive a sterile surgical instrument to be inserted into a urethra of the patient from the sterile side of the drape, and wherein the opening is located in proximity to the canopy portion and optionally wherein the opening is located adjacent to the canopy portion. Additionally, the drape can further comprise a container portion comprising sheet material coupled to the canopy portion to receive surgical fluids, with the container portion comprising a lower end with a suction port to drain fluids from the container and a porous structure upstream of the suction port to inhibit clogging of the suction port. Additionally still, the container portion can comprise stiffeners to maintain the container in an open configuration to receive the surgical fluids and optionally wherein the stiffeners comprise transversely extending stiffeners. Alternatively, the canopy portion can comprise a protruding portion on an upper side of the drape sized and shape to receive the proximal portion of the transrectal device and inverted portions on the upper side of the drape comprising opposite curvature to facilitate drainage toward the container portion.

In some embodiments, the torso portion, the canopy portion of the container portion comprise a material that is impervious to surgical fluids. Further, the surgical instrument can comprise one or more of a surgical probe or a diagnostic probe. Even further, the canopy portion can permit viewing of the transrectal device and maintains sterility of the surgical instrument when the surgical instrument is inserted into the urethra of the patient.

In some embodiments, the canopy portion can be coupled to an opening in a first portion comprising the canopy portion.

In some embodiments, the canopy portion can comprise a three-dimensional space sized and shaped to cover the proximal portion of the transrectal device such that the proximal portion of the transrectal device is permitted to move within the three-dimensional space and optionally wherein the transrectal device is configured to move within the three-dimensional space in a non-restrictive manner. Alternatively, the three-dimensional space defines a volume within a range from about 750 cm$^3$ to about 70,000 cm$^3$. Alternatively still, the three-dimensional space can comprise a substantially rectangular shape, a curved shape, or can be sized and shaped to cover proximal portions of a plurality of transrectal devices of different sizes and shapes. Even alternatively still, the canopy portion can comprise a volume that is greater than a volume occupied by the proximal portion of the transrectal device.

In some embodiments, the canopy portion can comprise a material having a thickness ranging from about 0.25 mm to about 3 mm. Alternatively, the material can be substantially flexible, or the material can be substantially rigid or non-compliant, or the material can comprise one or more of polyethylene, polypropylene, or a translucent polymeric film.

In some embodiments, the canopy portion can comprise a full volume in a fully extended configuration and is configured to collapse to less than the full volume in a free-standing configuration and optionally wherein the free-standing configuration corresponds to the canopy portion being supported along a lower perimeter and being allowed to collapse at least partially under its own weight and optionally wherein the full volume of the canopy portion corresponds to a volume of the canopy portion when filled with a fluid and supported around the perimeter of the canopy portion.

In some embodiments, the canopy portion can be configured to collapse to less than its full volume when the canopy portion is covering the proximal portion of the transrectal device.

In some embodiments, a second portion comprises the torso portion comprises a weakened material extending along a midline of the second portion to assist removal of the surgical drape by allowing the second portion to separate along the weakened material and optionally wherein the weakened material comprises one or more of perforations, thinned material relative to adjacent unweakened material, thermally or chemically weakened material or stressed material along the midline.

In some embodiments, a second weakened material extends in a second direction transverse to the midline in order to facilitate removal of the surgical drape around a base of a traction device coupled to the patient with a catheter extending along a urethra of the patient and optionally wherein the second weakened material comprises perforations extending in the second direction.

In some embodiments, the second portion comprises perforations extending along a midline of the second portion to assist removal of the surgical drape. Alternatively, the second portion can further comprise a material disposed on top and/or below the perforations, wherein said material is impervious to fluids. Alternatively still, said material can comprise a tape covering the perforations from below and/or above the perforations. Even further, the tape can comprise a first tape layer on top of the perforations and a second tape layer below the perforations such that the perforations are sandwiched between the first and second tape layers and optionally wherein the perforations allow insertion or access of a catheter to be inserted into a urethra of the patient and optionally wherein the catheter comprises a suprapubic catheter to drain urine from a bladder of the patient. Alternatively, a sliding mechanism can be configured to slide along the perforation to open the perforations and optionally wherein the sliding mechanism comprises a sliding dove-tail mechanism that releasably opens and closes the perforation and optionally wherein the sliding dove-tail mechanism comprises a zipper.

In some embodiments, a container can be coupled to the torso portion and the canopy portion to receive fluid from the canopy portion. Alternatively, the canopy portion can comprise an inverted portion to direct surgical fluids toward the container and optionally wherein the inverted portion comprises a concave upper surface to direct surgical fluids toward the container. Alternatively, the canopy portion can be designed such that fluid flows downward toward the container when the canopy portion is in an inverted configuration. In a further alternative, the inverted configuration can prevent the fluid from accumulating or pooling on the canopy portion. In a further alternative, the inverted configuration can comprise one or more sloping surfaces that aid the fluid to flow downward toward the container.

In some embodiments, a container can have an opening and configured to receive and store waste including bodily fluids, surgical-related fluids, tissue or debris generated during the surgical treatment. Alternatively, the container can comprise a material impervious to surgical fluids and is configured to provide a storage volume within a range from about 1 cm$^3$ to about 70,000 cm$^3$ and optionally within a range from about 1000 cm$^3$ to about 10,000 cm$^3$. Alternatively, the container can comprise a surgical suction port and a porous structure to inhibit clogging of the suction port of the container, the porous structure comprising as one or more of a tube with holes on an outer wall, a screen, a mesh, a fabric, a grating, a plurality of apertures formed in a sheet of material, an open cell foam, a sponge a screen, a perforated tubing matrix, fabric, a sintered material, or particles held together to define channels. Alternatively, the container can comprise an attachment configured to releasably attach the container to an upper part of the second portion to support the container holding the waste. Alternatively still, the attachment can comprise tethers coupled to the upper part of the second portion from two sides of the opening of the container. Alternatively, the container can comprise a connector at a bottom of the container configured to connect to a suction system. Alternatively, the container can comprise a screen attached to a lower inner side of the container, wherein the waste is passed through the screen, and wherein the screen is configured to collect the tissue. Alternatively, the container can comprise a third sheet of material that is separable from a first sheet of material forming the canopy portion and a second sheet forming the torso portion. Alternatively, the container and the canopy portion can be formed from the same sheet of material.

In some embodiments, the canopy portion and the torso portion can be detachably coupled to each other.

In some embodiments, a first portion can comprise the canopy portion comprises a sheet of material comprising joined edges.

In some embodiments, the canopy portion can be integrally formed with the torso portion from a single piece of material.

In some embodiments, the canopy portion can comprise a separate sheet of material that is attachable to the torso portion.

In some embodiments, the canopy portion and the torso portion can be formed together as one piece.

In some embodiments, the canopy portion and the torso portion can be joined together as one piece.

In some embodiments, the canopy portion can be coupled to a cut-out formed in the torso portion.

In some embodiments, one or more of the torso portion, the canopy portion or a container portion can comprise thermoformed material shaped with a mold to define a shape of the one or more of the torso portion, the canopy portion or the container portion. Alternatively, the canopy portion and the torso portion can be formed from a single sheet of thermoformed material and optionally wherein the canopy portion has been thermoformed on a mold to shape the canopy portion to receive the transrectal device and optionally wherein the canopy portion comprises a convex outer surface to deflect fluid away from the canopy portion and a concave inner surface to receive the proximal portion of the transrectal device and optionally wherein the canopy portion comprise a substantially uniform thickness extending between the concave surface and the convex surface and optionally wherein the substantially uniform thickness varies by no more than 25%.

In some embodiments, the canopy portion can be configured to allow manipulation of the transrectal device through the canopy portion and optionally wherein the canopy portion is configured to permit the user to control the movement of the transrectal device through the canopy portion. Alternatively, the canopy portion can be configured to permit the user to move the transrectal device by holding and moving the proximal portion of the transrectal device through the canopy portion with the canopy portion disposed between a hand of the user and the transrectal device and wherein the canopy portion is configured to move with the proximal portion. Alternatively still, the canopy portion can be disposed between the proximal portion of the transrectal device and the hand of the user is configured to move from a first position to a second position when the proximal portion of the transrectal device moves from a first position to a second position and wherein the canopy portion is configured to return at least partially from the second position toward the first position when the hand of the user releases the proximal portion and optionally wherein the canopy portion comprises a volume greater than a volume of the proximal portion of the transrectal device in order to allow the proximal portion to return from the second position toward the first position and optionally wherein a distance of return from the second position toward the first position comprises a distance within a range from about 1 mm to about 25 mm. Optionally, a return of the canopy portion toward the first position can allow the user to hold the proximal portion of the transrectal device and move the proximal portion of the transrectal device from the second position to a third position and optionally wherein the proximal portion of the transrectal device comprises a knob and each of the first position, the second position and the third position correspond to rotational orientations of the knob.

In some embodiments, the canopy portion can be sized and shaped to at least partially cover a surgical arm coupled to the transrectal device.

In some embodiments, the canopy portion can be configured to cover at least a surgical arm coupled to the transrectal device and the proximal portion of the transrectal device such that the canopy portion collectively moves with the surgical arm and the proximal portion of the transrectal device. Alternatively, the canopy portion can be configured to permit the user to manipulate the surgical arm that supports the transrectal device through the canopy portion. Alternatively still, the proximal portion of the transrectal device can be mounted on the surgical arm and the canopy portion is configured to cover at least a portion of the surgical arm and the proximal portion of the transrectal device when the distal portion of the transrectal device has been inserted into the patient. In an alternatively embodiment an apparatus comprising the surgical drape, the transrectal device, and the surgical arm as detailed in the alternative embodiment can be provided.

In some embodiments, the surgical drape can comprise a volume within a range from about 100 cm$^3$ to about 4,000 cm$^3$ in a compact configuration when stored in a compact configuration within a sterile storage container and wherein the canopy portion comprises a volume within a range from about 750 cm$^3$ to about 70,000 cm$^3$ when the surgical drape comprises an expanded deployed configuration. Alternatively, the container portion can comprise a volume within a range from about 1000 cm$^3$ to about 40,000 cm$^3$ in the expanded deployed configuration and optionally wherein the volume is within a range from about 1000 cm$^3$ to about 40,000 cm$^3$.

In some embodiments, at least one of a first portion can comprise the canopy portion or a second portion comprising the torso portion is operably coupled to an actuation element configured to deploy one or more sections of the surgical drape from a compact configuration to an extended configuration. Alternatively, the actuation element comprises one or more spring elements and wherein the one or more spring elements can comprise spring steel. In one alternative, the surgical drape can comprise the actuation element. In one alternative, the one or more sections of the surgical drape can comprise the canopy portion. In one alternative, the compact configuration can comprise a substantially two-dimensional shape, and the extended configuration comprises a substantially three-dimensional shape. In one alternative, the surgical drape can be in the compact configuration when the surgical drape is not in use prior to deployment, and deployed to the extended configuration prior to or during use of said surgical drape for the surgical treatment of the patient.

In some embodiments, the first portion of the surgical drape can comprise an opening with an adjustable closure to cinch around an external organ of the patient comprising a urethra for maintaining integrity of a sterile field or environment and optionally wherein the organ comprises a penis of the patient. In one alternative, the adjustable closure can comprise a zipper.

In some embodiments, the first portion of the surgical drape can comprise an opening with an adhesive material to gather and wrap loose sections of the drape around an organ of the patient for maintaining integrity of a sterile surgical field or environment.

In some embodiments, a first portion of the surgical drape can comprise material for covering a torso or legs of the patient. In one alternative, the material is configured to hang freely. In one alternative, the material is wrapped around the torso or underside of the legs of the patient or stirrups. In one alternative, the material is secured using straps, tethers, Velcro™, and/or tape. In one alternative, the material can comprise an adhesive for attaching the material around the stirrups to form a holder in which a container for receiving and storing waste can be secured and suspended.

In some embodiments, a portion of the drape can be mounted to a support structure that is attached to an operating table over or near the patient. In one alternative, the portion of the drape is mounted to the support structure using straps, tethers, Velcro™, and/or tape. In one alternative, the support structure can be attached to the operating table using straps, tethers, Velcro™, and/or tape. In one alternative, the support structure can be configured to couple to or comprises a graphical display. In one alternative, the second portion of the drape can comprise a transparent material that permits the graphical display to be viewed through the drape. In one alternative, the second portion can comprise a transparent window comprising said transparent material, that permits viewing of the graphical display through the surgical drape. In one alternative, the graphical display comprises a touchscreen. In one alternative, the transparent material can be compatible for use with the touchscreen such that a user is able to interact with the touchscreen with the transparent material as an intervening layer. In one alternative, the transparent material is flexible or loose-fitting so as to allow a user to manually manipulate one or more input/output (I/O) devices that are connected to the graphical display. In one alternative, the one or more I/O devices can comprise one or more of a joystick, mouse, trackball, trackpad, or 3-dimension cursor.

In some embodiments, the container can comprise a substantially conical funnel shape to allow fluids to drain to an exit port.

In some embodiments, the container can comprise a substantially rectangular funnel shape to allow fluids to drain to an exit port.

In some embodiments, the container can comprise structures for supporting one or more configurations of the container. In one alternative, the structures can comprise inclined pleats, substantially vertical pleats or substantially horizontal pleats. In one alternative, the inclined or vertical pleats serve as stiffeners that prevent the container from collapsing and changing its shape/form under load. In one alternative, the vertical pleats can be configured to allow air flow to vent displaced fluid as the fluid is being extracted or drained from the container. In one alternative, the substantially horizontal pleats can comprise curved pleats configured to permit the container to collapse into a collapsed configuration in a telescoping manner. In one alternative, the container is collapsible to a substantially planar configuration, and extendable to a substantially 3-dimensional configuration with aid of the substantially horizontal pleats.

In some embodiments, the container comprises a flexible, semi-rigid, or rigid material.

In some embodiments, the container can be configured to serve as a packaging enclosure for storing the surgical drape or portion thereof. In one alternative, the packaging enclosure is used to store the surgical drape or portion thereof when the surgical drape can be in its original state prior to use. In one alternative, the packaging enclosure can be to store the surgical drape or portion thereof for subsequent disposal after the surgical drape has been used.

In some embodiments, the container can be attachable to a user's gown using attachment means comprising of mechanical couplings or adhesive tape.

In some embodiments, the container can be coupled to a halter structure that is configured to be worn on or around a neck of a user.

In some embodiments, the container can comprise one or more compliant stiffening elements for maintaining structural form of the container.

In some embodiments, at least one of the first portion or the second portion can comprise one or more frame structures that support a configuration of at least the first portion or the second portion.

In some embodiments, the container can comprise an integral perforated tubing matrix to maintain fluid flow and air displacement and optionally wherein the perforated tubing matrix comprises stiffness to maintain the container in an expanded profile configuration. In one alternative, the perforated tubing matrix is connected to a drain/suction port. In one alternative, the perforated tubing matrix comprises one or more fluidic channels. In one alternative, the one or more fluidic channels extends for a length of about 5 cm to about 40 cm along a plurality of surfaces of the drape under a filter screen.

In some embodiments, the container can be designed to ensure sufficient suction of fluid from the container by (1) providing non block-able passageways for the suction to act on the fluid, or (2) by providing a mechanism that prevents material from folding over a vacuum port and blocking the vacuum port.

In some embodiments, the container can comprise rolled up tube-like areas formed from rolled up drape material, wherein said rolled up tube-like areas are connected to a drain/suction port to maintain fluid flow and air displacement.

In some embodiments, the container can comprise a deployable flap that is positioned to prevent fluid splash onto a user. In one alternative, the deployable flap can comprise a non-sterile portion that extends outside of the surgical drape. In one alternative, the deployable flap can comprise a self-supporting semi-cylindrical shape or form. In one alternative, the deployable flap can comprise stiffening structures that are adjustable in position.

In some embodiments, the container can comprise one or more ports for accepting fluid from an irrigation or aspiration pump, or from a drain line above or below a screen.

In some embodiments, the one or more ports can comprise an opening, an aperture, a fenestration, a connecting feature, or a sealing flange.

In some embodiments, the container can comprise one or more extruded portions extending from the container. In one alternative, the one or more extruded portions can comprise an inner sterile surface and an external non-sterile surface. In one alternative, the external non-sterile surfaces provide a working space for placement of a support structure comprising the surgical arm. In one alternative, the external non-sterile surfaces allow ungloved hand(s) to access a sterile space defined within the inner sterile surfaces for manipulation of the transrectal device.

In some embodiments, the container can comprise a screen. In one alternative, the screen can be coupled to an inner lower portion of the container. In one alternative, the screen can be detachable for collecting and transporting tissue or solid samples for analysis or disposal. In one alternative, the screen can comprise a material that is impervious to fluids. In one alternative, the material can be provided along edges or sides of the screen. In one alternative, the screen can comprise a closure element for securing samples for storage or transport. In one alternative, the closure element can comprise a zipper, a zip-lock, an adhesive seal, a draw-string, a clip, or an elastic or conformable wire. In one alternative, the screen can comprise a transparent region that is compatible with imaging modalities for tissue analysis. In one alternative, the screen can be removable from the container along the edges or sides to permit visualization through the transparent region. In one alternative, the screen can comprise an area for displaying information about the patient. In one alternative, the area can be configured to receive thereon a preprinted label containing the information about the patient. In one alternative, the area can be configured to permit a user to write thereon. In one alternative, the area can comprise a plurality of sub-areas for displaying preprinted information or clinician notes. In one alternative, the screen can be configured to fold with collapse of the container. In one alternative, the folding of the screen can be configured to permit airflow to a drain/suction port. In one alternative, the screen can be configured to fold in an interleaved manner. In one alternative, the screen can comprise a hole that is sized or shaped to permit capture of clots, or intact tissue.

In some embodiments, the drape can comprise one or more labels. In one alternative, the one or more labels can comprise instructions for using the drape, and information on one or more of the following: location of one or more access port holes, location of one or more perforations, location of one or more attachment points, areas at which sections of the drape can be detached, placement of the drape onto the patient, location of the drape relative to an operating table, attachment of the drape to the operating table, location of the drape relative to one or more support structures proximal to the operating table, or attachment of the drape to the one or more support structures.

In some embodiments, the drape can comprise excess material in at least the first portion or the second portion to permit a non-sterile hand of the user from a non-sterile working space outside of the drape to access and manipulate the transrectal device or a surgical arm without contaminating a sterile field underneath the drape.

In some embodiments, a method of using the surgical drape can be provided that can comprise providing a first portion comprising the canopy portion, covering at least partially a surgical arm coupled to the transrectal device and the proximal portion of the transrectal device such that the canopy portion is capable of moving with the proximal portion of the transrectal device when the transrectal device is supported by the surgical arm, and coupling the second portion to the first portion such that the second portion covers at least the portion of the torso of the patient.

In some embodiments, a surgical drape for covering a patient and an transrectal device during surgical treatment of the patient is provided with a first portion that permits visual viewing of the transrectal device during the surgical treatment of the patient, and a second portion coupled to the first portion, said second portion being sized and shaped to cover at least a portion of a torso of the patient, wherein the second portion comprises a perforation extending along a midline of the second portion to assist in removal of the surgical drape from the patient. In one alternative, the first portion can comprise a canopy portion, wherein the canopy portion is sized and shaped to at least partially cover a surgical arm coupled to the transrectal device and a proximal portion of the transrectal device, and the canopy portion is configured to move with the proximal portion of the transrectal device when the transrectal device is supported by the surgical arm. In one alternative, the first portion of the drape can comprise an opening sized to receive a surgical probe to be inserted into a urethra of the patient, and wherein the opening is located adjacent to the canopy portion. In one alternative, the first portion permits viewing of the transrectal device through the first portion and maintains sterility of the surgical probe when the surgical probe is inserted into the urethra of the patient. In one alternative, the perforation of the second portion extends to the opening. In one alternative, the canopy portion can comprise a three-dimensional space sized and shaped to cover a proximal portion of the transrectal device such that the transrectal device is permitted to move in a non-restrictive manner within the three-dimensional space. In one alternative, the canopy portion can comprise a volume that is greater than a volume occupied by the proximal portion of the transrectal device. In one alternative, the volume of the canopy portion can be at least two times greater than the volume occupied by the proximal portion of the transrectal device. In one alternative, the canopy portion can comprise a thin flexible material having a thickness ranging from about 0.25 mm to about 3 mm. In one alternative, the canopy portion can be configured to collapse to less than its full volume in a free-standing configuration. In one alternative, the canopy portion can be configured to collapse to less than its full volume when the canopy portion can be covering the proximal portion of the transrectal device. In one alternative, the three-dimensional space can define a volume within a range from about 750 $cm^3$ to about 70,000 $cm^3$. In one alternative, the three-dimensional space can comprise a substantially rectangular shape. In one alternative, the three-dimensional space can be sized and shaped to cover proximal portions of a plurality of transrectal devices of different sizes and shapes. In one alternative, the canopy portion can be configured to wrap around at least the surgical arm coupled to the transrectal device or the proximal portion of the transrectal device such that the canopy portion collectively moves with the surgical arm and the proximal portion of the transrectal device. In one alternative, the first portion and the second portion can be detachably coupled to each other. In one alternative, the first portion and the second portion can be formed together as one piece. In one alternative, the first portion and the second portion can be stitched together as one piece. In one alternative, the first portion can be coupled to a cut-out formed in the second portion. In one alternative, a container having an opening and configured to receive and store waste generated during the surgical treatment can be provided. In one alternative, the container can comprise an attachment configured to releasably attach the container to an upper part of the second portion to support the container holding the waste. In one alternative, the attachment can comprise tethers coupled to the upper part of the second portion from two sides of the opening of the container. In one alternative, the container can comprise a connector at the bottom of the container configured to connect to a suction system. In one alternative, the container can comprise a screen attached to a lower inner side of the container, wherein the waste is passed through the screen, and wherein the screen is configured to collect the tissue. In one alternative, the container portion can comprise a third sheet of material that is separable from a second sheet of material forming the canopy portion. In one alternative, the second sheet of material can be impervious to liquids. In one alternative, the container and the canopy portion can be formed from a same sheet of material. In one alternative, the second portion can comprise a first sheet of material that is impervious to liquids.

In some embodiments, an apparatus that comprises a surgical drape and a transrectal device.

In some embodiments, a method of using the surgical drape can be provided that comprises providing the first portion to permit visual viewing of the transrectal device during the surgical treatment of the patient, coupling the second portion to the first portion such that the second portion covers at least a portion of a torso of the patient, and using the perforation extending along the midline of the second portion to assist in removal of the surgical drape from the patient during or after the surgical treatment.

In some embodiments, a surgical drape for covering a patient and a transrectal device during surgical treatment of the patient is provided. The drape can comprise a first portion that permits visual viewing of the transrectal device inserted into the patient, and a container portion coupled to the first portion to receive and store waste generated during the surgical treatment, wherein the container portion comprises an attachment to releasably attach the container to an upper part of the surgical drape to support the container holding the waste. In one alternative, the attachment can comprise tethers coupled to the upper part of a second portion of the surgical drape from two sides of an opening of the container. In one alternative, wherein the tethers can be coupled to an operation table, a bed rail, a surgical arm, or to a physician. In one alternative, the attachment can comprise a U-ring device configured to be attached to one side of an operation table. In one alternative, the second portion can comprise a second sheet of material that is opaque. In one alternative, the second portion can comprise a second sheet of material that is translucent. In one alternative, the second portion can be sized and shaped to cover at least a portion of a torso of the patient. In one alternative, the tethers can comprise adhesive tabs and straps such that the straps are wrapped around a torso or legs of the patient and secured by the adhesive tabs. In one alternative, the tethers can be wrapped over an exterior surface of the second portion that covers the torso or legs of the patient. In one alternative, the container can comprise a drainage hole for draining the waste. In one alternative, the container can comprise a connector at the bottom of the container configured to connect to a suction system. In one alternative, the connector can comprise an exit port with a sealing flange. In one alternative, the container can comprise a screen attached to a lower inner side of the container, wherein the waste is passed through the screen and wherein the screen is configured to collect the tissue. In one alternative, the container can comprise a third sheet of material that is separable from a first sheet of material forming the first portion. In one alternative, the third sheet of material can be impervious to liquids. In one alternative, the third sheet of material can comprise a translucent material. In one alternative, the first sheet of material can be impervious to liquids. In one alternative, the container can be detachably coupled to the first portion. In one alternative, the container can be below a canopy portion of the first portion. In one alternative, the first portion can comprise a translucent material, wherein the container and the first portion are formed from the same sheet of material.

In some embodiments, a method of using the surgical drape is provided that can comprise providing the first portion to permit visual viewing of the transrectal device during the surgical treatment of the patient, attaching a container portion of the surgical drape to an upper part of the surgical drape to support the container holding the waste, and receiving and storing the waste by the container portion.

In some embodiments, a method or surgical drape can be provided that can comprise a second portion of the surgical drape configured to cover one or more of a foot or a leg of the patient.

In some embodiments, a second portion of the drape comprises a perforation extending along, or at any angle or offset to, a midline of the second portion to assist in removal of the surgical drape from the patient.

In some embodiments, the surgical drape is configured to cover one or more of the feet or legs of the patient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A and 1B show a perspective view of a patient and a surgical system partially covered by a sterile drape in accordance with some embodiments of the invention;

FIG. 3A provides a planar view of the drape on the top side away from the patient.

FIG. 9A illustrates a container with vertical stiffening pleats for maintaining a structural form of the container, in accordance with some embodiments;

DETAILED DESCRIPTION

Figure 1B:
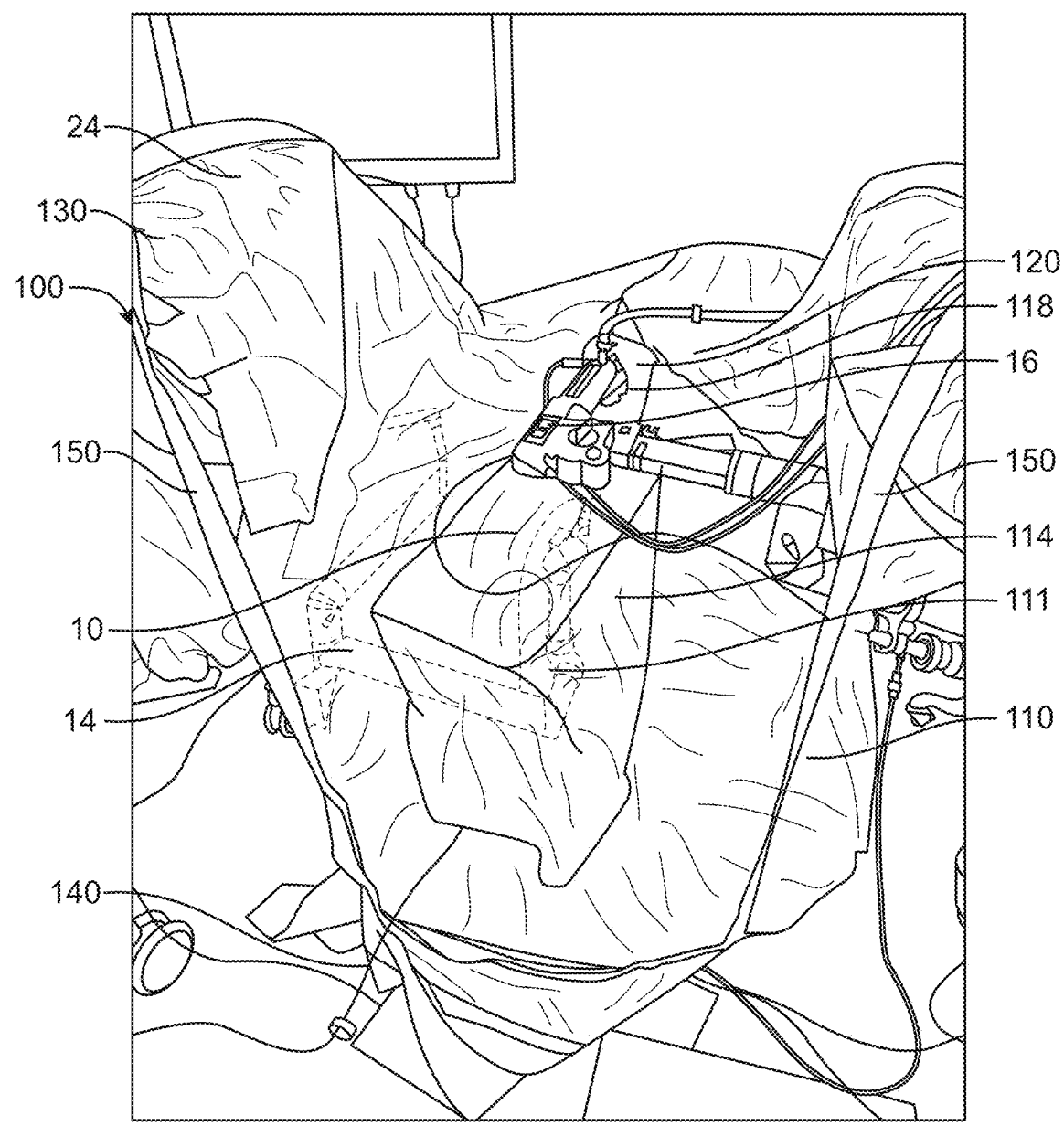

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The methods and apparatus of the present disclosure are well suited for combination with many types of surgical instruments and robotic surgery devices, for example as described in PCT Application No. PCT/US2013/028441, filed on Feb. 28, 2013, entitled "AUTOMATED IMAGE-GUIDED TISSUE RESECTION AND TREATMENT", the entire disclosure of which are incorporated herein by reference, and suitable for combination in accordance with embodiments disclosed herein.

As used herein, the terms proximal and distal in the context of the apparatus refer to proximal and distal as referenced from the apparatus outside the patient, such that proximal may refer to components outside the patient or nearer the operator and distal may refer to components inside the patient or further from the operator.

As used herein, the terms proximal and distal in the context of anatomical locations are with respect to the operator of the apparatus, such that proximal may refer to anatomical locations nearer the operator and distal may refer to anatomical locations further from the operator.

As used herein, the terms distal and proximal refer to locations referenced from the apparatus and can be opposite of anatomical references. For example, a distal location of a probe may correspond to a proximal location of an elongate member of the patient, such as a penis of the patient, and a proximal location of the probe may correspond to a distal location of the elongate member of the patient.

Although specific reference is made to treatment of the prostate, the methods and systems disclosed herein can be used with many tissues. For example, the embodiments disclosed herein may be used in any urological, gynecological or proctological procedures. Embodiments as disclosed herein may be used in any surgical procedures to treat any tissue cavity comprising a proximal opening and a distal opening, the proximal and distal openings allowing the tissue volume to fluidly communicate with other organs or parts of the body adjacent the tissue volume. For example, although specific reference is made to the advancement of a hemostasis device through the urethra into the prostate, and through the bladder neck into the bladder, the hemostasis device as described herein may be advanced through any proximal opening of a tissue cavity into the cavity, and through any distal opening of the tissue cavity into another organ or body part adjacent the tissue volume.

The surgical systems that are protected by the drape may relate to the administration of a hemostatic material or sealant to fill in whole, or in part, any bleeding closed tissue volume. Such tissue volumes may comprise tissue spaces or voids occurring naturally, for example an aneurysm, fissure, or postpartum hemorrhage of the uterus. Such tissue volumes may for example be formed as a result of tissue removal of unnecessary or undesirable growths, fluids, cells, or tissues. The surgical systems as utilized in the surgical procedures are well-suited for treating closed tissue volumes remaining after tumor resection, endometrial ablation, polyp removal, cyst removal, and the like.

The surgical systems involved in the surgical procedures may be well-suited for treating many types of closed tissue volumes such as within rectum, prostate, uterus, cervix, liver, kidney, bowel, pancreas, muscle, and the like.

The surgical system or at least part of the surgical system can be sterilized by normal methods that are compatible with the device, such as steam, heat and pressure, chemicals and the like.

FIGS. 1A and 1B show a perspective view of a patient 20 and a surgical system 10 partially covered by a sterile drape 100 in accordance with some embodiments. The surgical drape 100 may be substantially flexible and may be impervious to liquids, such as bodily fluids. The surgical drape 100 may comprise a first portion 110 coupled to a second portion 130. The second portion may comprise a non-transparent or opaque portion and the first portion may comprise an optically transmissive material, such as one or more of a visually translucent material, a visually translucent material, or semi-transparent material, whereby at least a portion of light is permitted to pass through the material to allow at least partial visualization through the material. For example, a transparent material or a translucent material may allow most of the light in the visible spectrum to pass through and allow at least partial visualization through the material. A semi-transparent material or semi-translucent material may allow only a portion of the visible light or certain wavelengths of light to pass through, thereby resulting in visibility being reduced to some extent. The first portion 110 may be at least partially transparent to the visible light spectrum, such that a user can see through the portion to view an underlying object.

As shown in FIGS. 1A and 1B, the surgical drape 100 may be sized and shaped to cover at least a portion of a surgical system 10. The surgical system 10 may comprise an imaging probe 12 for imaging tissue in a patient's body. The imaging probe 12 may comprise, for example an ultrasonography probe. The imaging probe may comprise a transrectal ultrasound (TRUS) or other imaging modalities for providing real time image guidance to a physician during a surgical procedure. The imaging probe 12 may be coupled to an articulating or mechanical arm 14 configured to support and/or actuate the imaging probe. For example, the imaging probe may be operably coupled to a distal portion of the mechanical arm, and a proximal portion may be coupled to an operation table or stand. The mechanical arm may be configured to provide one or more degrees of freedom of motion to the imaging probe. For example, the mechanical arm can be used to move the imaging probe along a longitudinal axis towards a target tissue of the patient.

The surgical drape 100 may comprise a first portion 110 comprising a canopy portion 111. Part or all of the first portion 110 may comprise a visually transparent or translucent material. In some cases, part of the first portion 110 may be visually transparent or translucent, while another part of the first portion may be opaque. The canopy portion 111 may preferably comprise a visually transparent or translucent material. The canopy portion 111 can be provided or disposed anywhere on the first portion 110, for example at the center, edge, corner, top, bottom, and/or side of the first portion. The canopy portion 111 can be integrally formed with the first portion 110 or as part of the first portion. Alternatively, the canopy portion 111 may be provided as a separate piece from the first portion 110 such that the canopy portion can be fixedly or detachably coupled to the first portion. In some cases, the first portion 110 may comprise a cut-out or opening configured to couple to the canopy portion 111. For example, the cut-out or opening of the first portion may be sized and shaped to match the canopy portion 111, as described elsewhere herein.

The canopy portion 111 may be sized and shaped to substantially cover a proximal end of the imaging probe 10. In some embodiments, the canopy portion 111 may comprise a three-dimensional configuration that provides a working space for the imaging probe 12 to move in an un-restricted manner therein, for example with less physical impedance or interference. The imaging probe can be an ultrasonography probe having a proximal portion 12-1 that is supported by the articulating or mechanical arm 14. The first portion 110 or the canopy portion 111 may be configured to at least partially cover the mechanical arm coupled to the ultrasonography probe and/or the proximal portion of the ultrasonography probe. The surgical drape 100 may also comprise a second portion 130 coupled to the first portion 110. The first portion 110 and the second portion 130 may be fixedly or detachably coupled to each other. The second portion 130 may be sized and shaped to cover at least a portion of a torso 22 of the patient. As previously described, the second portion 130 may be a non-transparent or opaque portion, although the invention is not limited thereto. In some cases, one or more parts of the second portion 130 can be visually transparent or translucent.

The surgical drape may cover at least a portion of an articulating or mechanical arm 14 of the imaging probe. In some cases, the entire imaging probe including the articulating arm and a base from which the arm extends may be covered by the surgical drape. In some situations, the entire imaging probe may be covered by the drape to create a sterile barrier to physically separate the imaging probe from the operation area of the patient.

As mentioned previously, the surgical drape may be compatible with surgical systems utilized in male urology surgical procedures or prostate surgery. In some embodiments, the surgical system may comprise a treatment probe 16 (e.g. shown in FIG. 1B) and an imaging probe. The patient may be placed on a patient support (e.g., examination table or operation table), such that the treatment probe and the imaging probe (e.g. ultrasound probe) can be inserted into the patient. The patient can be placed in one or more of many positions such as prone, supine, upright, or inclined, for example. In some embodiments, the patient may be placed in a lithotomy position, and stirrups may be used, for example. The treatment probe and the imaging probe can be inserted into the patient in one or more of many ways. In some embodiments, the imaging probe may be inserted into the rectum of the patient and the treatment probe may be inserted into the urethra of the patient, and the drape disclosed herein may provide a transparent sterile barrier between the urethra and rectum. In some situations, the imaging probe is not sterilized, and a sterile barrier may be provided to physically separate the imaging probe from the operation area of the patient.

In some cases, insertion of the treatment probe (e.g., sealant delivery device, tissue resection device) and/or delivery of sealant to a cavity or the tissue may be guided by the imaging probe. The imaging probe may be an ultrasonography probe. The imaging probe can comprise a transrectal ultrasound (TRUS) or other imaging modalities for providing visual guidance. TRUS may be used to guide actuation of the catheter during sealant delivery, for example by retracting or advancing the catheter within the cavity by mechanical or manual means.

In some embodiments, the treatment probe may comprise a handpiece. In some cases, the treatment probe may be configured to image the target tissue. The treatment probe may comprise an elongate structure having a working channel sized and shaped to receive an endoscope and a carrier of a carrier tube. The carrier may be configured to direct and scan a light beam on the treatment area to determine a profile of the tissue removed. The carrier may also be configured to release a fluid stream comprising a waveguide and scan the light pattern of the fluid stream comprising the waveguide. The treatment probe may be a urethral probe for tissue resection volumetric tissue removal. For example, the treatment probe may direct a fluid stream radially outwardly for controlled resection of tissue such as the prostate and luminal tissues. Optionally, the fluid stream may be used to deliver light, electrical, heat or other energy sources to aid in resection and/or to cauterize the treated tissue. Alternatively, the treatment probe can be any tools or robotic devices that can perform or assist in the urologic surgery with or without manual operations.

The imaging probe may comprise or be supported by an articulating arm or mechanical arm 14 extending from the base. The mechanical arm may be connected to a proximal end 12-1 of the elongate imaging probe 10. In some embodiments, the articulating arm or mechanical arm may comprise an actuator 117 to manipulate the imaging probe under user control. In some cases, the entire or at least a portion of the base or the articulating arm may be covered by the drape, and the proximal end of the imaging probe may be entirely covered by the canopy portion of the drape. For instance, as shown in FIGS. 1A and 1B, the proximal end of the TRUS probe may be covered by the canopy portion of the first portion of the surgical drape, and the articulating arm may be covered by a non-canopy portion of the first portion.

The imaging probe, for example a distal portion 12-2 of the imaging probe 10, can be inserted into the patient in one or more of many ways. The imaging probe can comprise an ultrasonography probe. A proximal portion of the ultrasonography probe may be mounted on the articulating or mechanical arm 14 and a distal portion 12-2 of the ultrasonography probe may be inserted into the patient. During insertion, the articulating arm 14 may have a substantially unlocked configuration such that the imaging probe can be desirably rotated and translated in order to insert a distal portion 12-2 of the probe into the patient. When the imaging probe has been inserted to a desired location within the patient, the articulating or mechanical arm 14 can be locked. In some cases, the imaging probe and the treatment probe may be inserted into the patient sequentially or concurrently. In a locked configuration of the imaging probe, the imaging probe and/or the treatment probe can be oriented in relation to each other in one or more of many ways, such as parallel, skew, horizontal, oblique, or non-parallel, for example. It can be helpful to determine the orientation of the probes with sensors such as angle sensors, in order to map the image date of the imaging probe to coordinate references of the treatment probe. Having the tissue image data mapped to treatment probe coordinate reference space can allow accurate targeting and treatment of tissue identified for treatment by an operator such as the physician. Accordingly, it is ideal for the imaging probe to be capable of moving with unimpeded and few restrictions while being covered by the surgical drape.

In some embodiments, the treatment probe 16 may be coupled to the imaging probe, in order to align treatment with the treatment probe based on images from imaging probe. The coupling can be achieved using a base that is common to the treatment probe and the imaging probe. The imaging probe can be coupled to the base with the articulating or mechanical arm 14, which can be used to adjust the alignment of the imaging probe when the treatment probe is locked in position. The articulating or mechanical arm 14 may comprise a lockable and movable probe under control of an imaging system or of the console and of a user interface, for example. The articulating or mechanical arm 14 may be micro-actuable so that the proximal end 12-1 of the imaging probe 12 can be adjusted with small movements, for example a millimeter or so in relation to the treatment probe.

The movement of the imaging probe 12 or the proximal end 12-1 of the imaging probe may range from millimeters to centimeters. For instance, the proximal end of the imaging probe may move within a space having a dimension (e.g., length, width, height, diameter, diagonal) of at least 10 cm, 20 cm, 30 cm, 40 cm, 50 cm, 60 cm, 70 cm, or 80 cm. The proximal end of the imaging probe may be configured to move freely with respect to up to six degrees of freedom (e.g., three degrees of freedom in translation and three degrees of freedom in rotation).

As shown in FIGS. 1A and 1B, the canopy portion 111 provides a working space or volume 114 for the imaging probe 12 to move therein with reduced restrictions. The working space 114 is helpful to reduce physical interference between the imaging probe and the drape when the imaging probe moves. In some cases, the canopy portion may be configured to move with the proximal end of the imaging probe 12 as a whole while the remaining portion of the drape is still supported in place. Additional details regarding the canopy portion are described later herein.

The surgical drape 100 may comprise an aperture or fenestration 118 allowing access to the urethra by the treatment device or probe. The fenestration 118 may allow access to the organ that is isolated from the remainder of the patient's body covered by the drape. Alternatively, the fenestration 118 may allow access of a surgical instrument through the drape. The aperture or fenestration may be a through hole formed in the second portion 130 of the surgical drape or the first portion 110 of the surgical drape. The aperture or fenestration, in some embodiments, may be located adjacent to the canopy portion 111.

The surgical drape may be removable from the patient or the surgical system. Removal of the drape can be achieved by a perforation 132 which may extend along or be at any angle to a midline of the drape to the fenestration. This is helpful to provide an easy removal of the drape after the urology procedure with instruments like catheters still in place. In some embodiments, the perforation 132 need not extend along the midline of the drape, and may be offset from the midline of the drape by a distance, for example around 5 cm, 10 cm, 20 cm, 30 cm, 40 cm, or 50 cm. In some cases, perforation may include various other mechanisms such as zipper, buttons, sliders, ripcords and the like.

The surgical drape may further comprise a container portion 140 for receiving waste generated during the surgical procedure. For example, in the male urology procedure, it is common that sizable amounts of liquids may be released from the urethra or other instruments. The container portion 140 can be a collection repository for body and irrigation fluids flowing from the patient during examination and surgery. In some embodiments, the container portion 140 may comprise a hole 142 allowing bodily fluids exiting therefrom. The container portion 140 may include a drainage area and/or funnel, which can direct body and irrigation fluids to another container situated below the container portion. Moreover, the container portion 140 may provide effective fluid management and may be compatible with a suction irrigation system. In some cases, the container may comprise an opening and configured to receive and store waste including bodily fluids, surgical-related fluids, tissue or debris generated during the surgical treatment.

The surgical drape may comprise attachment 150 to assist in locating and supporting the container portion 140 in position, particularly when the container is holding fluids contributing additional weight to the container. The attachment may be a component of the surgical drape or the container portion. The attachment may be a standalone element releasably attached to the surgical drape or the container portion. The attachment is useful for supporting the container portion when the container is holding fluids. For instance, in the event of a malfunction in the suction irrigation system, a sizable amount of fluids may be disposed into the container, and the drape may sag downwards due to the weight of the liquids in the container. The attachment 150 may comprise tethers or straps to support the container and prevent the drape from sagging. The tethers or straps can be attached from an opening side of the container portion to the legs 24 of the patient or the operation table. For example, the straps or tethers may be wrapped around the legs 24 of the patient over the drape or may be affixed to the operation table. The tethers can be coupled to a bed rail, a surgical arm, or to a physician. In some cases, the straps or tethers may be attached to a garment/gown of the physician, or attached to a halter that the physician wears around his or her neck. In some cases, the attachment may comprise a U-ring device configured to be attached to one side of an operation table, or an end of an operating table. Accordingly, the attachment 150 can allow the weight of the container portion to be partially supported by the legs of the patient or the operation table. The legs of the patient may be covered by the second portion 130 or the first portion 110 of the drape. The legs of the patient may or may not be visible by a physician through the drape.

Figure 2:
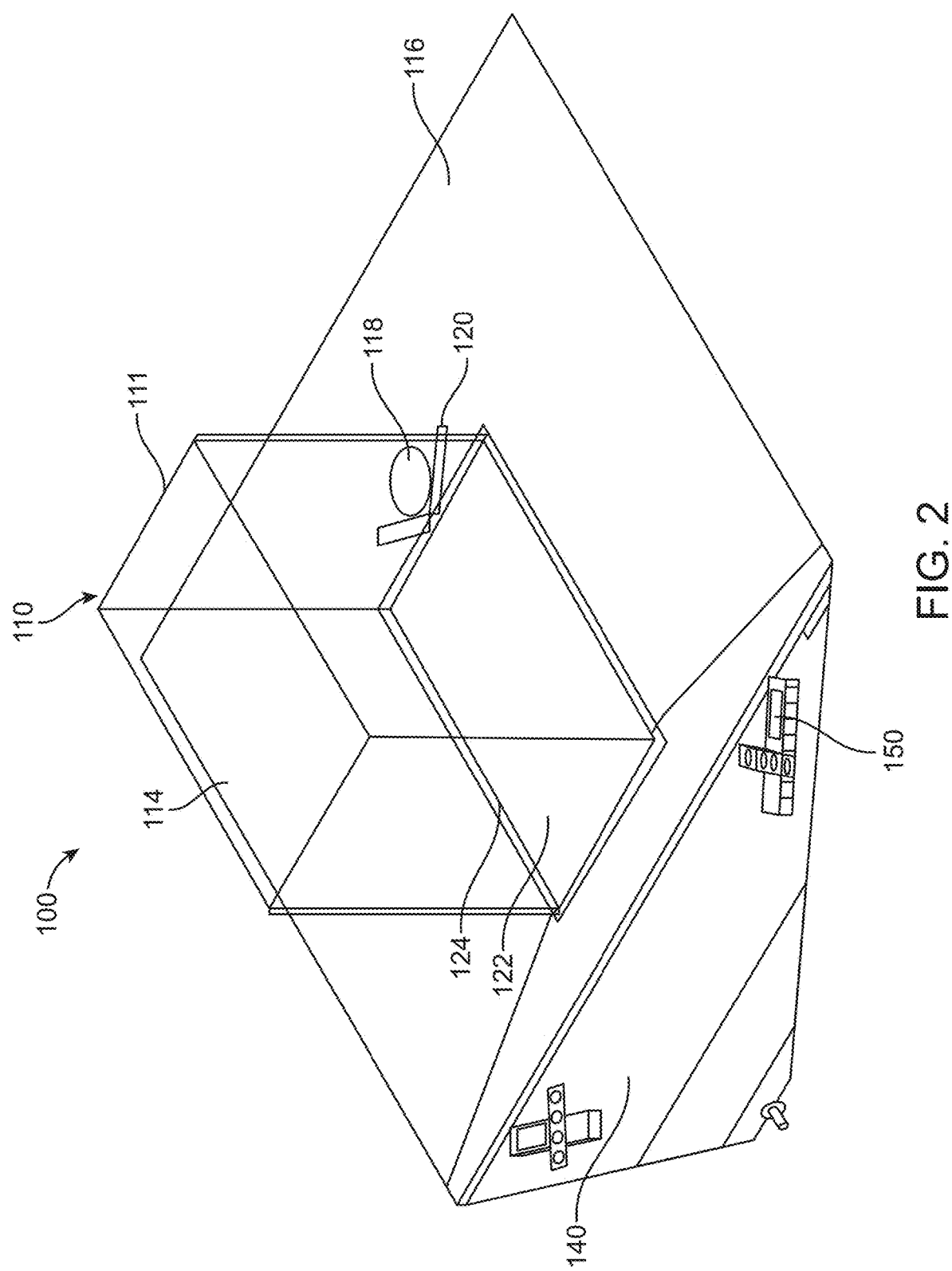
FIG. 2 shows a first portion of a surgical drape, in accordance with some embodiments.

FIG. 2 shows a first portion 110 of a surgical drape, in accordance with some embodiments. The first portion 110 may comprise a single sheet of material or multiple sheets of material, such as extruded or coextruded material. In some embodiments, the first portion may comprise multiple sheets of a same material that are stacked together. In other embodiments, the first portion may comprise multiple sheets of different materials that are stacked or sandwiched together. The first portion 110 may comprise a visually transparent or semi-transparent portion. The first portion may comprise, for example, clear plastics, or a latex thin film. The first portion may or may not have color. The first portion may be clear without color. Alternatively, the first portion may have color such as blue, green, yellow, red, or any other colors. The first portion may comprise a uniform color or a mixture of various different colors. The sheet(s) of material used for the first portion may be constructed from readily available plastic films used in the medical field, for example, vinyl (such as polyvinyl chloride), polyethylene, polypropylene, polycarbonate, polyester, silicon elastomer, acetate and so forth.

The sheet of material used for the first portion 110 may be a transparent or translucent material that permits a user to see-through the portion during insertion or operation of an imaging probe. The sheet of material may be translucent whereby at least a portion of light is permitted to pass through the material. The sheet of material may be at least partially transparent to the visible light spectrum, such that a user can see through the portion to view an underlying object. The sheet of material may allow visual viewing of a non-sterile instrument inserted into the patient such as an imaging probe.

The sheet of material used for the first portion 110 may be impervious to liquids. For example, the material may be a hydrophobic material to prevent moisture absorption by the drape. The sheet of material used for the first portion may possess a desirable stiffness or flexibility such that an operator is able to move an articulating arm coupled to the imaging probe without tearing the first portion. The sheet of material used for the first portion may be configured having a predetermined bending stiffness, or a range of bending stiffness values. In another example, the sheet of material may have tensile modulus in a range of 0.1 GPa to 5 GPa, where GPa refers to the tensile modulus in gigapascal as will be understood by one of ordinary skill in the art. A material may be harder grade when the tensile modulus is greater. A material may be flexible or soft when the tensile modulus is small.

In selecting a sheet material for use in the first portion, factors such as softness of the sheet, breathability, adaptability of the sheet to the body contour of a patient, patient comfort, or canopy portion stiffness properties can be evaluated in conjunction with the thickness of the sheet. For instance, a sheet made of a soft material may be provided having a greater thickness than a sheet made of a harder grade material, in order to provide similar stiffening effects. The type of material and its thickness may be selected such that the canopy portion of the first portion may be configured to collapse to less than its full volume when the canopy portion is covering the proximal portion of the imaging probe, e.g. ultrasonography probe. Additionally, the type of material and its thickness may be selected such that an operator is able to manipulate an articulating arm through the surgical drape without tearing any portion of the drape. In some embodiments, the canopy portion or the first portion of the drape may comprise a thin flexible material having a thickness raging from about 0.05 mm to about 3 mm, for example from about 0.25 mm to about 3 mm. Alternatively, the thickness of the first portion or the canopy portion can be less than 0.25 mm or greater than 3 mm. For example, the thickness of the first portion comprising the canopy portion may comprise a thin flexible material having a thickness within a range from about 0.05 mm to about 3 mm.

The first portion may comprise a canopy portion 111. The canopy portion 111 may comprise a shape and dimension to cover at least a proximal end of an imaging probe as described elsewhere herein. The canopy portion 111 may comprise a three-dimensional space 114 sized and shaped to cover the proximal portion of the imaging probe such that the imaging probe is permitted to move in a non-restrictive manner within the three-dimensional space. The space 114 provided by the canopy portion may be sufficient to accommodate movement of the imaging probe, without the canopy portion or other portions of the drape interfering with the movement of the imaging probe. The space 114 provided by the canopy portion may be greater than a working space required by the imaging probe. The canopy portion can be adapted for imaging probes of different sizes and dimensions. For example, the space provided by the canopy portion may be greater than the size or dimension of the imaging probe by at least 10%, 20%, 30%, 40%, 50%, 60%, 70%, 80%, 90%, 100%, 200%, or more. The space provided by the canopy portion may be defined by a volume, for example, 30-50 cm by 10-30 cm by 10-30 cm. The three-dimensional space may comprise a volume ranging from about 750 cm$^3$ to about 70,000 cm$^3$. In some cases, the volume of the three-dimensional space may be less than 750 cm$^3$ or greater than 70,000 cm$^3$. Alternatively, the space provided by the canopy portion may be defined by volumes at least or greater than 40 cm×45 cm×25 cm, 45 cm×45 cm×30 cm, or 50 cm×50 cm×30 cm. The canopy portion may comprise a space having a volume that is greater than a volume occupied by the proximal portion of the ultrasonography probe. For example, the volume of the space provided by the canopy portion may be at least two times greater than the volume occupied by the proximal portion of the ultrasonography probe. The canopy portion may comprise any type of material, shape and/or dimensions that allows the canopy portion to collapse to less than its full volume in a free-standing configuration, such that the canopy portion can be wrapped around the proximal portion of the ultrasonography probe or cover the proximal portion of the ultrasonography probe. The canopy portion is described to be in a free-standing configuration when the canopy portion is not covering any underlying object, and is allowed to collapse to a substantially flattened shape under its own weight. It is noted that the volume of the three-dimensional space of the canopy portion may be substantially reduced when the canopy portion is in a free-standing configuration (as compared to when the canopy portion is covering the imaging probe or proximal portion thereof). In some cases, the volume of the three-dimensional space of the canopy portion may be reduced by 50%, 60%, 70%, 80%, 90%, or more than 90% when the canopy portion is in the free-standing configuration.

The canopy portion 111 may comprise any three-dimensional shape such as cube, orb, cylinder, cone, semi-sphere, cuboid, triangular prism, hexagonal prism, pyramid, self-supporting geodesic dome, and various other forms. In some cases, the canopy portion may comprise a cuboid shape or rectangular shape. The three-dimensional shape of the canopy portion may comprise any number of facets or edges where the adjoining facets meet. For example, the three-dimensional shape may include one, two, three, four, five, six, seven, eight, nine, ten or more facets. The three-dimensional shape of the canopy portion can be formed using any manufacturing or fabrication methods known to those skilled in the art. For instance, the canopy portion can be formed by a thermoforming process to mold a sheet of plastic material into a desired three-dimensional geometry or by joining a plurality of pieces of material together such as using heat sealing.

In some cases, the first portion 110 may comprise a base portion 116 connected to the canopy portion. The base portion 116 may be an outer section of the first portion. The base portion may be a substantially flat portion of the first portion and may be configured to wrap around at least the mechanical arm coupled to the ultrasonography probe or the proximal portion of the ultrasonography probe, such that the canopy portion collectively moves with the mechanical arm and the proximal portion of the ultrasonography probe. The canopy portion 111 may comprise a separate sheet of material that is attachable to the base portion 116. The first portion may comprise a first sheet of material, and the canopy portion 111 may comprise a second sheet of material that may or may not be the same as the first sheet of material. The canopy portion 111 may be attached to the outer section of the first portion 110 or the base portion 116. For example, the edges of the opening of the canopy portion may be sealed or sewn to the inner edges 124 of the outer section of the first portion or the base portion 116. The inner edges 124 may also be referred to as the inner cut-out of the outer section of the first portion. The inner cut-out of 124 may comprise a shape and dimension to match the opening of the canopy portion. The canopy portion can be coupled to the outer section of the base portion in a variety of ways. For example, the edges of the opening of the canopy portion may comprise flanges to seal the canopy portion of the inner cut-out of the outer section of the base portion 116. The inner edges or the inter cut-out 124 of the outer section of the first portion or the base portion 116 may define a hole 122 therein. The canopy portion may be attached to the outer section of the first portion or the first portion 116 to cover the hole 122. Alternatively, the canopy portion may be integrally formed with the first portion. For example, the canopy portion may be formed from the same sheet of material as the first portion. The canopy portion may be visually transparent or semi-transparent to allow viewing of the imaging probe and/or alignment of the probe to the patient's body.

Figure 3B:
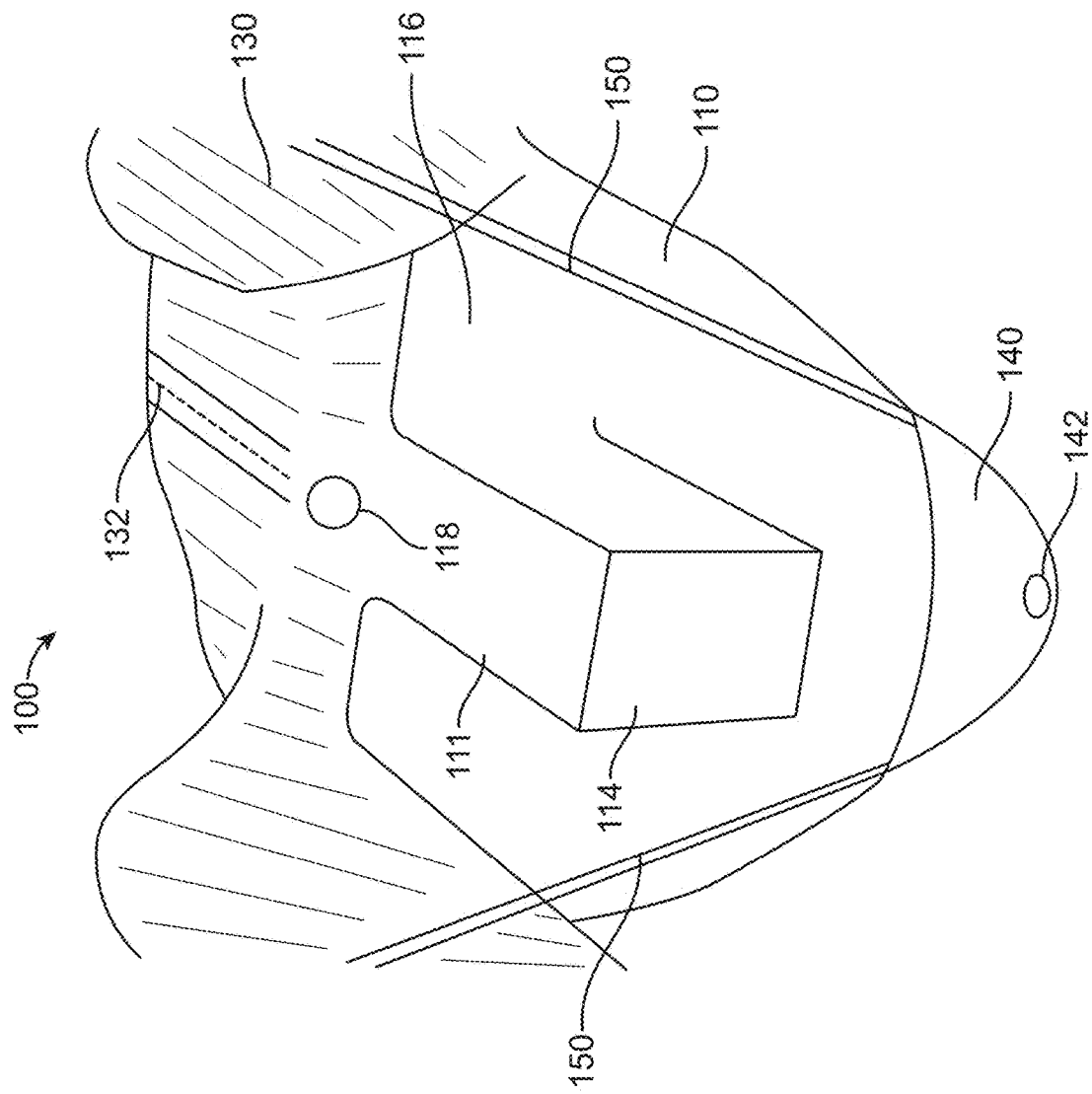
FIG. 3B provides a perspective view of the drape.

The first portion 110 may be coupled to the second portion 130 and a container portion 140 of the drape 100. FIG. 3A provides a top planar view of the drape 100 as seen from above the patient, and FIG. 3B provides a perspective view of the drape 100.

In some embodiments, the first portion 110 may comprise a fenestration 118 sized and shaped to receive a treatment probe to be inserted into a urethra of the patient. Alternatively, the fenestration 118 can be formed in the second portion 130. In some cases, the fenestration 118 may be formed in the first portion 110 above the canopy portion 111. The first portion 110 may permit viewing of the ultrasonography probe and can maintain sterility of the treatment probe when the treatment probe is inserted into the urethra of the patient. The fenestration 118 may be formed having any shapes such as circular, rectangular, square and various others. The fenestration 118 may have any dimension. For instance, the fenestration may have a diameter or length in a range of about 1 cm to 20 cm.

In some cases, the fenestration 118 may comprise reinforcement elements 120 attached to the peripheral of the fenestration to provide reinforcement to the fenestration upon insertion of an instrument or male organ. The reinforcement elements 120 may comprise a diaphragm surrounding the fenestration or partially surrounding the fenestration. The reinforcement elements can comprise a material which possesses the same degree of flexibility and rigidity as, or may be softer or more rigid, than the material used for the fenestration/transparent portion. The reinforcement elements may comprise opaque, translucent or transparent materials, and these reinforcement elements may provide visual contrast to enhance identification of the fenestration. The reinforcement elements may comprise materials that are flexible or elastic, and that possesses sufficient rigidity to prevent an instrument such as a treatment probe from penetrating or tearing the drape. In some cases, the reinforcement elements may comprise an elastic gather that cinches around the organ for maintaining integrity of the sterile field. Alternatively, the reinforcement elements may comprise an adjustable closure to cinch around the organ for maintaining integrity of the sterile field. Additionally or optionally, the reinforcement elements may comprise an adhesive material to gather drape and attach around the organ for maintaining integrity of the sterile field.

The surgical drape may comprise a container portion 140 for management of fluids generated during a surgical procedure. The container portion 140 may comprise a sheet of material which is impervious to liquids. The container portion 140 may be removable or releasably attached to other parts of the drape. For instance, the container portion may be a liquid pouch that can be attached to a lower portion of the drape under the canopy portion. The liquid pouch may be attached to the drape via any suitable means such as, for example, strips, ribbons, buttons, self-adhesive strips or tabs. Alternatively, the container portion 140 may be integrally formed with the first portion. In some embodiments, the container portion 140 and the first portion of the drape may be formed from the same sheet of material. In some cases, the container portion 140 may comprise joined edges 146 such that the sheet of material in a triangular shape may be folded and joined at the joined edges to form the pouch. Alternatively, the container portion 140 may not be formed with the joined edges. As illustrated in FIG. 3A, the container portion 140 may be positioned below the canopy portion 110 to receive fluids flowing downwards.

The container portion 140 may comprise any shape that aids in collecting and/or directing fluids to flow towards the exit port. In some embodiments, the container portion may comprise a substantially conical funnel shape to allow fluids to drain to the exit port. In another example, the container portion may comprise a substantially rectangular form having an angled or sloped bottom that allows fluids to drain to the exit port.

The container portion 140 may include a drainage area and/or funnel for directing body and irrigation fluids to another container or suction system (not shown). For example, the container portion may comprise a screen 148 attached to a lower inner side of the container portion allowing bodily fluids passing through. The screen 148 may comprise mesh with pores to prevent clogging of the exit port 144. The pore size may vary in a range, for example, from 1 mm to 20 mm. In some cases, the waste is passed through the screen, and the screen is configured to collect the tissues or debris generated during the surgical treatment. In some instances, the debris or tissues collected by the screen may be used for further diagnosis or analysis. In some instances, if the container portion prolapses, the screen may bunch up to allow airflow to the exit port. In some cases, the screen 148 may be detachable from the container portion, and can be sealed and used as storage container for containing the collected samples. In some cases, the screen 148 may have sides made from material that is impervious to fluids to eliminate drips during storage or transport. In some cases, the screen may have a closure (zipper, zip-lock, adhesive seal, draw-string, clip, elastic, conformable wire, etc.) for securing the collected samples for storage or transport. In some cases, the screen 148 may comprise a transparent portion compatible with imaging modalities for tissue analysis.

The container portion can provide effective management of fluids, and can be compatible with a suction irrigation system. In some embodiments, a suction irrigation system may be provided, and the container portion may comprise an exit port 144 at the bottom of the container configured to connect to the suction irrigation system. For example, the container portion may comprise an exit port with a sealing flange at the bottom of the container portion to be connected to a suction irrigation system (not shown).

Figure 3C:
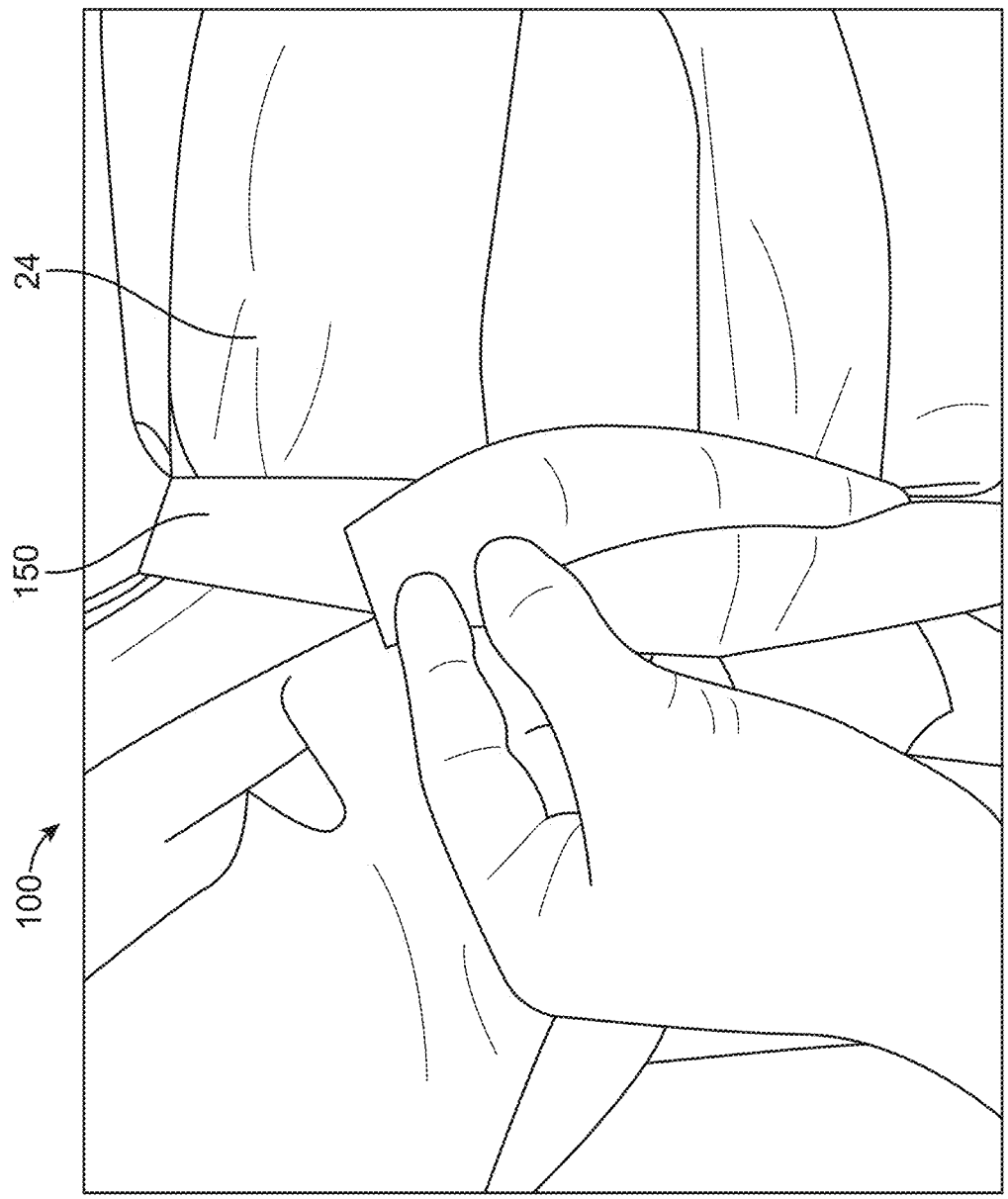
FIG. 3C shows straps or tethers wrapped around the legs of the patient over the drape, in accordance with some embodiments.

The container portion 140 may comprise attachment 150 to support the container when it holds fluids. The attachment 150 may be used to attach an opening of the container portion to an upper portion of the non-transparent portion of the drape, in order to support the fluid-holding container. The attachment 150 may comprise straps or tethers that prevent the drape from sagging. For example, the straps or tethers may be used to attach an opening side of the container portion to the legs of the patient or to the operation table. For example, as illustrated in FIG. 3C, the straps or tethers 150 may be wrapped around the legs 24 of the patient over the drape. The straps or tethers may also be affixed to the patient using adhesive tape provided at the end of the straps or tethers 150. Alternatively, the straps or tethers can be attached to the operation table, structures mounted to the operation table, or to the drape. The straps or tethers can be rolled up or folded prior to use (as shown in FIG. 3A). For example, the straps or tethers may be folded and secured by securing tapes 152 prior to use. The straps or tethers 150 may have a length of at least 50 cm, 100 cm, 120 cm, 130 cm, 140 cm, 150 cm, 160 cm, 170 cm, 180 cm, 200 cm, or 250 cm. Any number or type of attachments can be used for holding the container portion in place. Although the illustrated invention shows two tethers attached to both sides of the opening of the container, any number of tethers (e.g. two or more) or any form of attachments (e.g., adhesives, anchoring mechanisms, Velcro, etc.) may be used to support the container portion.

The surgical drape 100 may comprise a second portion 130 coupled to the first portion 110. The second portion may be a non-transparent or opaque portion. The non-transparent portion may comprise a standard medical non-woven disposable material, and can be more opaque to provide privacy for the patient. The non-transparent portion may comprise a material that is impervious to liquids. The non-transparent portion may be sized and shaped to cover a torso 22 of the patient. The non-transparent portion may be sized and shaped to cover substantially the patient's body and at least part of the surgical system. For example, the non-transparent portion may cover a portion of the imaging probe. In some embodiments, the non-transparent portion may optionally and further comprise features such as slits 136 as shown in FIG. 3A to provide flexibility. The non-transparent portion can comprise any shape such as rectangular, triangular, square, or any other irregular shapes.

The first portion 110 and the second portion 130 may be detachably coupled to each other. Alternatively, the first portion 110 and the second portion 130 may be formed together as one piece. The first portion 110 and the second portion 130 may be stitched together as one piece. In some embodiments, as illustrated in FIG. 3A, the first portion may be coupled to a cut-out 134 of the second portion. The cut-out may allow the surgical system or the imaging probe to be more easily viewed by an operator through the first portion.

The second portion 130 may be configured to cover or wrap around patient's legs 24. The non-transparent portion may be wrapped around legs of a patient as leggings such that a tether or strap for holding the container portion can be affixed to the legs by wrapping around them over the leggings (as shown in FIG. 3C). The second 130 may or may not extend all the way down to the floor.

The surgical drape 100 may comprise a separable line or perforation 132 along a midline of the surgical drape, or at any angle to the midline of the surgical drape. The perforation 132 may extend from an edge of the non-transparent portion to the fenestration. Alternatively, the perforation may not extend to the fenestration. The perforation may assist in removal of the drape after a urology procedure when instruments such as catheters are still in place. The perforation may also allow easy separation of the adjoining surfaces of the surgical drape. In some embodiments, the perforation may comprise a segment 132-1 located in the first portion 110 of the drape and a second segment 132-2 located in the second portion 130 of the drape. In some embodiments, the perforation need not be positioned along the midline or central-line of the surgical drape. The perforation can be positioned anywhere on the drape, in a configuration permitting the drape to be split from one side through the fenestration without interference with instruments placed through the fenestration. In some cases, tapes 133 may be used to strengthen the perforation region. The tapes 133 may serve to provide a sealed barrier. The tape 133 may be applied to one side or both sides of the region where the perforation forms. The tapes 133 may be disposed on top and/or below the perforation and the tape may be impervious to fluids. For example, the tape may comprise a first tape layer on top of the perforation and a second tape layer below the perforation such that the perforation is sandwiched between the first and second tape layers. In the case when other mechanisms such as zipper, buttons, or sliders are used, the tape may also be applied to provide the seal. In some cases, the perforation comprises a sliding dove-tail mechanism that releasably opens and closes the perforation.

The surgical drape 100 can be folded into a compact packet. The folded drape may be secured in an outer wrap or by adhesive tabs. The outer wrap or adhesive tabs may be removed when the packet is unfolded.

Figure 4A:
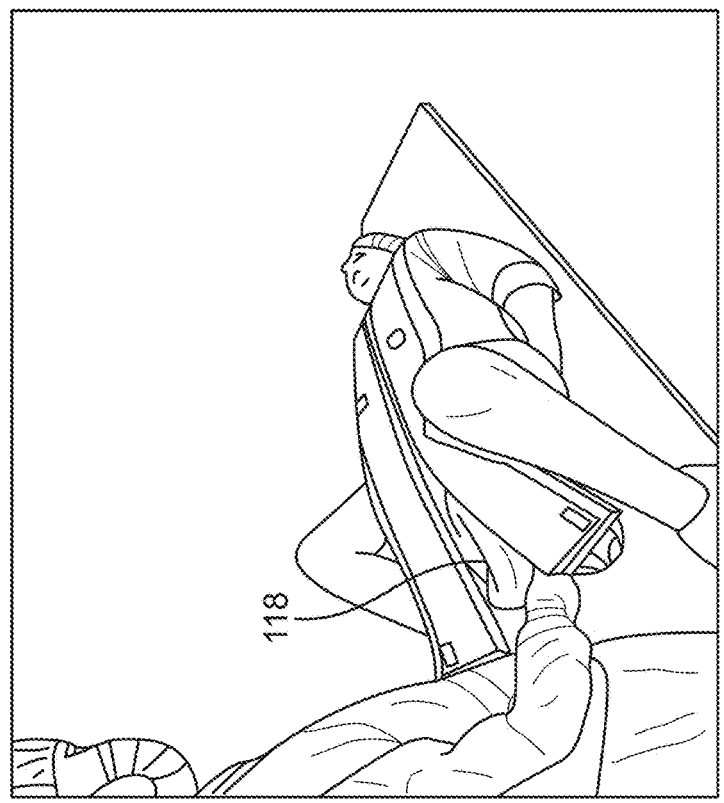
FIGS. 4A to 4C schematically illustrate a method of using the drape, in accordance with some embodiments.
Figure 4A:
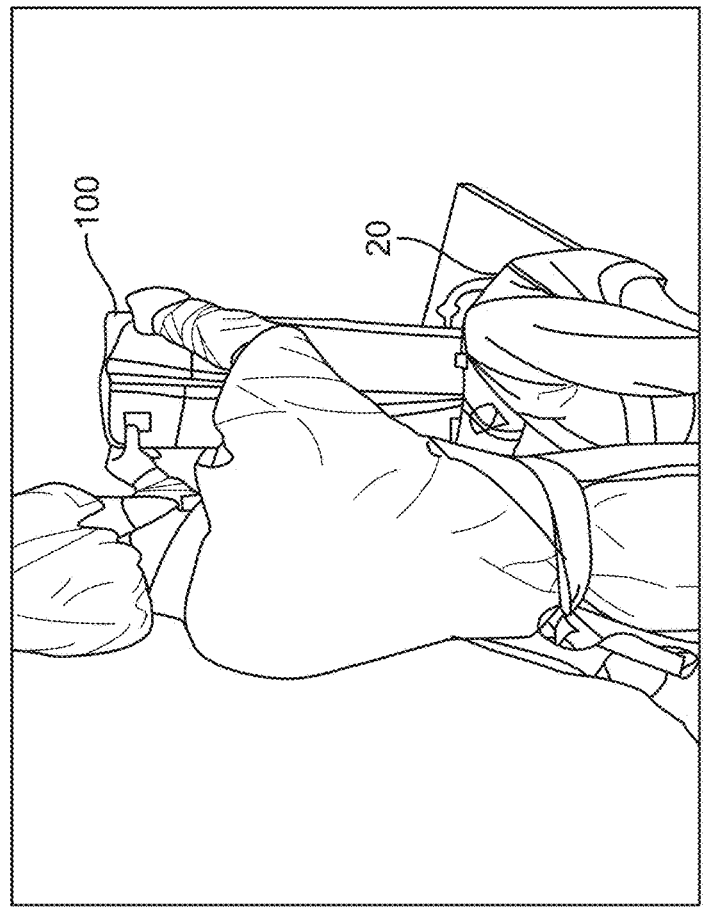
Figure 4B:
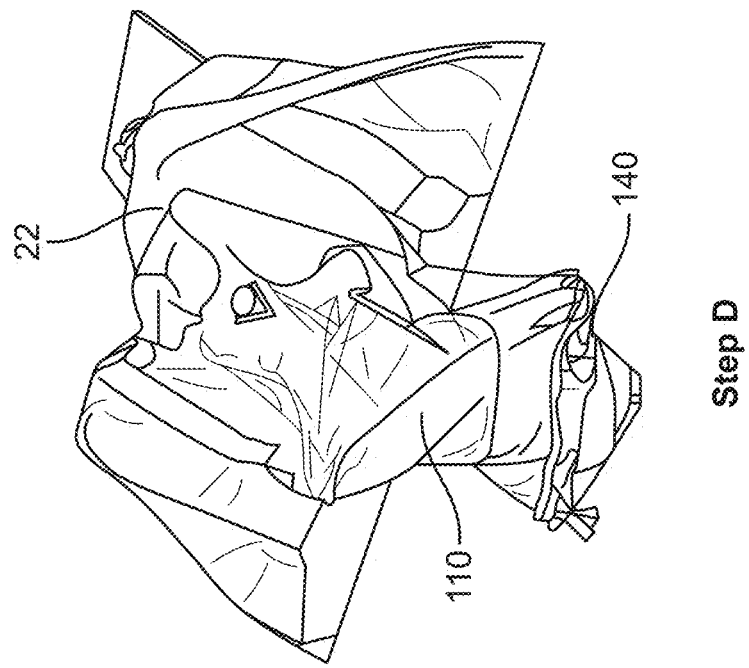
Figure 4B:
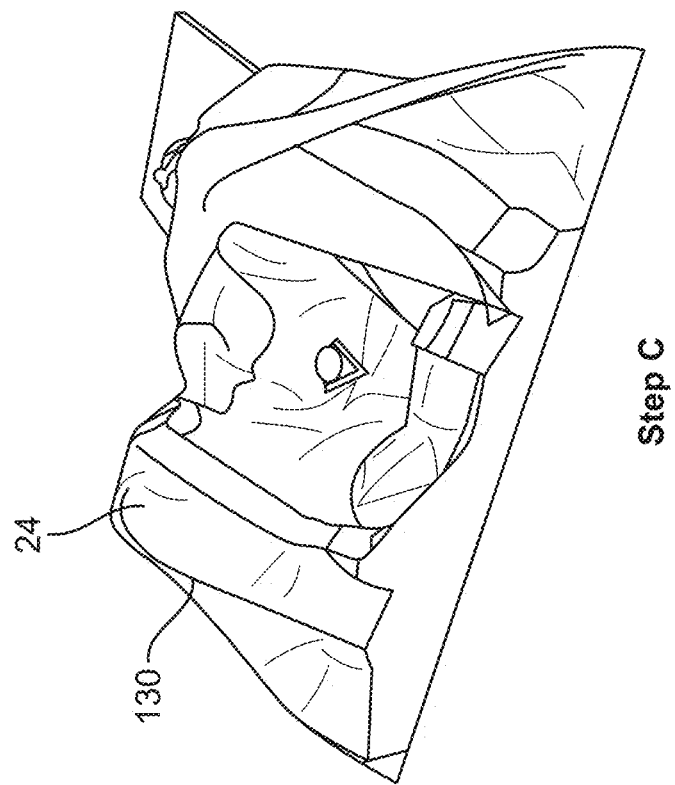
Figure 4C:
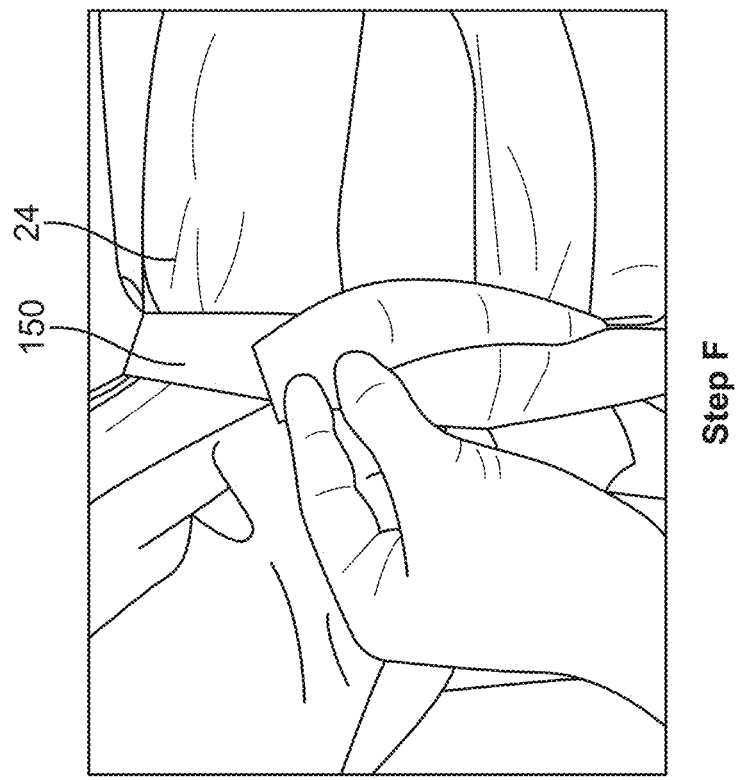
Figure 4C:
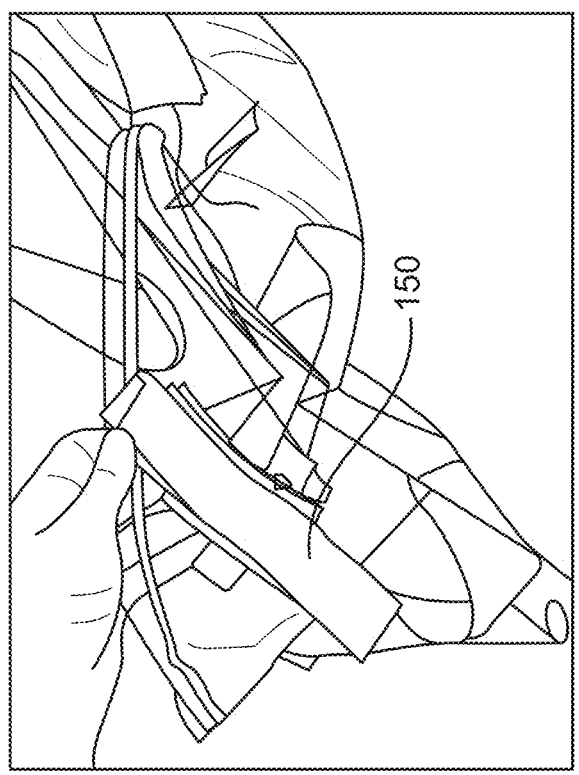

FIGS. 4A to 4C illustrate a method of using the surgical drape 100 with a patient 20 and a surgical system. As shown in steps A and B, the surgical drape 100 may be unfolded toward the patient's head, and the fenestration 118 of the drape may be positioned over the operative area of the patient. Next, the second portion 130 of the drape may be applied over the patient's leg 24 as leggings. The second portion 130 may be wrapped around covering the legs 24 of the patient, as shown in step C. The second portion 130 may also cover a torso 22 of the patient. Proceeding to step D, the first portion of the drape 110 may be unfolded to substantially cover an imaging probe (not shown) of the surgical system, and the container portion 140 may be positioned in place below the surgical area. The first portion of the drape 110 provides less physical interference or impedance to the movement of the imaging probe. The visual transparency of the first portion of the drape 100 also allows an underlying site or tool to be viewed. The container portion may 140 comprise attachment such as straps or tethers 150 for attaching the container portion to the legs of the patient or to the operation table, as described elsewhere herein. The straps help to hold the container portion to a more stable support. As illustrated in step E, the tethers or straps 150 may comprise adhesive tabs to keep the tethers or straps folded and compacted when not in use. The tethers or straps may be extended and wrapped around the leggings of the surgical drape when in use. The tethers or straps 150 may be secured in place by placing the adhesive taps on top of the strap or tether when not in use, as shown in step F. In some cases, the container portion may be configured to connect an exit port of the container portion to a suction irrigation system to remove fluids from the container portion. The surgical drape 100 can be easily removed by separation along the perforation when a surgical process is finished.

Although FIGS. 4A to 4C illustrate a method of using a surgical drape in accordance with some embodiments, a person of ordinary skill in the art will recognize many adaptations and variations. For example, some of the steps can be omitted, some of the steps replicated, and the steps can be performed in any appropriate order.

Figure 5:
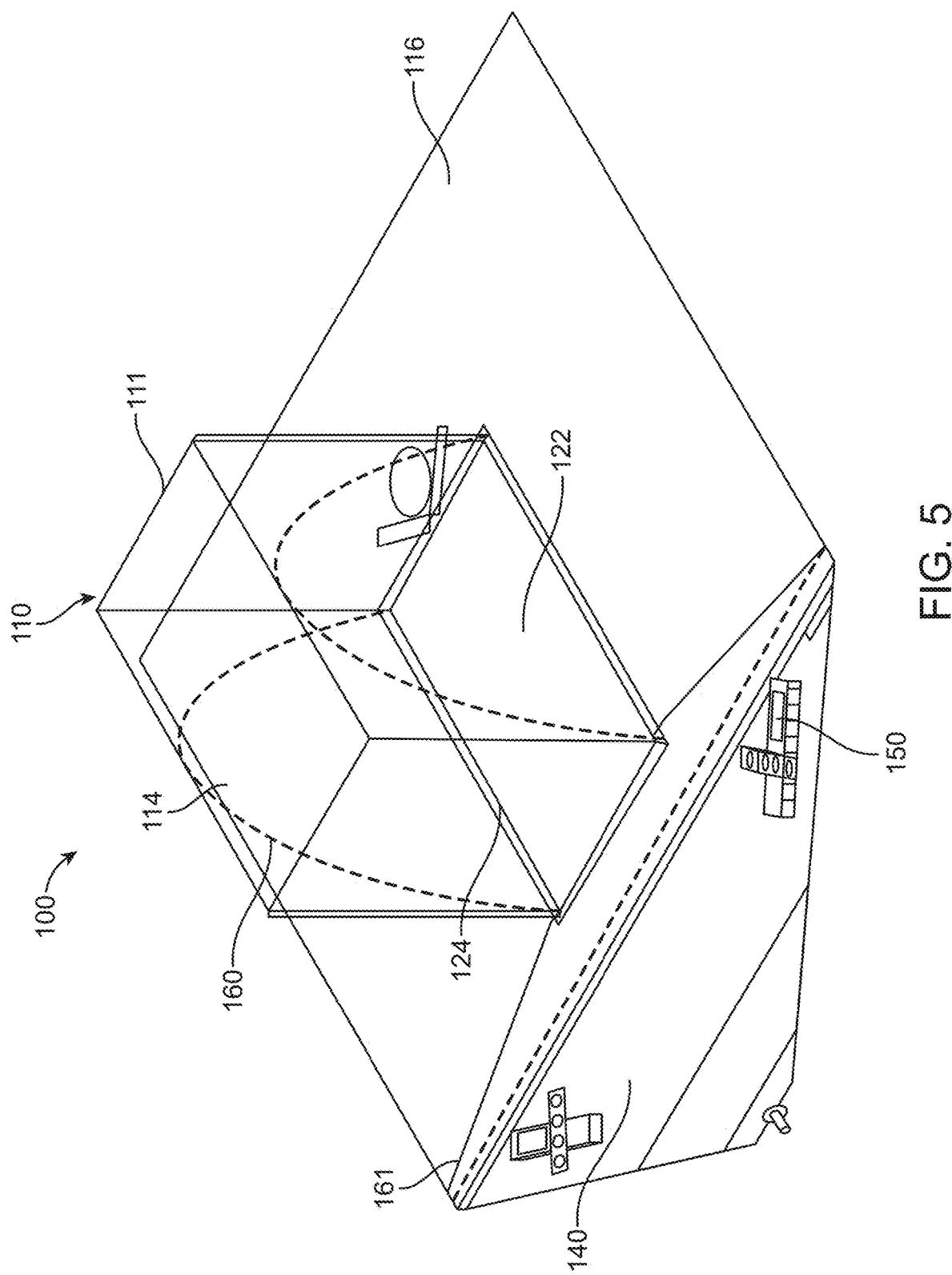
FIG. 5 illustrates a surgical drape comprising one or more frame structures in accordance with some embodiments.

FIG. 5 shows a surgical drape comprising one or more frame structures 160, that may be combined with any embodiment disclosed herein. The frame structures can be adapted to structurally maintain one or more configurations of the surgical drape. For instance, the canopy portion 111 may comprise one or more frame structures 160 to maintain or provide the working space/volume 114. The frame structures may be disposed in any location, or one or more portions of the drape. In some cases, the frame structures 160 may extend in an arc-like manner along sidewalls of the canopy portion 111, for example as shown in FIG. 5. In some embodiments, the frame structures may include a lining 161 along an opening of the container portion 140. The frame structures can be made of any suitable materials such as metal, steel, plastic, fiber glass, and the like. In some cases, the frame structures can be folded and unfolded/deployed to support a variety of different configurations. The frame structures may include or utilize spring steel or any other type of elastic structure. In another example, the frame structures may include or utilize compliant stiffening elements that are integrated into the drape material. In some embodiments, at least one of the first portion 110 or the second portion 130 of the surgical drape 100 may be operably coupled to an actuation element (not shown). The actuation element can be configured to deploy one or more sections of the surgical drape from a compact configuration to an extended configuration. The compact configuration may comprise a substantially two-dimensional shape/profile, and the extended configuration may comprise a substantially three-dimensional shape/profile. The surgical drape may be in the compact configuration when the drape is not in use. The surgical drape can be deployed to the extended configuration prior to or during use of the drape for the surgical treatment of the patient. The extended configuration may correspond to a useable state/position for the drape. The actuation element may be integrated into the surgical drape, or included with the drape. In addition to deployment, the actuation element can further provide structural reinforcement to one or more sections of the surgical drape (e.g. the canopy portion 111) in the extended configuration. Accordingly, the actuation element may comprise one or more stiffening elements. In some embodiments, the frame structures 160 shown in FIG. 5 may be the actuation element, or form part of the actuation element.

The actuation element may comprise a stored energy device. The actuation element may include one or more spring elements. Non-limiting examples of spring elements can include a variety of suitable spring types, e.g., nested compression springs, buckling columns, conical springs, variable-pitch springs, snap-rings, double torsion springs, wire forms, limited-travel extension springs, braided-wire springs, etc. Further, the actuation element (e.g., spring elements) can be made from any of a number of metals (e.g. spring steel), plastics, or composite materials. In some cases, the actuation element may include fiberglass or plastic stiffeners, which also serve as stiffening elements as described elsewhere herein.

In some cases, the one or more spring elements may include a deployment spring positioned to deploy one or more sections of the surgical drape from the compact configuration to the extended configuration. Similarly, the one or more spring elements may include a retraction spring positioned to retract one or more sections of the surgical drape from the extended configuration back to the compact configuration. In some instances, a monolithic spring can be configured to provide dual functions, e.g. (1) for deploying and also (2) for retracting one or more sections of the surgical drape. For example, the monolithic spring can be configured to transform between two or more states (fully compressed state, partially extended state, fully extended state, etc.).

In any of the embodiments disclosed herein, the actuation element can include magnets, electromagnets, pneumatic actuators, hydraulic actuators, motors (e.g. brushless motors, direct current (DC) brush motors, rotational motors, servo motors, direct-drive rotational motors, DC torque motors, linear solenoids stepper motors, ultrasonic motors, geared motors, speed-reduced motors, or piggybacked motor combinations), gears, cams, linear drives, belts, pulleys, conveyors, and the like.

As described elsewhere herein, the first portion 110 of the surgical drape 100 may comprise an opening/aperture/fenestration 118. In some embodiments, the opening may include an elastic strap or an adjustable closure that is configured to cinch around an organ of the patient as described herein, for maintaining integrity of a sterile surgical field or environment. The adjustable closure may include, for example a zipper. Additionally or optionally, the opening may include an adhesive material to gather and wrap loose sections of the drape around an organ of the patient for maintaining integrity of a sterile surgical field or environment.

The first portion 110 of the surgical drape may comprise material for covering the torso 22 or legs 24 of the patient, as described elsewhere herein.

Figure 6:
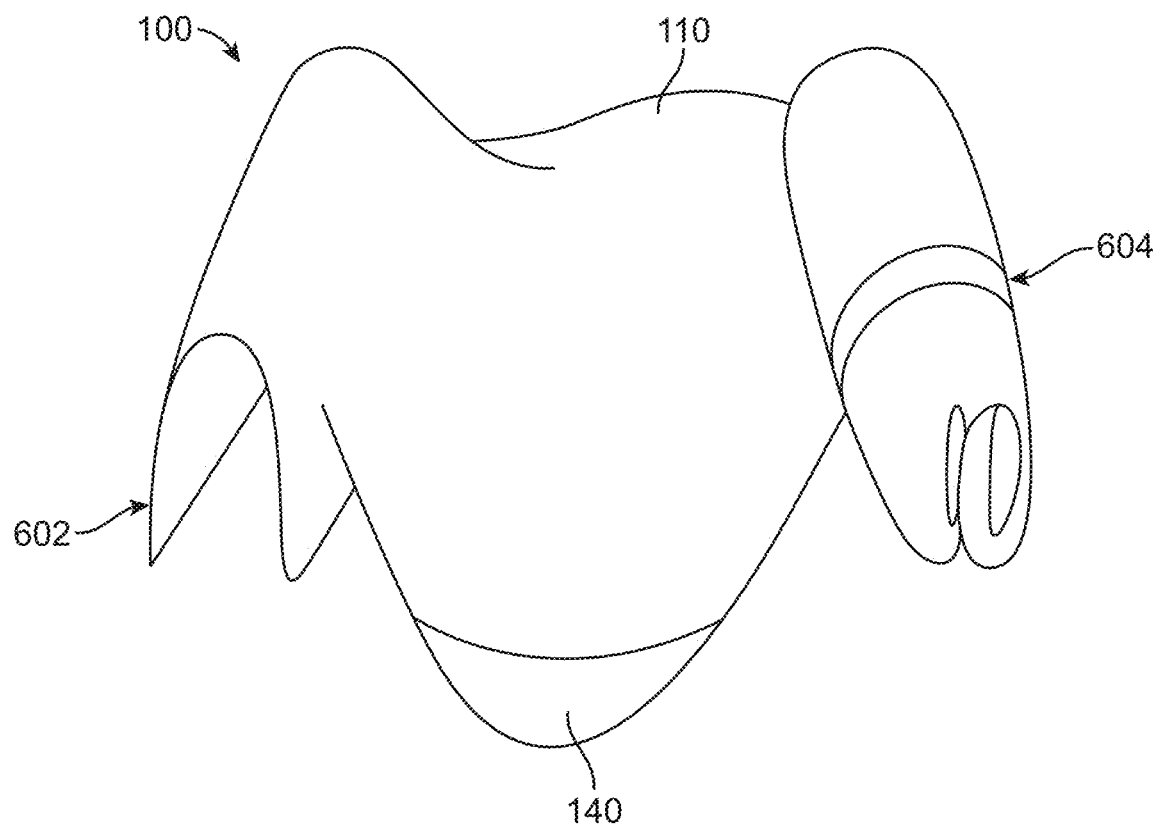
FIG. 6 illustrates material of a surgical drape hanging loosely, or wrapped around the torso or underside of the legs of a patient or stirrups, in accordance with some embodiments.

Referring to FIG. 6, the material can be configured to hang loosely 602. The material can also be wrapped around 604 the torso or underside of the legs of the patient or stirrups. The material can be secured using any means of attachment, for example straps, tethers, Velcro™, or tape. In some embodiments, the material may comprise an adhesive for attaching the material around the stirrups to form a holder, in which a container 140 for receiving and storing waste can be secured and suspended.

Figure 7:
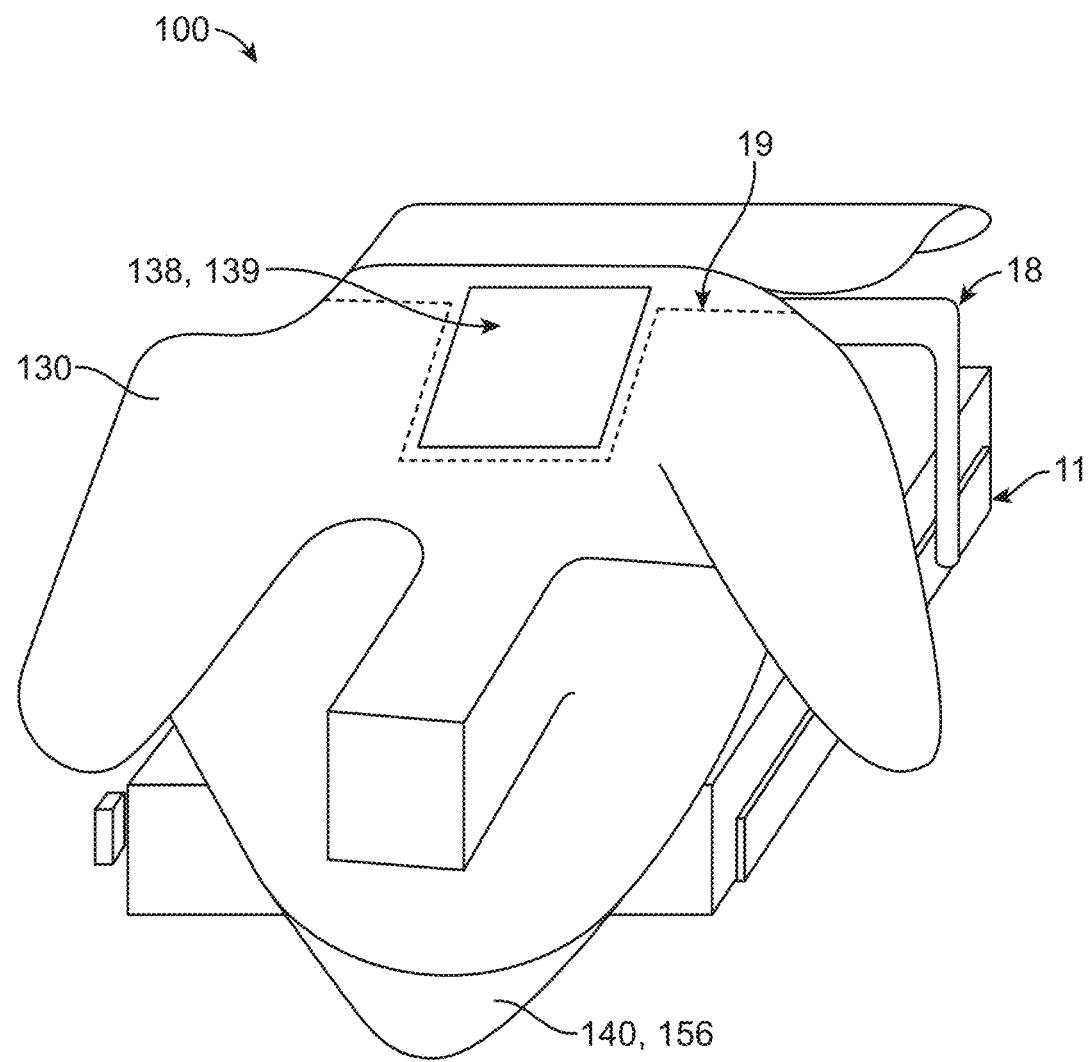
FIG. 7 illustrates a surgical drape comprising a viewing window and mounted to a support structure having a graphical display, in accordance with some embodiments.

Referring to FIG. 7, the second portion 130 of the surgical drape can be mounted to a support structure 18. The support structure may comprise one or more arms. The support structure can be attached to an operating table over or near the patient. For example, the support structure can be attached to bedrails 11 of an operating table. The second portion of the drape 130 can be mounted to the support structure, and similarly the support structure can be attached to the operating table using any means of attachment, for example straps, tethers, Velcro™, or tape.

In any of the embodiments disclosed herein, the support structure 18 can be coupled 19 to a graphical display (not shown). The display may be supported beneath the drape, or supported by the drape. The display may be a screen. In some cases, the display may be a touchscreen. The display may include a light-emitting diode (LED) screen, OLED screen, liquid crystal display (LCD) screen, plasma screen, or any other type of screen. The display may be configured to show a user interface (UI) or a graphical user interface (GUI). The display can be operably coupled to the imaging probe 12, articulating arm 14, and/or treatment probe 16. A physician may view real-time optical images collected by the imaging probe 12 on the display. In some cases, a physician can control one or more steps during the surgical treatment of the patient via the display (e.g. articulation of the treatment probe 16 and/or imaging probe 12 via the arm 14).

The second portion 130 of the surgical drape may comprise a translucent or transparent material 138 that permits the graphical display to be viewed through the drape. The transparent material 138 may be provided in one or more regions of the drape, for example as shown in FIG. 7. The one or more regions may include a translucent or transparent viewing window 139 such that the display can be viewed. In some embodiments, the graphical display may include a touchscreen, and the translucent material 138 may be compatible for use with the touchscreen such that a user (e.g. a physician) is able to interact with the touchscreen, with the translucent material as an intervening layer. The graphical display may be located underneath the drape, but is visible through the viewing window 139 of the drape. In some embodiments, the translucent material may be flexible or loose-fitting so as to allow a user (e.g. physician) to manually manipulate one or more input/output (I/O) devices that are connected to the graphical display. Examples of I/O devices can include a joystick, mouse, trackball, trackpad, 3-dimension cursor, button, knob, finger trigger, dials, touchscreen, touchpad, or keyboard. The translucent material may include excess or extra material to accommodate a user's manipulation of one or more underlying I/O devices.

Figure 8:
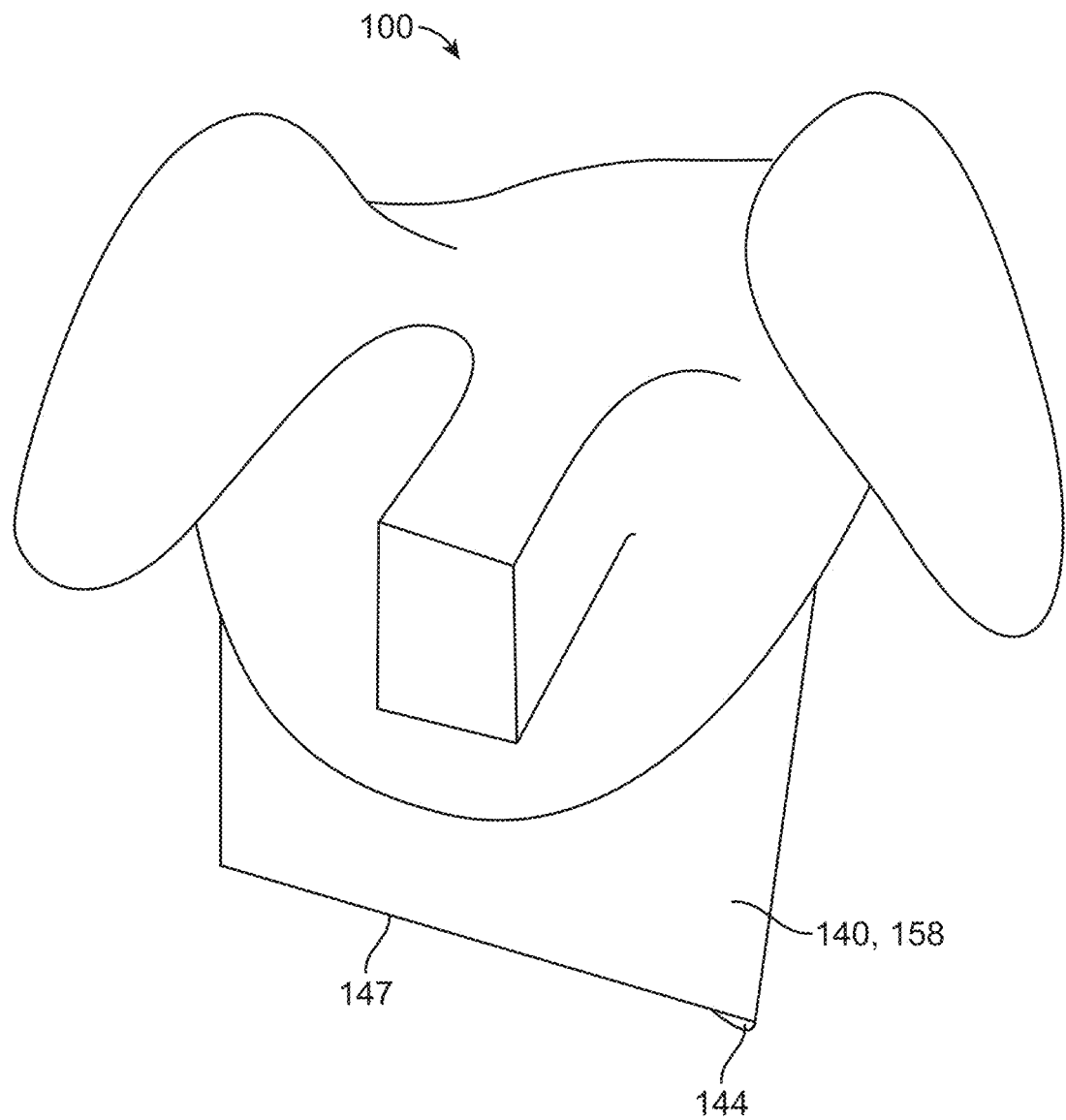
FIG. 8 illustrates a container having a substantially rectangular funnel shape in accordance with some embodiments.

The container portion 140 (henceforth referred to as container) may comprise a funnel shape to allow fluids to drain to an exit port 144. The container 140 may comprise a substantially conical funnel shape 156, for example as shown in FIG. 7. Alternatively, the container 140 may comprise a substantially rectangular funnel shape 158, for example as shown in FIG. 8. In some embodiments, the container 140 may comprise a bottom portion that is angled or sloped 147, for example as shown in FIG. 8. The angle or slope can be designed to enhance fluids flow to towards the exit port 144.

Figure 9B:
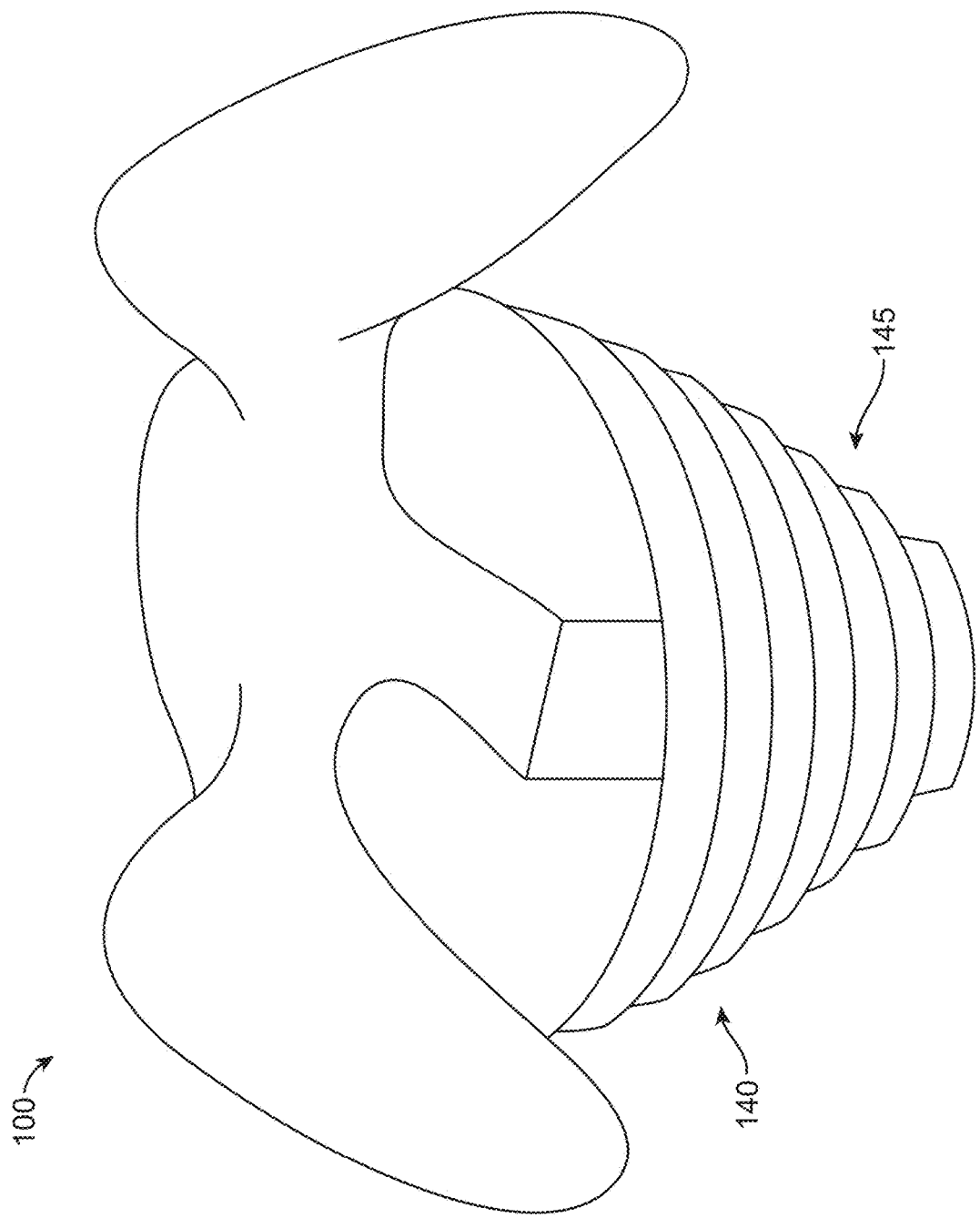
FIG. 9B illustrates a container with horizontal cylindrical stiffening pleats to create hoop strength for maintaining a structural form of the container, in accordance with some embodiments.

In some embodiments, the container may comprise structures for supporting one or more configurations of the container. FIGS. 9A and 9B illustrate a container having a substantially rectangular funnel shape with an angled or sloped bottom, in accordance with some embodiments.

The supporting structures can comprise interleaved structures, for example vertical pleats 143 as shown in FIG. 9A, or horizontal pleats 145 as shown in FIG. 9B. The vertical pleats 143 can serve or act as stiffeners that prevent the container 140 from collapsing and changing its shape/form when under load. Additionally or optionally, the vertical pleats 143 can be configured to allow airflow to vent displaced fluids as the fluids is being extracted or drained from the container 140. Referring to FIG. 9B, the horizontal pleats 145 can permit the container 140 to collapse into a collapsed or compact configuration in a telescoping manner. The container may be collapsible to a substantially planar configuration, and extendable to a substantially 3-dimensional configuration with aid of the horizontal pleats 145. The container 140 may comprise one or more flexible, semi-rigid, or rigid materials. The container 140 can be designed to achieve various desired characteristics such as strength, rigidity, elasticity, compliance, and durability. Non-limiting examples of materials may include fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials and the like.

Figure 10A:
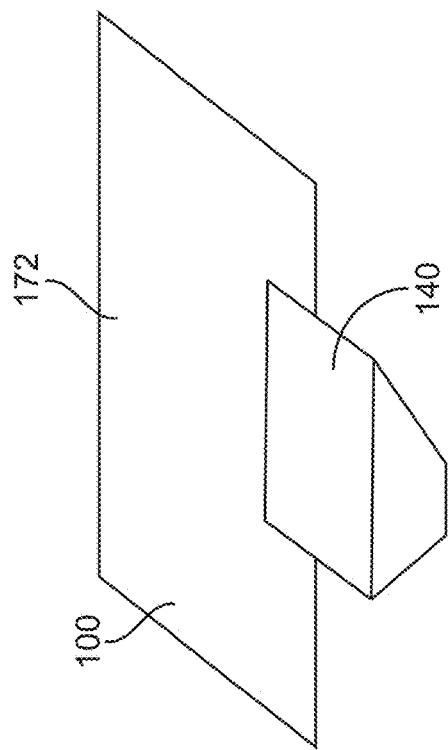
FIGS. 10A to 10D illustrates the use of a container as a packaging enclosure for storing a surgical drape, in accordance with some embodiments.
Figure 10B:
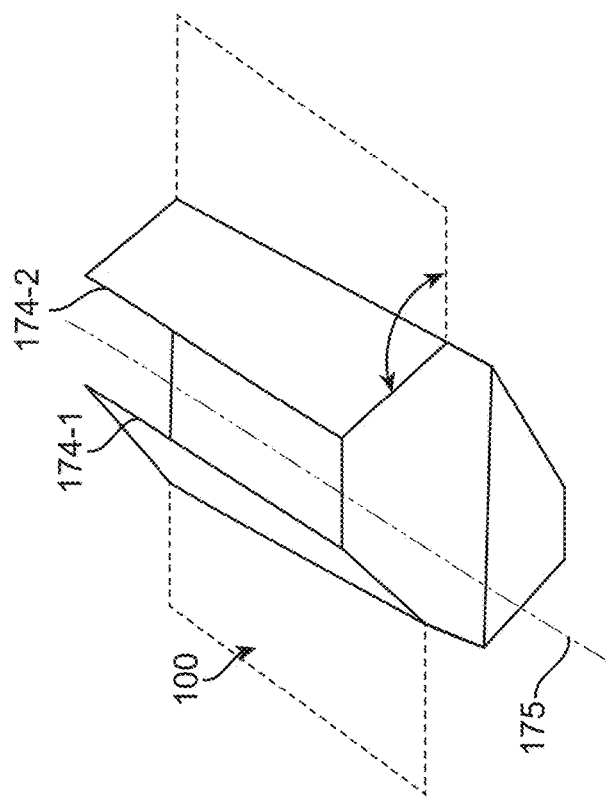
Figure 10C:
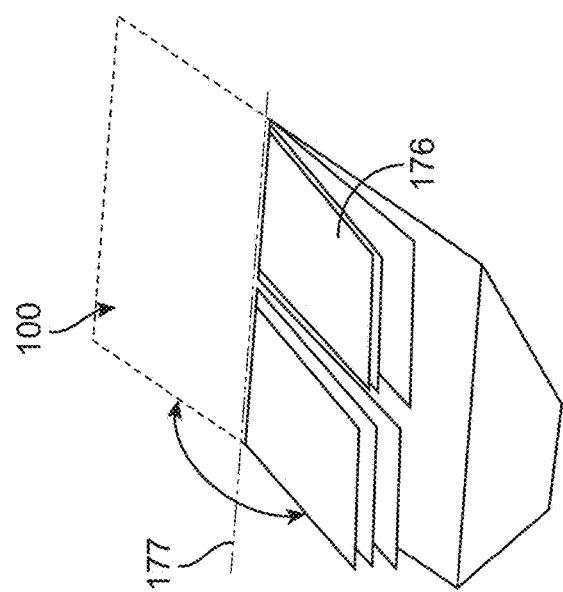
Figure 10D:
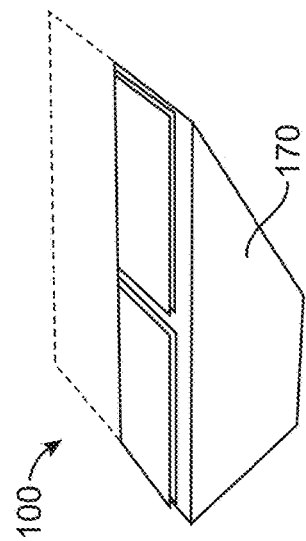

In any of the embodiments disclosed herein, the container 140 can be configured to serve as a packaging enclosure for storing the surgical drape 100 or portion thereof. The packaging enclosure can be used to store the surgical drape or portion thereof when the surgical drape is in its original state prior to use. Additionally or alternatively, the packaging enclosure can be used to store the surgical drape or portion thereof for subsequent disposal after the surgical drape has been used. FIGS. 10A to 10D illustrate an embodiment in which the container 140 can be used as a packaging enclosure 170 for storing the surgical drape 100. Referring to FIG. 10A, the drape 100 may be coupled to the container 140, and may extend outside of the container. Prior to storing the drape, the drape may be stretched out into a substantially planar configuration 172. Next, the drape may be folded in the manner as shown in FIG. 10B, by folding opposing ends 174-1 and 174-2 of the drape inward relative to a longitudinal axis 175. Next, the drape may be compacted further by folding an end 176 inward relative to a transverse axis 177, as shown in FIG. 10C. Finally, the drape can be folded and tucked into the container for storage as shown in FIG. 10D. The drape can be stored in the container when new (i.e. prior to use of the drape), and can be shipped in the container. Additionally or optionally, the drape can be stored in the container after the drape has been used (e.g. in a surgical treatment), for subsequent disposal or transportation to a disposal facility. In some embodiments, the container may include a lid (not shown) for covering the drape stored within the container.

Figure 11:
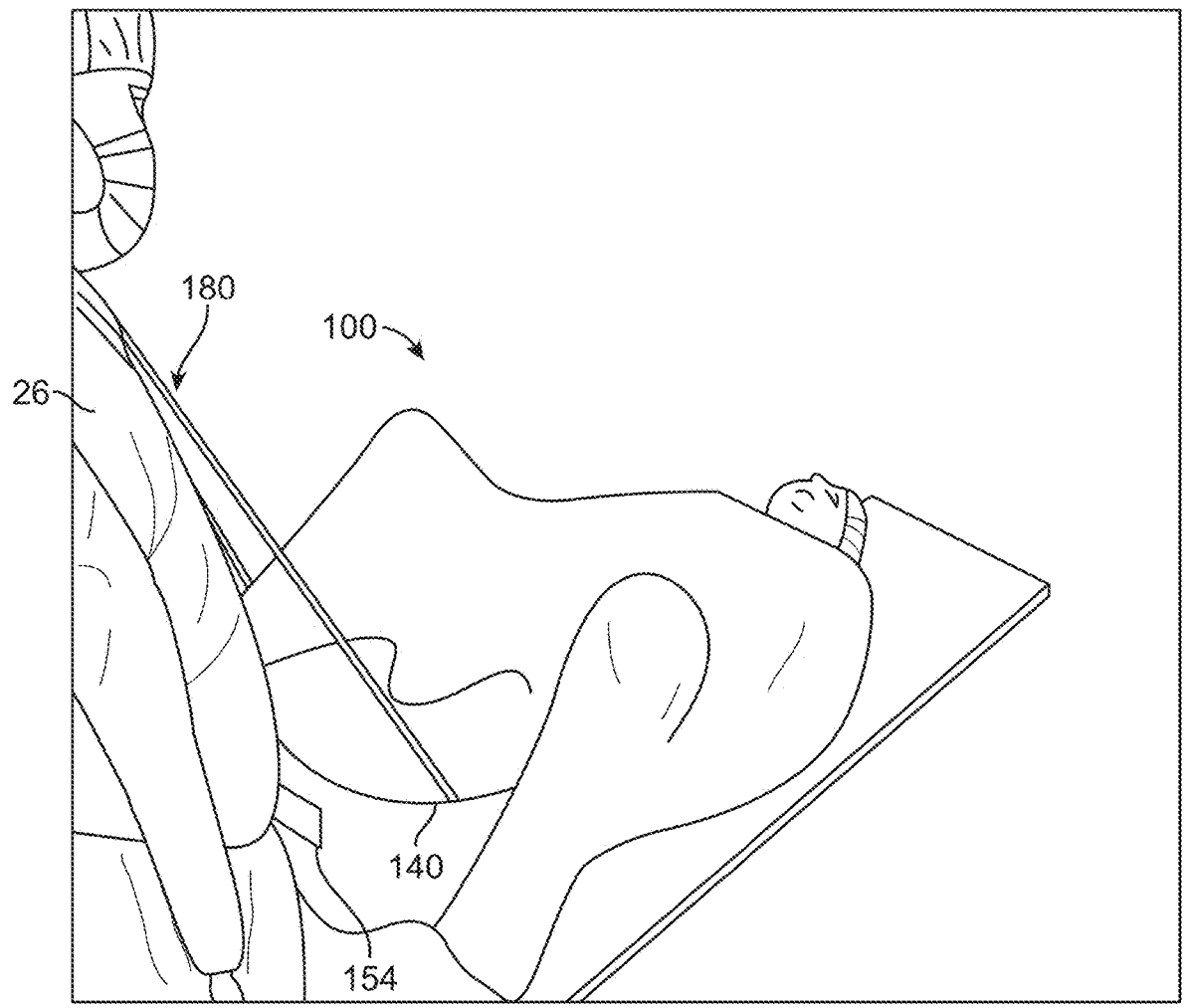
FIG. 11 illustrates a container coupled to and carried by a user in accordance with some embodiments.

In any of the embodiments disclosed herein, the container 140 can be coupled to and supported by a user, e.g. carried by a user 26, for example as shown in FIG. 11. The user may be, for example a surgeon, and the container can be coupled to the user in many ways, for example with straps or tethers such that the user at least partially supports the container. In the example of FIG. 11, the container may be coupled to a halter 180 that is configured to be worn on or around the user's neck 28, and the container may be supported by the halter around the user's neck when in use, for example. In some instances (not shown), the container may be coupled to a belt that that is configured to be worn around the user's waist. In some embodiments, the container can be releasably attached to a user's gown using one or more quick release couplings 154. The use of quick release couplings can help to improve operating room efficiency, for example by facilitating portability of containers and interchanging of used/new containers within the operating room. Examples of quick release couplings may include mechanical couplings, snapfits, adhesives, tapes, fasteners, magnets, and the like. The container may be releasably coupled to any portion of the user's gown, in a manner that aids disposal of wastes and without impeding the user's movement during the surgical treatment.

Figure 12:
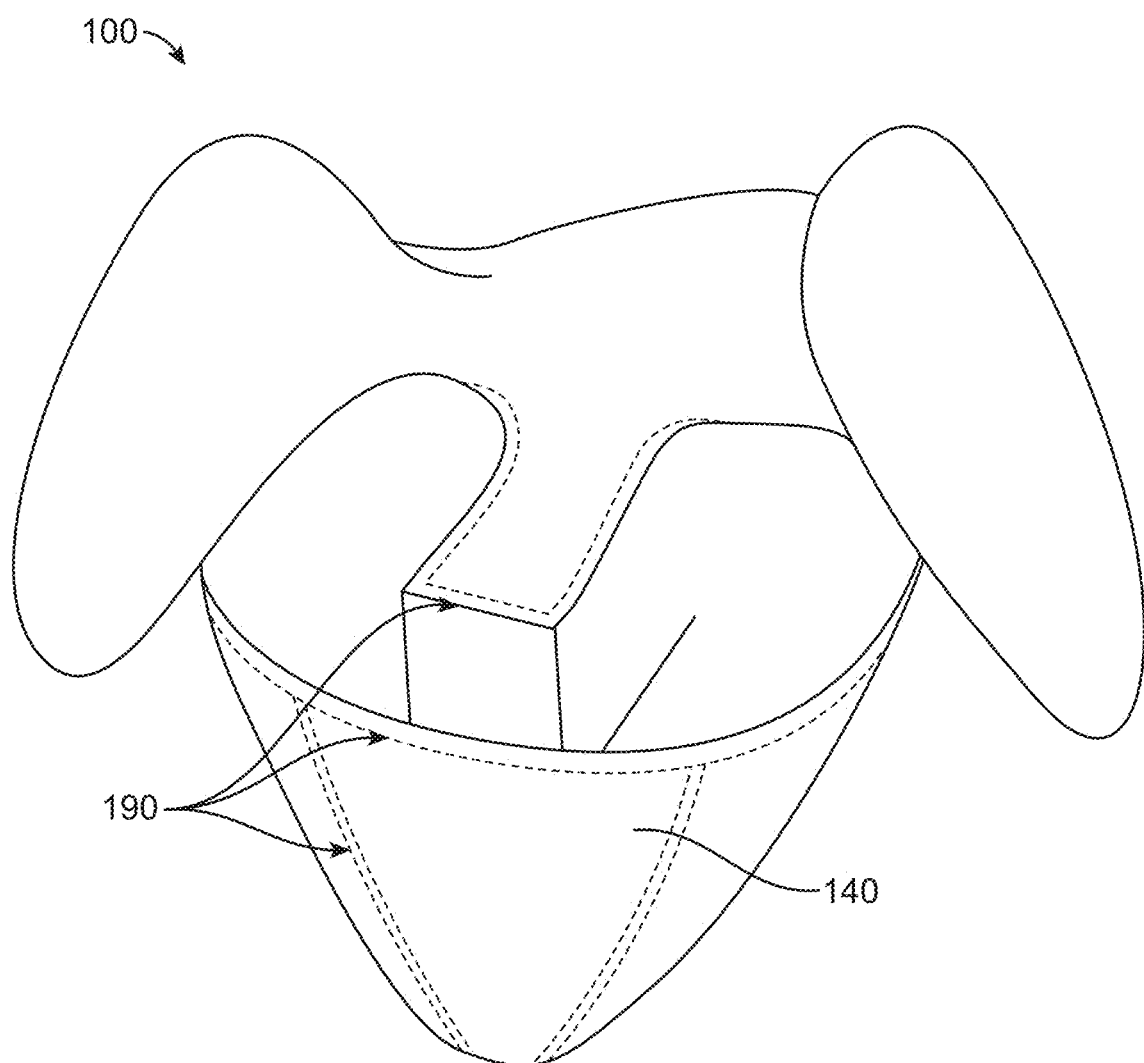
FIG. 12 illustrates a container comprising one or more compliant stiffening elements for maintaining a structural form of the container, in accordance with some embodiments.
Figure 13:
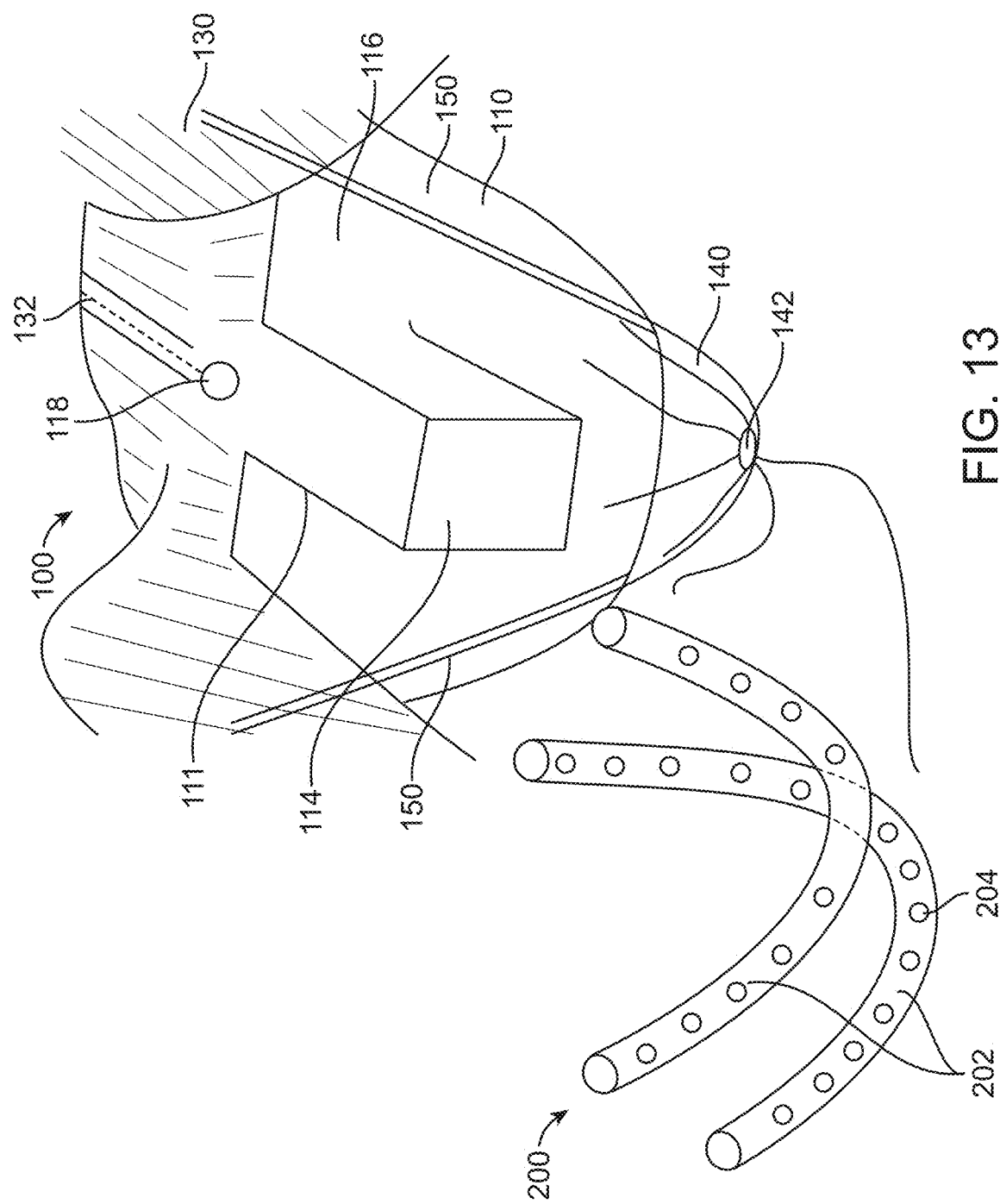
FIG. 13 illustrates a container comprising an integral perforated tubing matrix for maintaining fluid flow and air displacement, in accordance with some embodiments.
Figure 14:
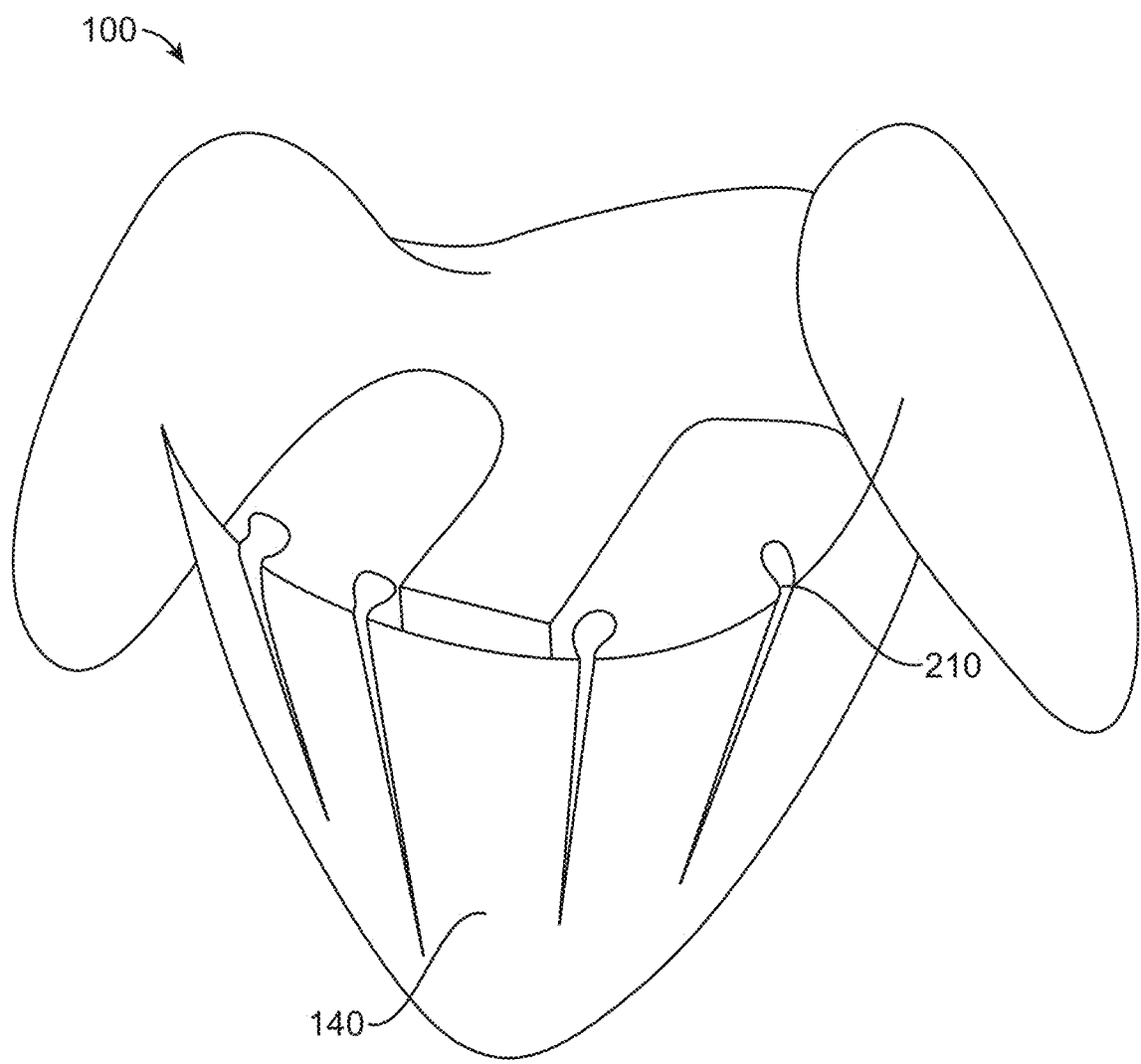
FIG. 14 illustrates a container comprising tube-like areas formed from rolled up drape material, that may be connected to a drain/suction port for maintaining fluid flow and air displacement, in accordance with some embodiments.

In any of the embodiments disclosed herein, the container 140 may comprise one or more compliant stiffening elements for maintaining a structural form of the container. At least one of the first portion 110 or the second portion 130 may comprise one or more frame structures that support a configuration of at least the first portion or the second portion. The compliant stiffening elements may be used as frame structures. For example, as shown in FIG. 12, stiffening elements 190 may be provided as rib liners extending across various parts of the surgical drape 100 and the container 140. Structural reinforcement can be advantageous for prolonging the life of the container and the surgical drape for multiple use/patient encounters. The structural reinforcement can also be advantageous for fluid management, for example during long surgeries involving significant fluid management for multiple use/patient encounters In some cases, the container 140 may comprise structures for management of fluid flow. The container 140 may comprise an integral perforated tubing matrix 200 to maintain fluid flow and air displacement, for example as shown in FIG. 13. The perforated tubing matrix 200 may be connected to a drain/suction port located at a hole 142 or exit port 144 of the container 140. The perforated tubing matrix may comprise one or more tubes 202 serving as fluidic pathways or channels. The fluidic pathways or channels may be provided adjacent to the exit port 144 to provide anti-block caused by prolapse drape. The tubes may be coupled to one another, and may intersect with one another. Each tube 202 may comprise a plurality of perforations 204. The perforations may be provided in a manner that aids in air displacement from the tubes and prevent clogging within the matrix. The fluidic channels may extend for any length along a plurality of surfaces of the drape 100 under a filter screen. For example, a plurality of fluidic channels may extend for about 5 cm to about 40 cm up the walls of the container 140 and under screen 148. The container can be designed to ensure sufficient suction of fluid from the container by (1) providing non block-able passageways for the suction to act on the fluid, or (2) by providing a mechanism that prevents material from folding over a vacuum port and blocking the vacuum port. In some alternative embodiments, the container may comprise rolled up tube-like areas 210, for example as shown in FIG. 14. The rolled up tube-like areas 210 may be formed from rolled up drape material, and may be connected to a drain/suction port to maintain fluid flow and air displacement, similar to the embodiment of FIG. 13.

Figure 15:
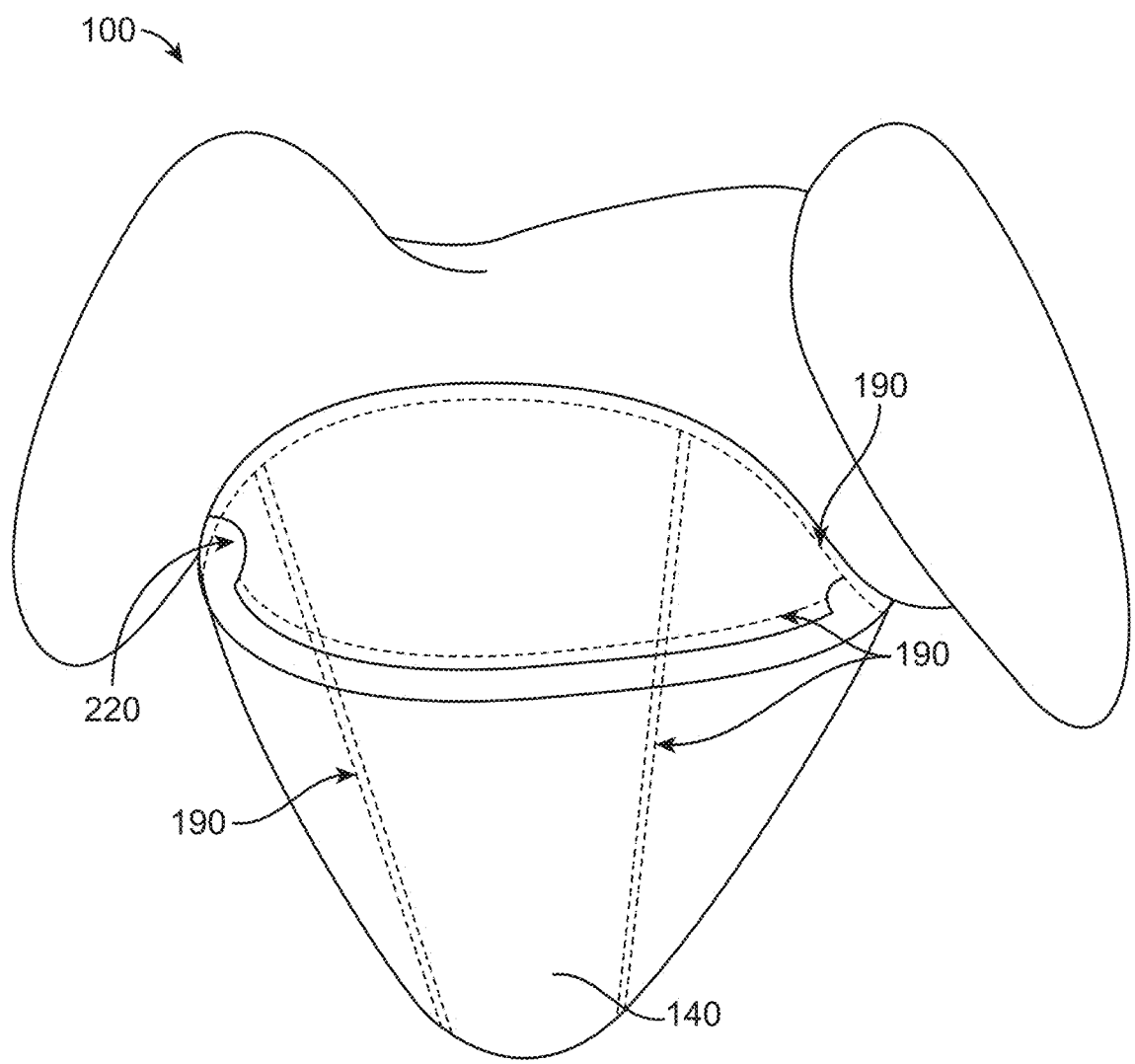
FIG. 15 illustrates a container comprising a flap to prevent splash onto a user, in accordance with some embodiments.

In some cases, the container 140 may comprise a flap to prevent splash onto a user (e.g. a physician). FIG. 15 shows an example of container 140 comprising a flap 220. In some cases, the flap may be deployable. The container may be configured having an inner sterile portion and an external non-sterile portion to protect the physician from splash. The flap may comprise a non-sterile portion that extends outside of the surgical drape. In some cases, the flap 220 may have a self-supporting semi-cylindrical form. In some cases, one or more stiffening elements 190 can be used to support a structural configuration of the container and/or the flap. In some embodiments, one or more of the stiffening elements 190 can be adjustable in position to prevent splash onto the physician, for example by raising the flap higher.

The stiffening elements 190 can extend in directions transverse to each other. For example, the stiffening elements 190 may extend circumferentially and longitudinally along the container 140. The stiffening elements may comprise a bendable material such as a thin wire, for example, or any stiffing structure or element as described herein.

Figure 16:
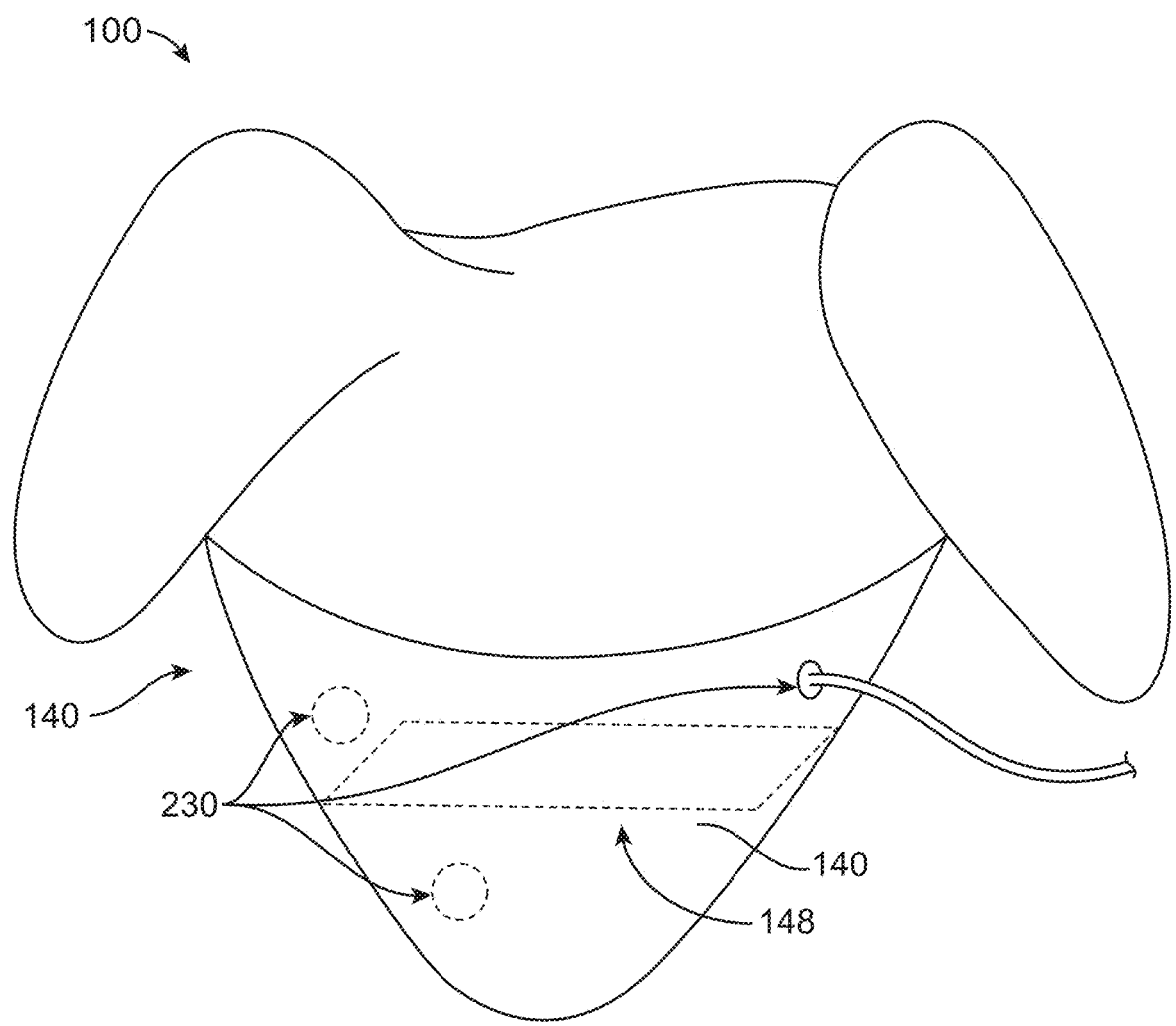
FIG. 16 illustrates a container comprising one or more ports for accepting fluids from an irrigation or aspiration pump, or from a drain line above or below a screen, in accordance with some embodiments.

In some cases, the container 140 may comprise one or more ports 230 for accepting fluid from an irrigation or aspiration pump, or from a drain line above or below a screen 148. FIG. 16 shows an example of the ports 230 in accordance with some embodiments. The ports may comprise an opening, an aperture, a fenestration, a connecting feature, sealing flange, and the like.

Figure 17:
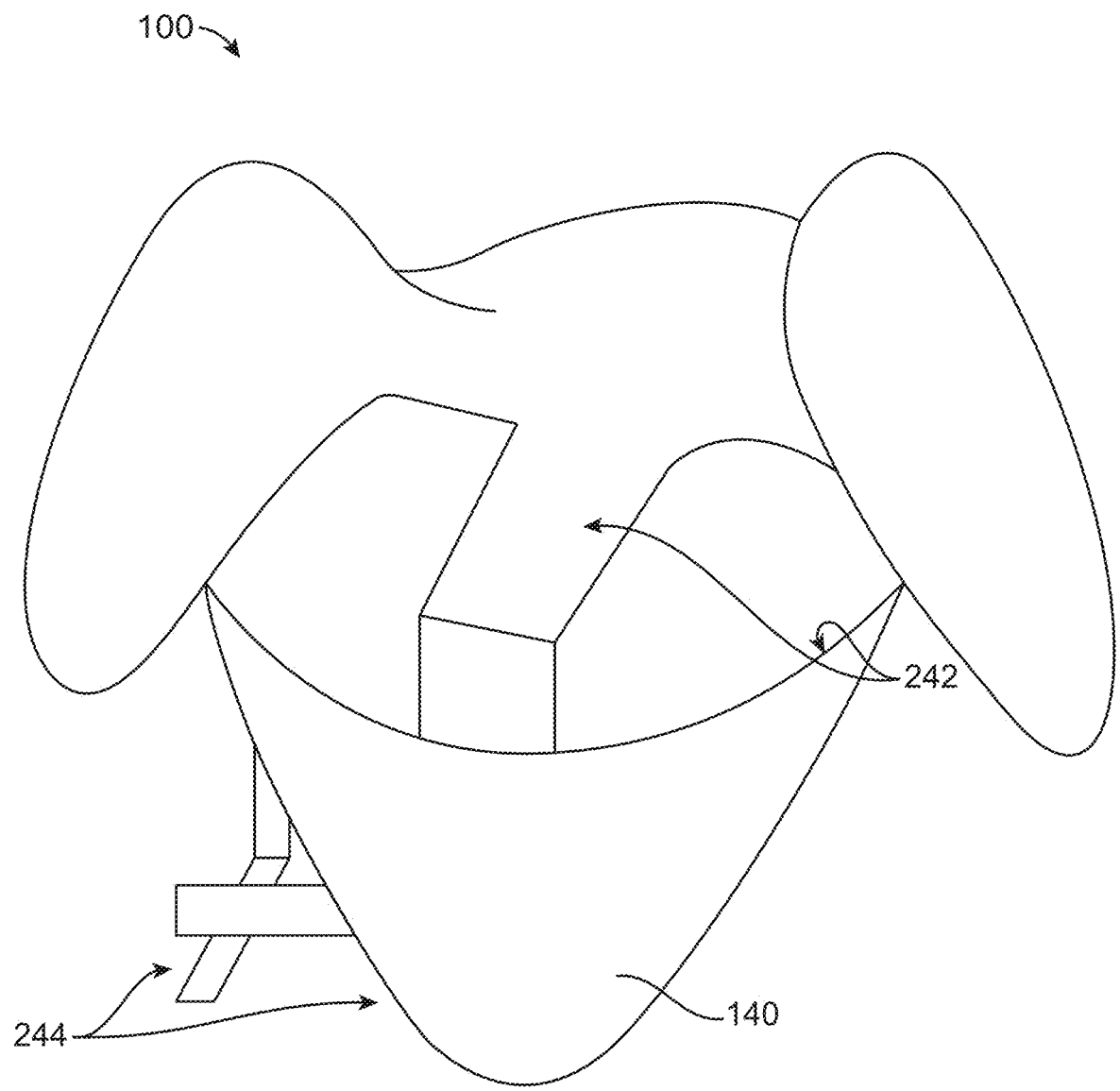
FIG. 17 illustrates a container comprising extruded portions that define an inner sterile surface and an external non-sterile surface, in accordance with some embodiments.

In some embodiments, the container 140 may comprise one or more extruded portions extending from the container 140. One or more of the extruded portions may have a 'tented' shape. Referring to FIG. 17, the extruded portions may help to define an inner sterile surface 242 and an external non-sterile surface 244. The external non-sterile surface 244 may provide a working space for placement of a support structure comprising the surgical arm (e.g. articulating arm 14). The external non-sterile surface permits an ungloved hand to access a sterile space defined within the inner sterile surface 242 for manipulation of the transrectal device.

Figure 18:
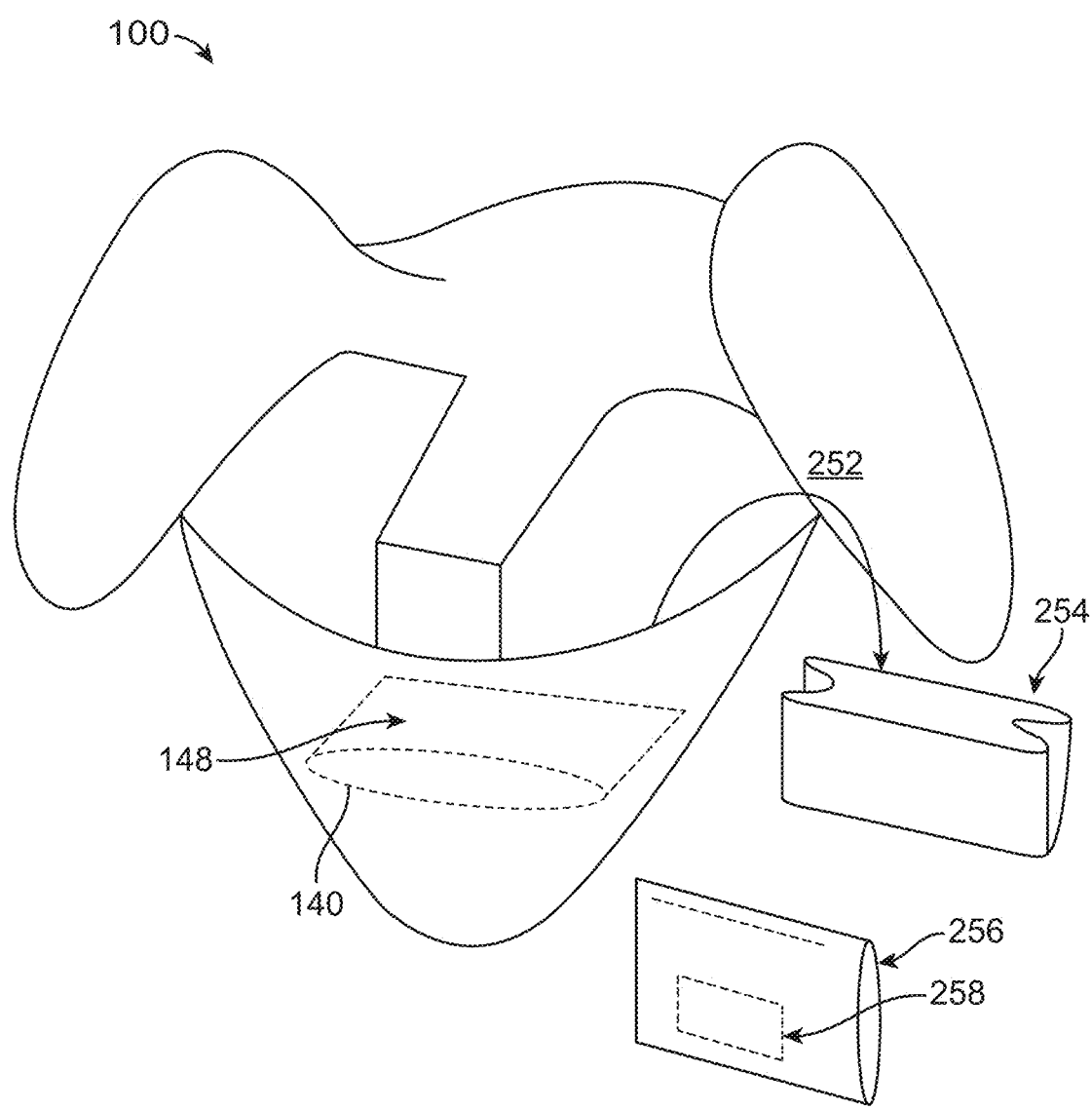
FIG. 18 illustrates a container comprising a detachable screen in accordance with some embodiments.

In some embodiments, the container may comprise a detachable screen 148, for example as shown in FIG. 18. The screen may be detachably coupled to an inner lower portion of the container 140. The screen may be detached 252 from the container, and can be folded up 254 and sealed 256 for collection and transportation of tissue or solid samples (for subsequent analysis or disposal). The screen may comprise a hole that is sized or shaped to permit capture of clots or intact tissue. The screen may comprise a material that is impervious to fluids, that is provided along edges or sides of the screen. In some cases, the screen may comprise a closure element for securing samples for storage or transport (that enables the screen to be sealed 256). The closure element may comprise a zipper, a zip-lock, an adhesive seal, a draw-string, a clip, or an elastic or conformable wire. In some cases, the screen may comprise a translucent region that is compatible with imaging modalities for tissue analysis. The screen may be removable from the container along the edges or sides of the screen to permit visualization through the translucent region. In some cases, the screen may comprise an area 258 for displaying information about the patient. The area 258 can be configured to receive thereon a preprinted label containing the information about the patient. Additionally or optionally, the area 258 can be configured to permit a user to write thereon. In some cases, the area 258 may comprise a plurality of sub-areas for displaying preprinted information or clinician notes.

Figure 19:
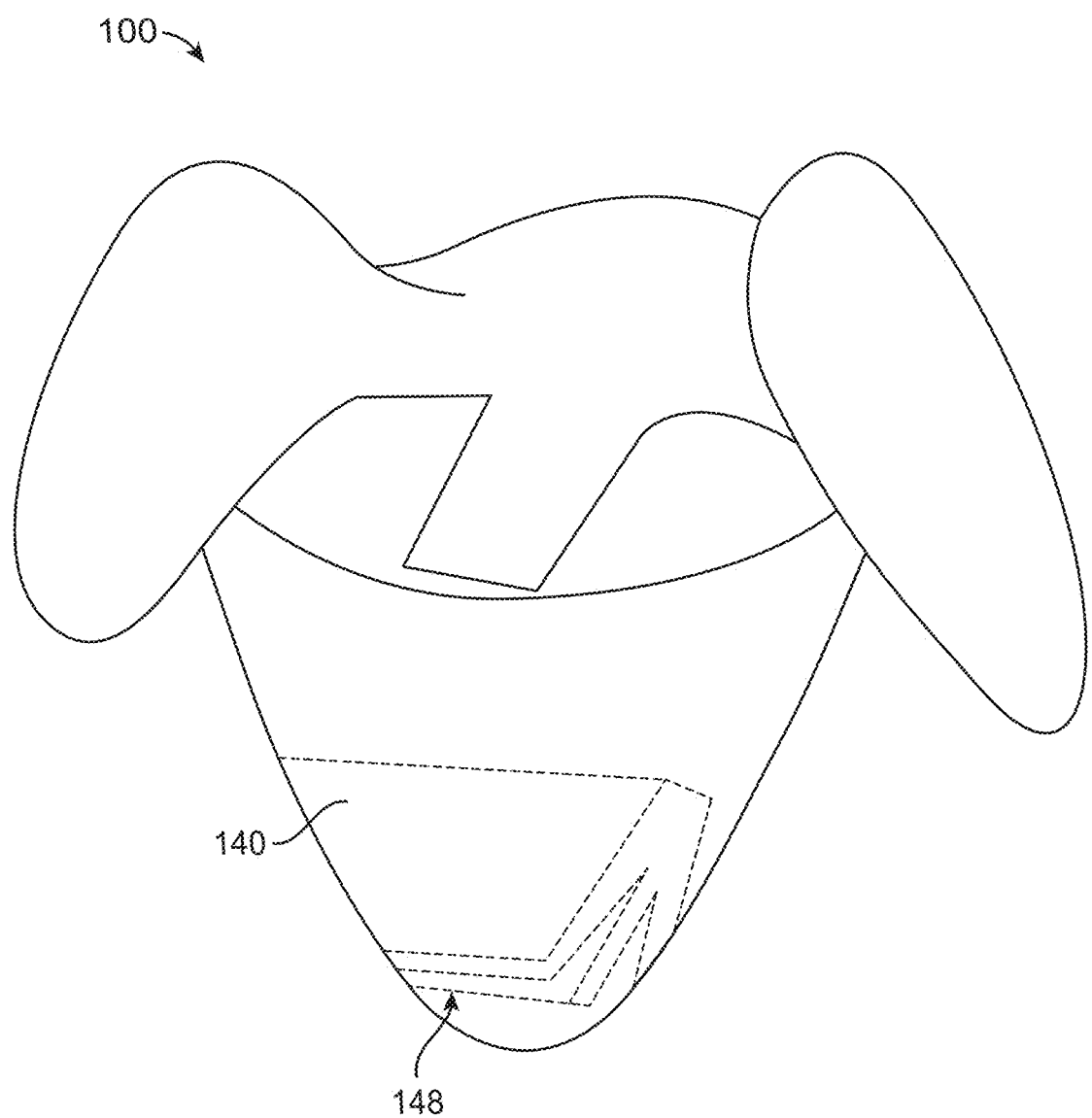
FIG. 19 illustrates a screen that can be configured to fold with collapse of the container in accordance with some embodiments.

Referring to FIG. 19, the screen can be configured to fold with collapse of the container 240. The folding of the screen can be configured to permit airflow to a drain/suction port. The screen can be configured to fold in an interleaved manner.

Figure 20:
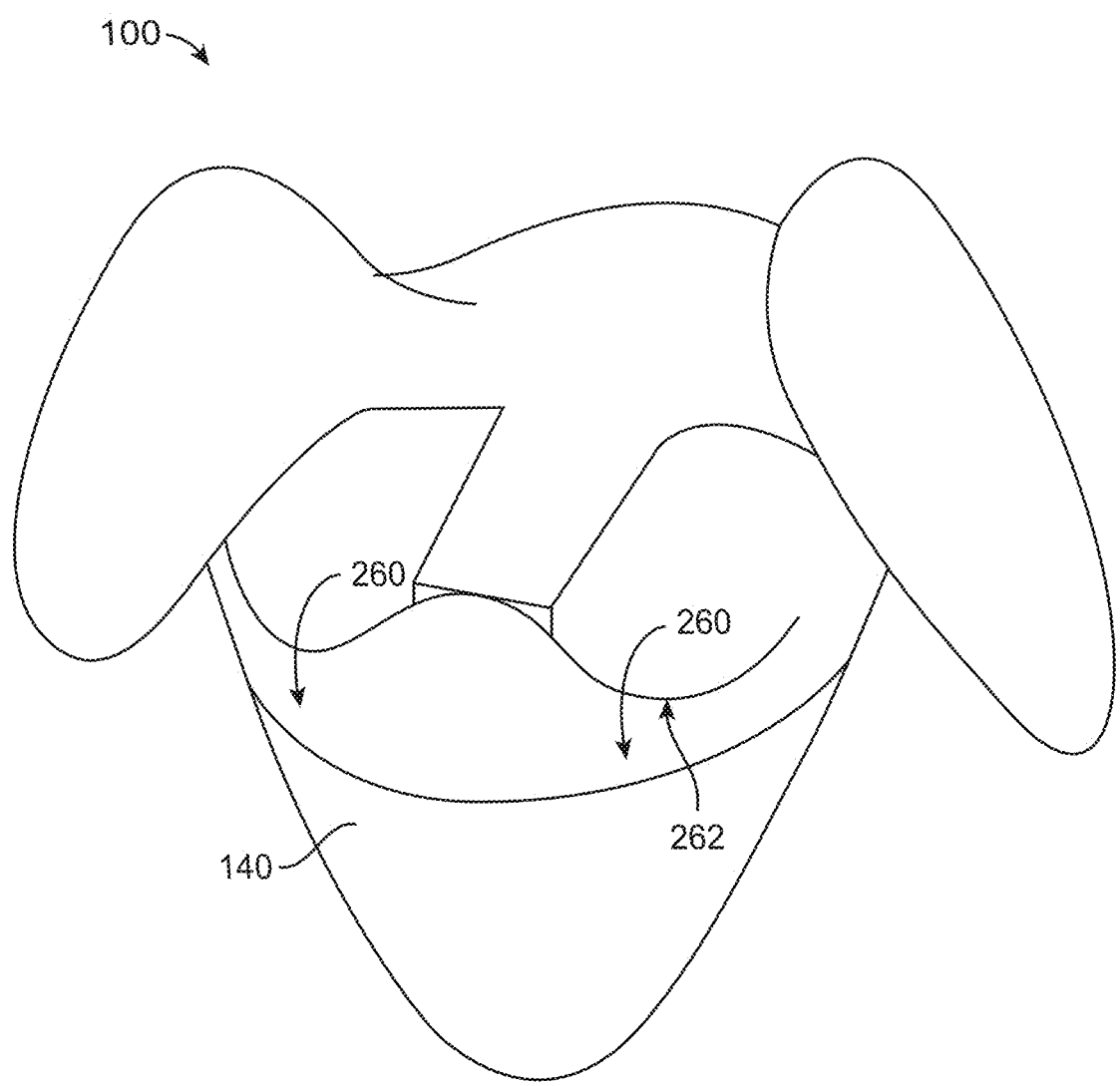
FIG. 20 illustrates a canopy portion designed such that fluid is conducted to flow downwards toward the container when the canopy portion is in an inverted configuration, in accordance with some embodiments.

Referring to FIG. 20, the canopy portion 111 may be designed such that fluid is conducted to flow downwards 260 toward the container 140 when the canopy portion is in an inverted configuration. The inverted configuration can prevent fluids from accumulating or pooling on the canopy portion 111 instead of flowing into the container 140. The inverted configuration may comprise one or more sloping surfaces that aid the fluid to flow downward toward the container. The canopy portion 111 may be shaped and/or sized 262 such that the canopy portion does not sag and collect fluids under weight of the fluids.

In some embodiments, the surgical drape 100 may comprise one or more labels as described herein. The labels may comprise instructions for using the drape, and information on one or more of the following: (a) location of one or more access port holes, (b) location of one or more perforations, (c) location of one or more attachment points, (d) areas at which sections of the drape can be detached, (e) placement of the drape onto the patient, (f) location of the drape relative to an operating table, (g) attachment of the drape to the operating table, (h) location of the drape relative to one or more support structures proximal to the operating table, or (i) attachment of the drape to the one or more support structures.

In some embodiments, the surgical drape 100 may comprise excess material in at least the first portion 110 or the second portion 130 to permit a non-sterile hand of the user (e.g. a physician) from a non-sterile working space outside of the drape to access and manipulate the probe 10 comprising the transrectal device or the surgical arm 14 without contaminating a sterile field underneath the drape. The canopy portion 111 can be configured to permit the user to manipulate the surgical arm 14 that supports the transrectal device.

Figure 21:
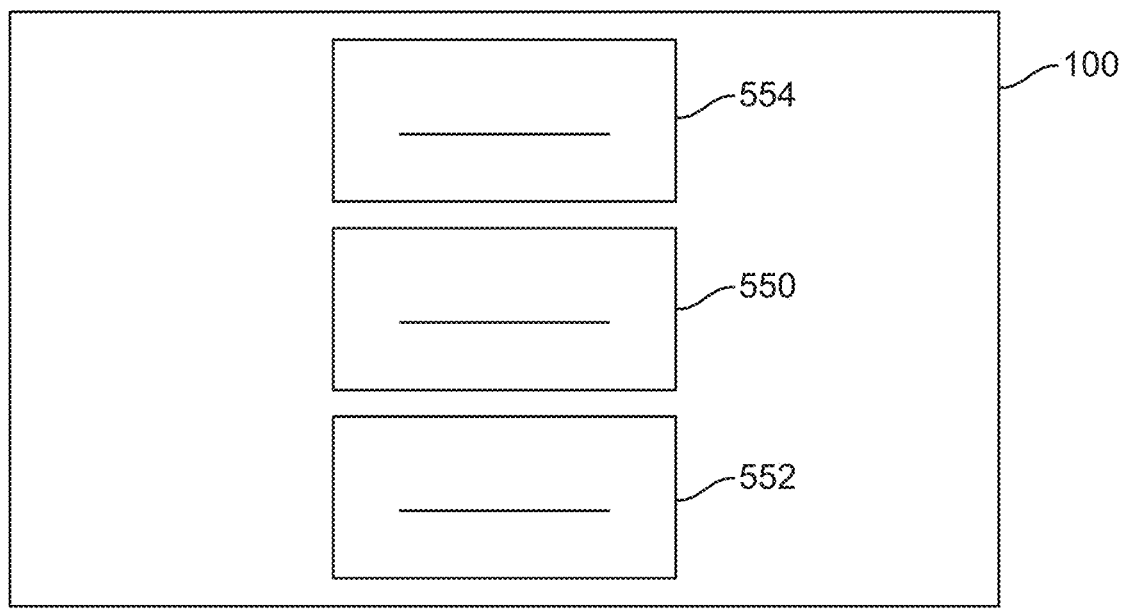
FIG. 21 shows a surgical drape comprising labels, in accordance with some embodiments.

FIG. 21 shows a surgical drape 100 comprising one or more labels. The labels may comprise a first label 550, a second label 552 and a third label 554, for example. Additional labels or fewer labels may be provided with the drape 100. The labels may comprise any of the labels as described herein. The labels may be affixed to the drape, so as to identify structures of interest on the drape, such as access port holes, perforations, attachment points, areas of the drape that can be detached as sections, placement of the drape on the patient, location of the drape relative to the patient and the operating table, location of the drape relative to support structures, and attachment of the drape to support structures. The one or more labels may comprise instructions for use for the drape 100, and the instructions for use can be attached to the drape or provided separately. The instructions for use can be affixed to the drape on a sterile side of the drape, in order to maintain sterility while one or more instructions is referred to by a user. The one or more instructions may comprise an arrow or other indicia to identify portions of the drape that may be of interest to a user. For example, an arrow or a circle can identify the opening on the drape through which a penis of the patient is passed from the non-sterile side of the drape to the sterile side. One or more perforations can be identified with an indicium associated with the label to identify the perforations.

Figure 22A:
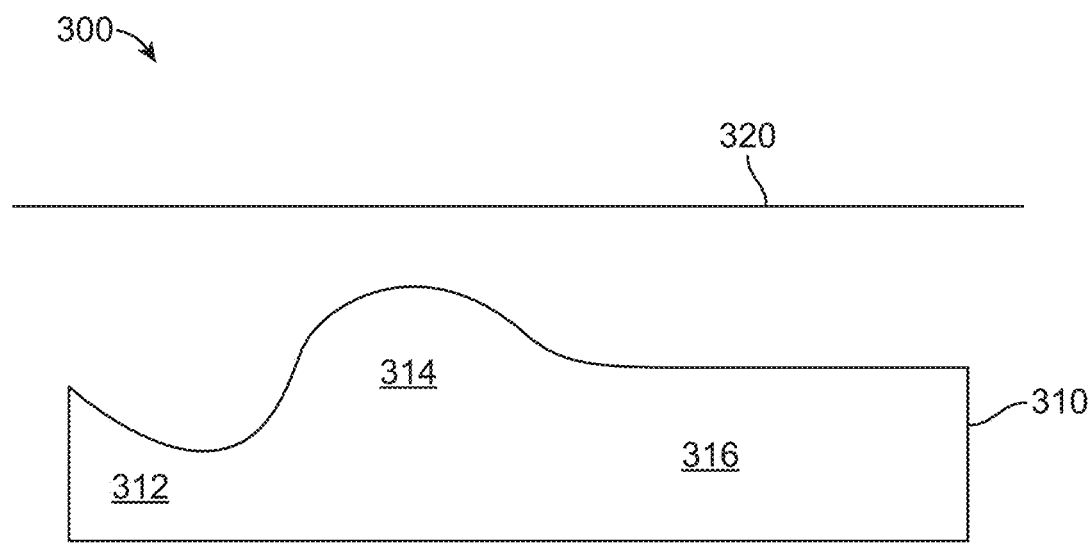
FIG. 22A shows thermoforming with a mold and sheet material, in accordance with some embodiments.

FIG. 22A shows a method 300 of thermoforming the cover 100 as described herein with a mold 310 and sheet material 320. The mold may comprise container forming portion 312 comprising a curved surface, such as a concave surface to contact sheet material 320, so as to define container portion 140 of drape 100. The mold may comprise a canopy forming portion 314 comprising a curved surface, such as a convex surface to contact sheet material 320. The canopy forming portion may comprise inverted portions comprising opposite curvature to facilitate drainage as described herein, for example inverted portions adjacent, near, or within protrusion of canopy forming portion 314. The mold may comprise torso forming portion 316, so as to define the torso portion of the drape. The mold may comprise additional structures corresponding to a patient placed in stirrups for a urological procedure as described herein, for example, structures corresponding to bent legs of a patient.

Figure 22B:
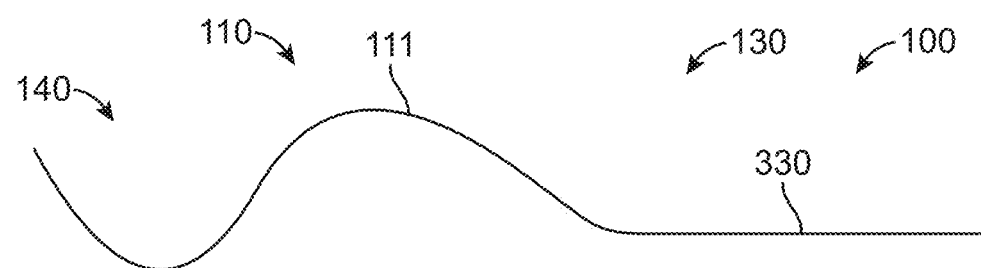
FIG. 22B shows a surgical drape thermoformed over a mold, in accordance with some embodiments.

FIG. 22B shows a surgical drape 100 thermoformed over mold 310, so as to define the three-dimensional shape profile of thermoformed surgical drape 330. Thermoformed surgical drape 330 may comprise any of the structures of surgical drape 100 as described herein. For example, the thermoformed drape 330 may comprise container portion 140 as described herein, first portion 110 comprising the canopy portion as described herein, and second portion 130 comprising the torso portion as described herein.

The thermoformed drape 330 may comprise one or more stiffing structures as described herein, and the stiffening structures may comprise stiffening structures sandwiched between a plurality of layers of thermoformed sheet material, for example. The stiffening structures can be placed on a first thermoformed layer of the drape, and a second layer placed over the stiffening structures so as to sandwich the stiffening structure between the layers, and the layers can bond together as part of the thermoforming process. Alternatively, or in combination, actuators can be sandwiched between thermoformed layers of the drape, so as to automatically expand and extend the drape from a compact packaged configuration for sterile storage to an expanded and extended configuration for use on a patient. The sheet material may comprise any biocompatible barrier material impermeable to bodily fluids, and can be thermoformed on the mold as will be understood by one of ordinary skill in the art.

The method 300 for thermoforming the drape 100 may comprise one or more steps as follows: 1) receive sheet material to thermoform the mold; 2) manufacture the mold with the three-dimensional shape profile; place the sheet material on the mold; thermoform the sheet material to the shape of the mold; place appropriate structures on the thermoformed sheet of material at appropriate positions and orientations, e.g. stiffening structures; thermoform a second sheet of material on the mold so as to bond the first sheet to the second sheet with the stiffening structures therebetween; remove the thermoformed surgical drape 330 from mold 310; place the thermoformed surgical drape in a package or wrap the thermoformed drape within a packaging portion of the drape, in a compact storage configuration; and sterilize the thermoformed drape.

Although method 300 of thermoforming a surgical drape is described herein in accordance with an embodiment, a person of ordinary skill in the art will recognize many variations and adaptations. Some of the steps may be removed or repeated, and the steps may be performed in a different order, for example.

Figure 23A:
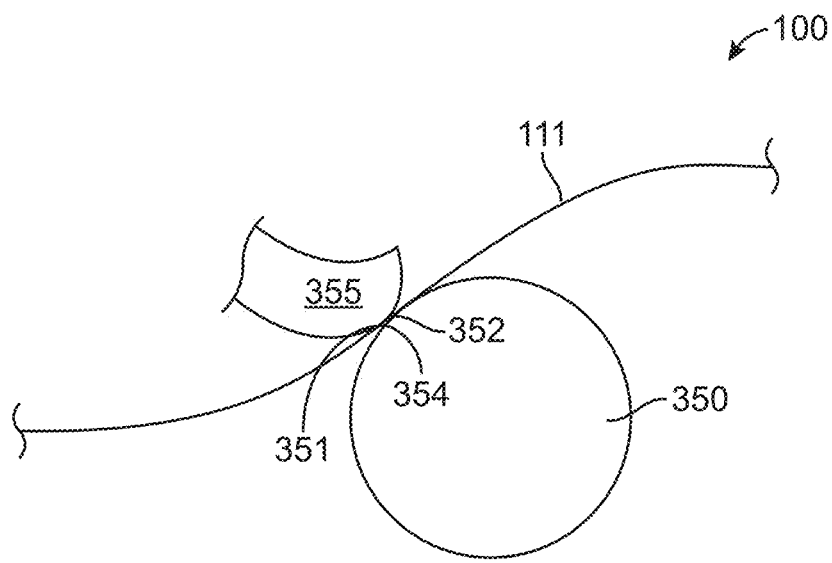
FIG. 23A shows a user manipulating a transrectal device through a canopy portion of a surgical drape and a corresponding first position of a proximal portion of the transrectal device, in accordance with some embodiments.

FIG. 23A shows a user manipulating a transrectal device through canopy portion 111 of surgical drape 100 and a corresponding first position 351 of an engaged portion 352 of the proximal portion 350 of the transrectal device comprising probe 10 as described herein. The engaged portion of the transrectal device may comprise a portion of actuator 117 as described herein, for example a knob of the actuator. The knob may comprise of a portion of actuator 117 and may comprise an engaged portion 352 of the transrectal device. An engaged portion 354 of canopy portion 111 is located between the engaged portion 352 of the proximal portion 350 of the transrectal device, and an engaged portion 355 of the hand of a user such as a finger or thumb of the user. The engaged portion 355 of the hand of the user is coupled to the engaged portion 354 of the canopy, with the engaged portion 354 of the canopy of the drape located between the engaged portion 355 of the hand of the user and the engaged portion 352 of the proximal portion 350 of the transrectal device. The coupling allows the canopy to move with the hand and the canopy portion with a low resistance to movement, such that the proximal portion of the transrectal device appears to move freely with the hand of the user with the proximal portion of the transrectal device located within the canopy.

Figure 23B:
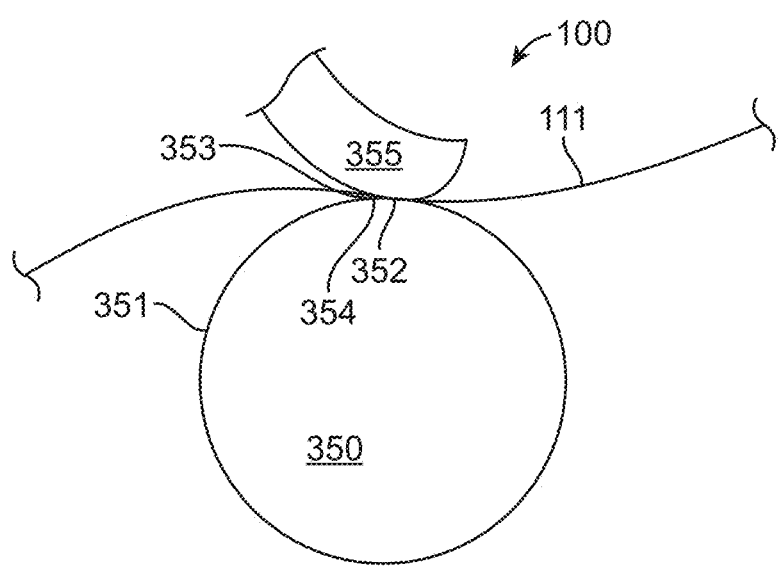
FIG. 23B shows the user manipulating the proximal portion of the transrectal device of FIG. 23A and a corresponding second position of the proximal portion of the transrectal device, in accordance with some embodiments.

FIG. 23B shows the user manipulating the proximal portion 350 of the transrectal device of FIG. 23A and a corresponding second position of the proximal portion of the transrectal device. The engaged portion 352 of the proximal portion of the transrectal device has been moved to a second position 353 with the engaged portion 355 of the hand of the user and the engaged portion 354 of the canopy portion 111. At the second position 353 the canopy has been moved from the first position 351 to the second position 353 with a small substantially imperceptible about of force. The movement of the canopy typically provides a resistance to movement that is less than the amount of force required to move the proximal portion 350 of the transrectal device. The amount of force to move the engaged canopy portion can be less than one tenth (1/10), for example less than one hundredth (1/100) of the amount of force used to move the engaged portion 352 of the proximal portion of the transrectal device.

Figure 23C:
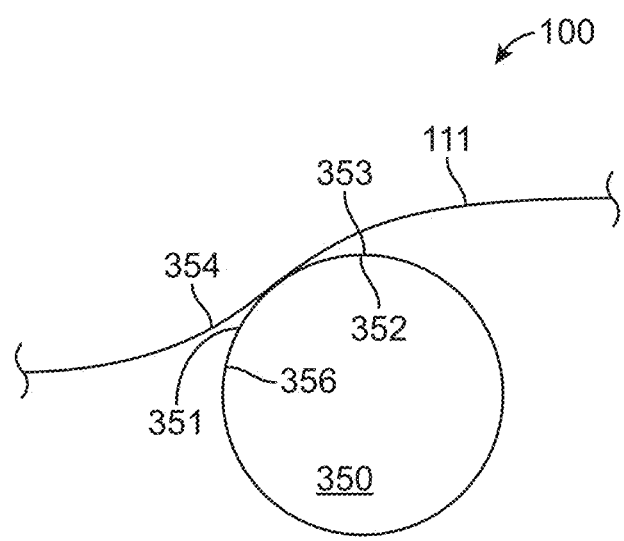
FIG. 23C shows return of a portion of the canopy portion toward the first position of FIG. 23A, in accordance with some embodiments.

FIG. 23C shows return of the engaged portion 354 of the canopy portion toward the first position 351 of the engaged portion as shown in FIG. 23A. This return of the engaged portion of the canopy portion allows the user to release proximal portion of the transrectal device and engage the proximal portion of the transrectal device at a new location 356, so as to allow the user to move the proximal portion of the transrectal device again, while encountering substantially imperceptible amounts of resistance from an engaged portion of the canopy as described herein. The amount of return can be a distance within a range from about 1 mm to about 100 mm, for example within a range from about 1 mm to about 25 mm.

The proximal portion 350 of the transrectal device may comprise a proximal portion of any transrectal device as described herein. In some embodiments, the proximal portion of the transrectal device comprises a knob of the transrectal device that is coupled to a probe so as to allow movement of the probe of the transrectal device. For example, the probe of the transrectal device can be mounted on a carriage coupled to the knob, such that the probe can be advanced distally and retracted proximally with rotation of the knob. In some embodiments, the transrectal device comprises an ultrasound imaging probe as described in PCT Application PCT/US2013/028441, filed on Feb. 28, 2013, entitled "AUTOMATED IMAGE-GUIDED TISSUE RESECTION AND TREATMENT", published as WO/2013/130895, the entire disclosure of which is incorporated herein by reference. A transrectal ultrasound image can be shown on a display visible to a user, such that the transrectal ultrasound probe can be adjusted through the canopy portion with return of the engaged canopy portion as described herein. The transrectal device may comprise an input output ("I/O") device as described herein so as to allow computer control of the position of the transrectal device, and the engaged portion of the canopy can return as described herein so as to facilitate movement of the engaged portion of the hand of the user and interaction with the I/O device.

The substantially imperceptible resistance to force provided by the canopy portion 111 when the engaged portion 354 moves from the first position 351 to the second position 353 stores potential energy in the canopy portion and in some embodiments additional portions of the drape 100. This potential energy is released at least partially when the engaged portion 354 of the canopy 111 is released by the hand of the user, and the engaged portion 354 returns from the second position 353 toward the first position 351.

Figure 24A:
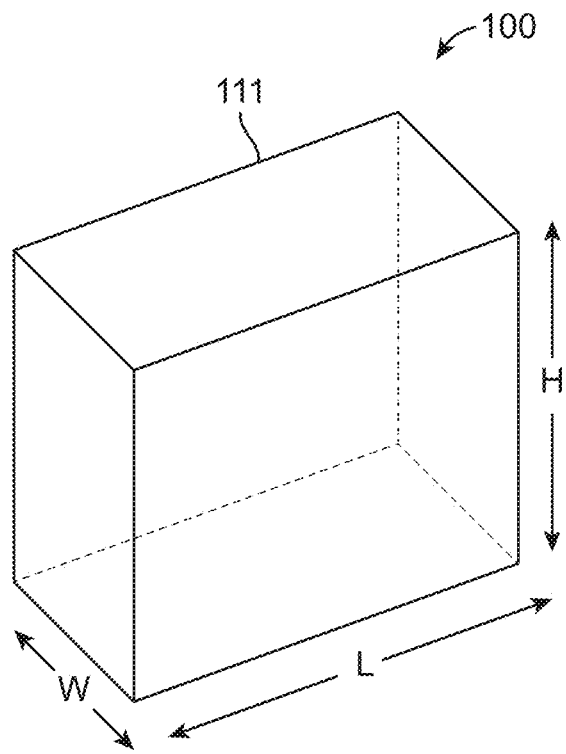
FIG. 24A shows a full volume of a canopy portion in an extended configuration.

FIG. 24A shows a full volume of a canopy portion 111 in an extended configuration. In the extended configuration, the sheets of the canopy have been extended to substantially remove slack and folds. While this can be achieved in many ways, in some embodiments a lower perimeter of the canopy portion 111 can be supported and the canopy inflated with a gas such as air to extend the canopy into the extended configuration to determine a volume of the canopy. The canopy portion 111 may comprise a length L, a width W and a height H for embodiments in which the canopy comprises a rectangular protrusion. Each of these dimensions may be defined by distances between corresponding corners of the canopy portions. The full volume of the canopy portion corresponds to the length, width and height and may be calculated by the known formulas. In some embodiments, the protruding canopy may comprise one or more substantially straight sides, and a comprise a partially trapezoidal shape, for example. In some embodiments the canopy portion comprises a curved surface sized and shaped to receive at least a proximal portion of the transrectal device. The curved surface when extended substantially without slack or folds defines the volume of the canopy portion. The canopy portion 111 may comprise a combination of substantially flat surface and curved surfaces, for example. In some embodiments, the lower perimeter of the canopy portion is supported and the canopy portion inflated with a gas to expand the canopy portion to the fully extended configuration in order to determine to the full volume. The amount of gas such as air within the fully expanded canopy portion can be measured by deflating the canopy portion to a fully deflated and compact configuration and measuring the amount of gas released. The amount of gas released by be measured by any number of ways known to a person of ordinary skill in the art.

Figure 24B:
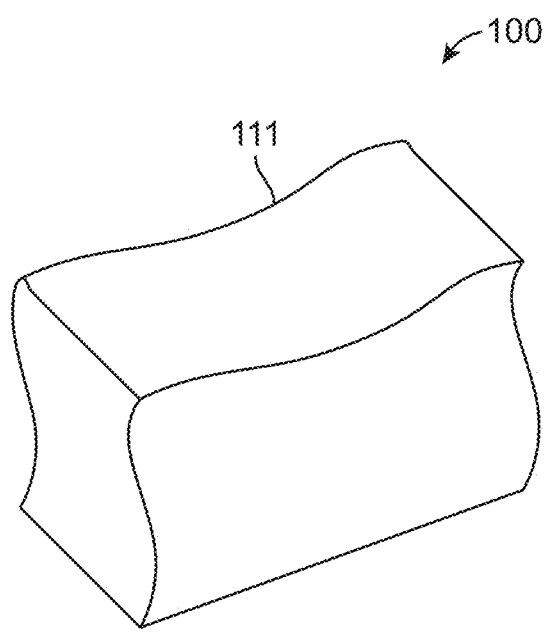
FIG. 24B shows a decreased volume of the canopy portion of FIG. 24A in a partially collapsed configuration, in accordance with some embodiments.

FIG. 24B shows a decreased volume of the canopy portion 111 of FIG. 24A in a partially collapsed free standing configuration. The height H is decreased in the free standing configuration, and the barrier sheet material may comprise folds so as to decrease the height H by at least about 10%, for example. The length L and with width W defined by distances between corners of the canopy may be similarly decreased, e.g. by at least about 10%. In some embodiments, the volume of the canopy decreases by an amount within a range from about 10% to 90% between the fully extended configuration and the partially collapsed free standing configuration. The canopy may comprise at least some weight, such that the volume of the canopy decreases in a partially collapsed free standing configuration as compared with the volume of the canopy in the fully extended expanded configuration. The weight and stiffness of the barrier material of the canopy can be configured to provide the partial collapse of the canopy. A heavier (e.g. thicker) less stiff barrier material will collapse more than a lighter (e.g. thinner) barrier material comprising similar stiffness. A stiffer barrier material may collapse less.

A lower perimeter of the canopy can be supported, and the volume of the partially collapsed canopy determined, for example based on an amount of gas released when the canopy is compressed from the free standing partially collapsed configuration to the fully collapsed configuration. In some embodiments, the canopy barrier material inhibits the flow of air from the canopy. The seals of the canopy, if present, may comprises air tight seals to maintain the sterile field above the canopy. The barrier material of the canopy 111 may comprise a Young's modulus, a thickness, and a density configured to provide the partial collapse of the canopy in the free-standing configuration as described herein.

The amount of return of the canopy portion as described herein can be related to the Young's modulus, the thickness, the density of the barrier material and the volume of the full volume of the canopy portion in relation to the amount of movement of the proximal portion of the transrectal device. A person of ordinary skill in the art can determine suitable configurations of materials as described herein to configure the canopy with partial return during manipulation of the transrectal device, and partial collapse in the free standing configuration as described herein.

Figure 25A:
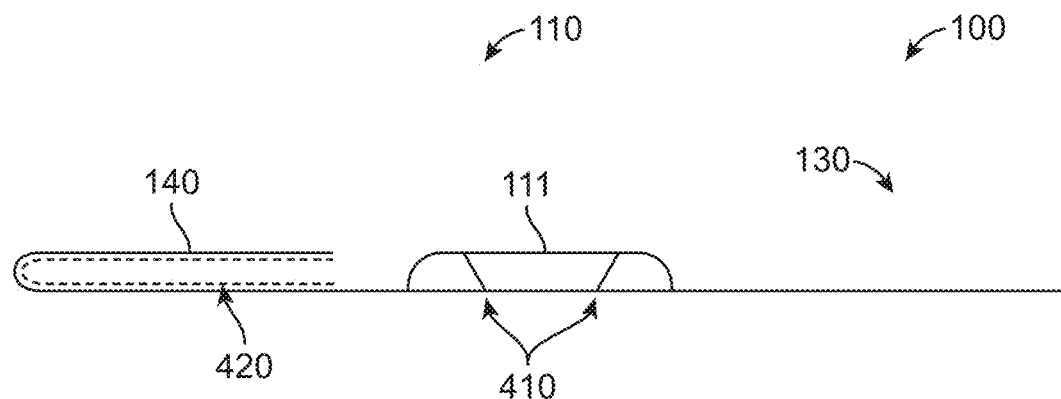
FIG. 25A shows a surgical drape coupled to an actuation element in a compact configuration in a side profile view, in accordance with some embodiments.

FIG. 25A shows a surgical drape 100 coupled to an actuation element in a compact configuration in a side profile view.

Figure 25B:
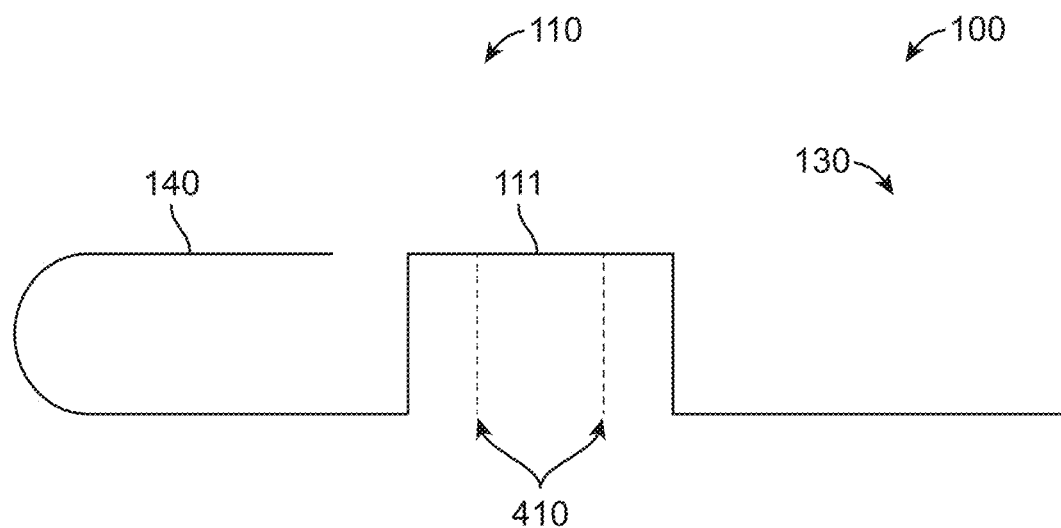
FIG. 25B shows the surgical drape of FIG. 25A in an extended profile configuration in a side profile view, in accordance with some embodiments.

FIG. 25B shows the surgical drape 100 of FIG. 25A in an extended profile configuration in a side profile view.

Figure 25C:
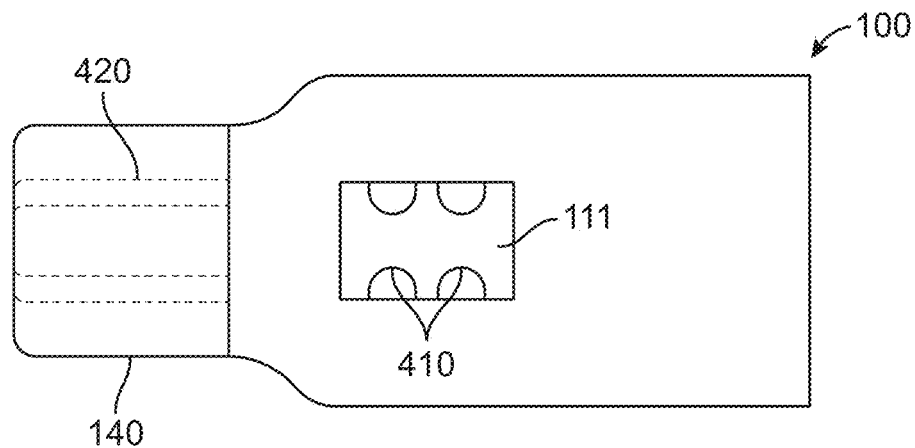
FIG. 25C shows the surgical drape of FIG. 25A in the compact profile configuration in a top profile view, in accordance with some embodiments.

FIG. 25C shows the surgical drape of FIG. 25A in the compact profile configuration in a top profile view.

The surgical drape may comprise actuation elements in any and any location of the drape, so as to expand the drape from a compact configuration as described herein, e.g. as shown in FIG. 25A, to an at least partially extended and at least partially expanded configuration as shown in FIG. 25C. The first portion 110 of the drape 100 comprising canopy portion 111 may comprise one or more actuation elements 410 in order to at least partially extend and expand the canopy portion. The actuation elements may comprise a shape memory material, such as spring steel or thermoformed plastic, configured to extend and expand the canopy portion to an increased internal volume. In the compact configuration shown in FIG. 25C, the actuation elements may comprise a bent configuration and straighten in the expanded profile configuration in FIG. 25B. The second portion 130 comprising the portion of drape 100 configured to at least partially cover the torso of the patient comprises actuation elements in some embodiments, either alternatively or in combination with actuation elements 410 or one or more action elements 420.

The container portion 140 of the drape may comprise one or more actuation elements 420 configured to expand the container portion form an initial compact configuration to an expanded configuration to receive fluids as described herein.

Although the compact configuration of FIG. 25A is shown with the drape extended along a length of the drape, actuation elements can be provided that extend at least partially along the length of drape, so as to at least partially unroll the drape to the configuration shown in FIG. 25A. For example, one or more actuation elements 420 can extend from the container portion 140 through the first portion 110 comprising canopy portion 111 and at least partially along the second portion 130 configured to at least partially cover the torso. The drape can be initially provided in a rolled configuration in the sterile package, such that the drape unrolls in response to actuation elements 410 and 420 to expand the drape from a compact configuration to the extended profile configuration as shown in FIG. 25B. Although reference is made to a rolled configuration, the surgical drape 100 can be configured to expand from a compact folded configuration to the extended profile configuration.

The surgical drape shown in FIGS. 25A to 25C can be configured with stiffening elements either alternatively to the actuation elements, or in combination with the stiffening elements. The stiffening elements may comprise any stiffening element or structure as described herein and may comprise metal extensions such as wire or pleats, for example. The metal extensions may comprise a deformable material, and a cross-sectional thickness and length suitable for allowing the drape to be shaped as desired by the user. The wire may comprise a suitable diameter to allow the drape to be shaped to as desired by the user. The extensions can be placed at one or more locations of the drape, such the canopy portion of the container portion, and combinations thereof.

The one or more actuation elements can be configured in many ways. In some embodiments, the actuation element comprises one or more spring elements, and optionally the one or more spring elements comprises spring steel.

The container can be configured to receive, collect and store waste including bodily fluids, surgical-related fluids, tissue or debris generated during the surgical treatment. The container can be configured to receive, collect and store waste including bodily fluids, surgical-related fluids, tissue or debris generated during the surgical treatment as described herein. In some embodiments, the container portion 140 comprises a volume within a range from about 1000 cm³ to about 70,000 cm³ in the expanded deployed configuration and optionally the volume is within a range from about 1000 cm³ to about 10,000 cm³.

In some embodiments, at least one of a first portion comprising the canopy portion or a second portion comprising the torso portion is operably coupled to an actuation element configured to deploy one or more sections of the surgical drape from a compact configuration to an extended configuration.

In some embodiments, the compact configuration comprises a substantially two-dimensional shape, and the extended configuration comprises a substantially three-dimensional shape.

In some embodiments, the surgical drape is in the compact configuration when the surgical drape is not in use prior to deployment, and deployed to the extended configuration prior to or during use of the surgical drape for the surgical treatment of the patient.

Figure 26:
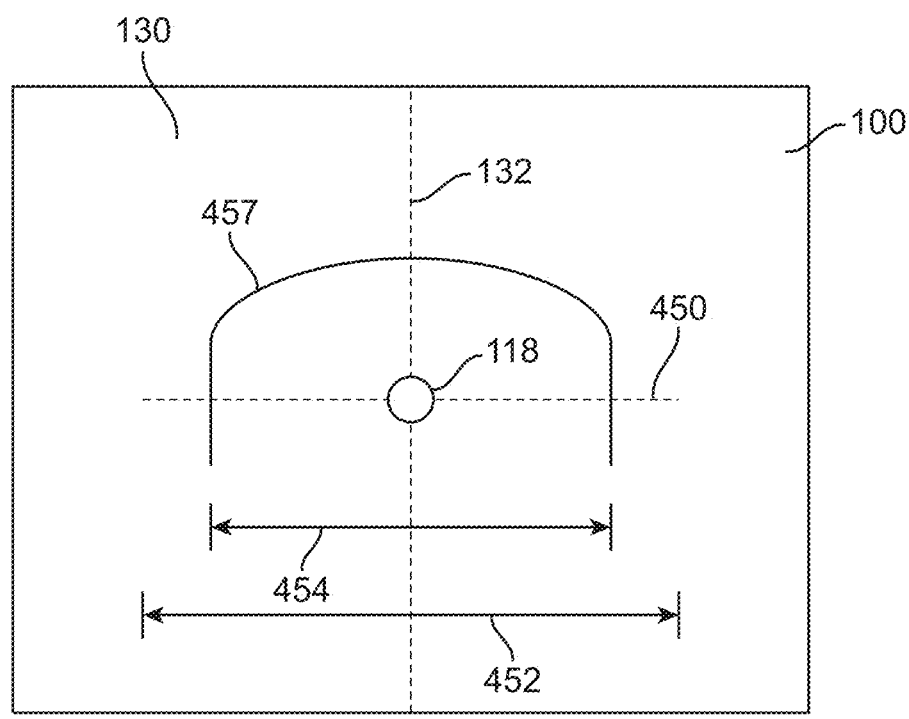
FIG. 26 shows an opening sized to receive a surgical urological probe and perforations extending in a first direction corresponding to inferior and superior directions of a patent and perforations extending in second direction transverse to the first direction to allow the surgical drape to be removed around a base of a tensioning device coupled to a patient with a catheter extending along the urethra of the patient, in accordance with some embodiments.

FIG. 26 shows an opening sized to receive a surgical urological probe and 132 perforations extending in a first direction corresponding to inferior and superior directions of a patent and perforations 450 extending in second direction transverse to the first direction to allow the surgical drape to be removed around a base 457 of a tensioning device coupled to a patient with a catheter extending along the urethra of the patient. Examples of a base and tensioning devices are described in PCT application PCT/US2017/023062, filed on Mar. 17, 2017, entitled "MINIMALLY INVASIVE METHODS AND SYSTEMS FOR HEMOSTASIS IN A BLEEDING CLOSED TISSUE VOLUME", published as WO/2017/161331, the entire disclosure of which is incorporated herein by reference. The base may comprise a maximum dimension 454 across the base. The perforation 450 extending in the second direction may extend a distance 452 greater than maximum dimension 454 across the base, so as to facilitate removal of the surgical drape when the base and tensioning device have been coupled to the patient. The maximum dimension across the base can be within a range from about 2.5 cm to about 30 cm, for example within a range from about 3 cm to about 20 cm. The distance 452 may comprise a distance within a range from about 2.5 cm to about 60 cm, for example within a range from about 3 cm to about 40 cm.

Although reference is made to perforations, the surgical drape can be configured in many ways similar to perforations 132 and 450. In some embodiments, a second portion comprising the torso portion comprises a weakened material extending a direction corresponding to a direction along an inferior superior direction of the patent, e.g. along a midline. The second portion can be configured to assist removal of the surgical drape by allowing the second portion to separate along the weakened material. In some embodiments, the weakened material comprises one or more of perforations, thinned material relative to adjacent unweakened material, thermally or chemically weakened material or stressed material along the midline, or at any angle or offset to the midline, so as to extend a generally along a generally inferior or superior aspect of the patent. In some embodiments, a second weakened material extends in a second direction transverse to the midline in order to facilitate removal of the surgical drape around a base of the traction device coupled to the patient with a catheter extending along a urethra of the patient. The second weakened material extending in the second direction can be weakened similarly to the weakened material extending in the first direction, and may comprise perforations extending in the second direction, for example.

In some embodiments, the perforations allow insertion or access of a catheter to be inserted into a urethra of the patient. The catheter may comprise a suprapubic catheter to drain urine from a bladder of the patient, for example.

Figure 27:
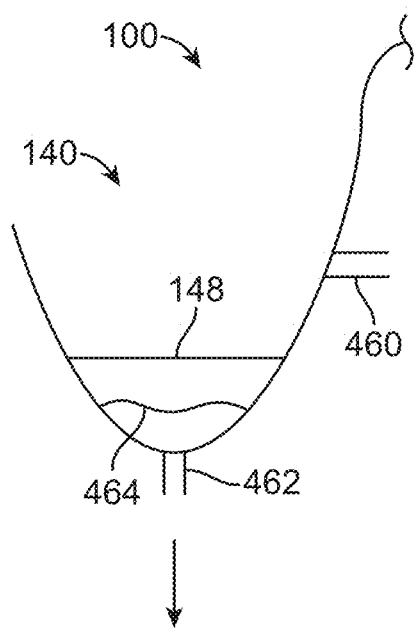
FIG. 27 shows a container portion of a surgical drape with a porous structure upstream of a suction port, in accordance with some embodiments.

FIG. 27 shows a container portion 140 of a surgical drape 100 with a porous structure such as screen 148 upstream of a suction port 462. The porous structure located upstream of suction port 462 may comprise any porous structure as described herein, such as one or more of a tube with holes on an outer wall, a screen, a mesh, a fabric, a grating, a plurality of apertures formed in a sheet of material, an open cell foam, a sponge a screen, a perforated tubing matrix, fabric, a sintered material, or particles held together to define channels. The mesh may comprise a fine mesh, for example. The porous structure such as screen 148 can be located upstream of suction port and coupled to an inner wall of container portion 140 to direct fluid entering container portion 140 through porous structure. The suction port can be connected to a source of suction, such as a surgical suction pump, with a tube coupled to the suction port and the source of suction. The porous structure such as screen 148 can filter particles comprising blood clots and ablated tissue, to inhibit blockage of suction port 462. In some embodiments, the porous structure comprises channels having a maximum cross-sectional size no larger than a minimum inner cross-sectional size (e.g. minimum diameter) of suction port 462, to ensure passage of clots or tissue passed by the porous structure through the suction port. The porous structure may comprise a surface area to receive surgical fluids, clots and tissue.

The container portion 140 may comprise a fluid inlet 460 to receive flowable material from a surgical procedure, such a surgical fluid comprising tissue and clots from an ablation procedure. The ablation may comprise a water jet ablation procedure performed with an ablation probe as described in in PCT Application No. PCT/US2013/028441, filed on Feb. 28, 2013, entitled "AUTOMATED IMAGE-GUIDED TISSUE RESECTION AND TREATMENT", which has been previously incorporated by reference. The fluid from the surgical probe can be coupled to the inlet with a tube, such that the ablated prostate tissue material can be collected on the porous structure and used for subsequent analysis.

In some embodiments, the receiving surface area of the porous structure comprises a surface area greater than the minimum inner cross-sectional size of the suction port in order to provide additional channels of the porous structure to pass surgical fluids when solid material such as clots and tissue have been deposited on the porous structure.

The porous structure may comprise channels extending through a thickness of the porous structure that are sized and shaped to collect tissue from the surgical procedure for subsequent analysis. The channels can be sized no larger than the approximate size of a prostate cell, for example no larger than about 5 microns (um). The channels of the porous structure may comprise a maximum cross-sectional size within a range from about 0.1 microns to about 5 microns, for example, in order to capture individual cells of the prostate. Alternatively, the channels of the porous structure may comprise a larger cross-sectional size and may comprise a maximum cross-sectional size within a range from about 5 um to about 1 mm in order to capture tissue of the prostate comprising cells and blood clots received from inlet 460.

In some embodiments, the porous structure 148 and suction port 462 are configured such that an amount of fluid 464 accumulates in the container. The porous structure can decrease the amount of fluid accumulated in the container portion 140 as compared to fluid accumulation without the porous structure. The surface area and the size of the channels of the porous structure can be configured to decrease amount of fluid that accumulates between the porous structure and the opening to the suction port on an inner side of the container when the suction port is coupled to the suction source. The amount of accumulated fluid with the porous structure on the lower end of the container can be within a range from about 0.05 cm$^3$ to about 500 cm$^3$, for example within a range from about 0.05 cm$^3$ to about 100 cm$^3$. In some embodiments the porous structure can be separated from the suction port with a gap extending in between, and the amount of fluid that accumulates between the porous structure and the opening to suction port can be within similar ranges, e.g. from about 0.05 cm$^3$ to about 100 cm$^3$.

Figure 28:
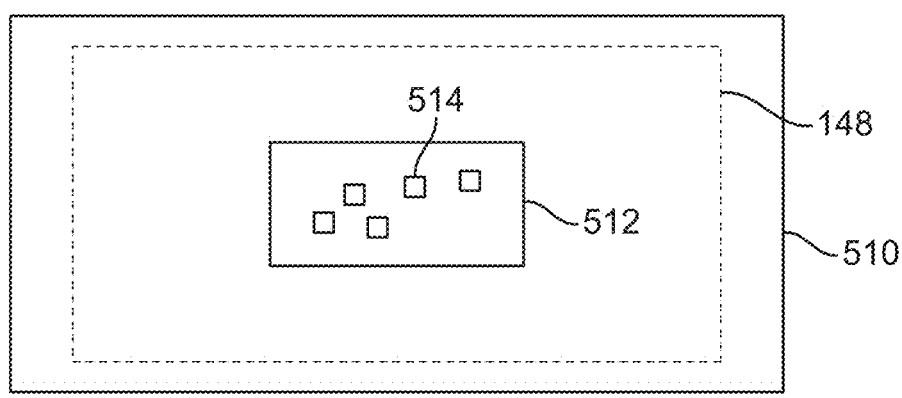
FIG. 28 shows a container with a viewing window, in which the container is sized to receive a porous structure with solid material from the patient supported thereon, in accordance with some embodiments.

FIG. 28 shows a container 510 with a viewing window 514, in which the container is sized to receive a porous structure such as screen 148 with material from the patient supported thereon. The viewing window may comprise an optically transparent material configured to allow viewing the material from the patient with a high-resolution microscope for example. The container 510 may comprise a sealed container that can be sealed with the porous structure and material of the patient placed thereon. The container may comprise a barrier material configured to inhibit release of material from the patient.

Figure 29:
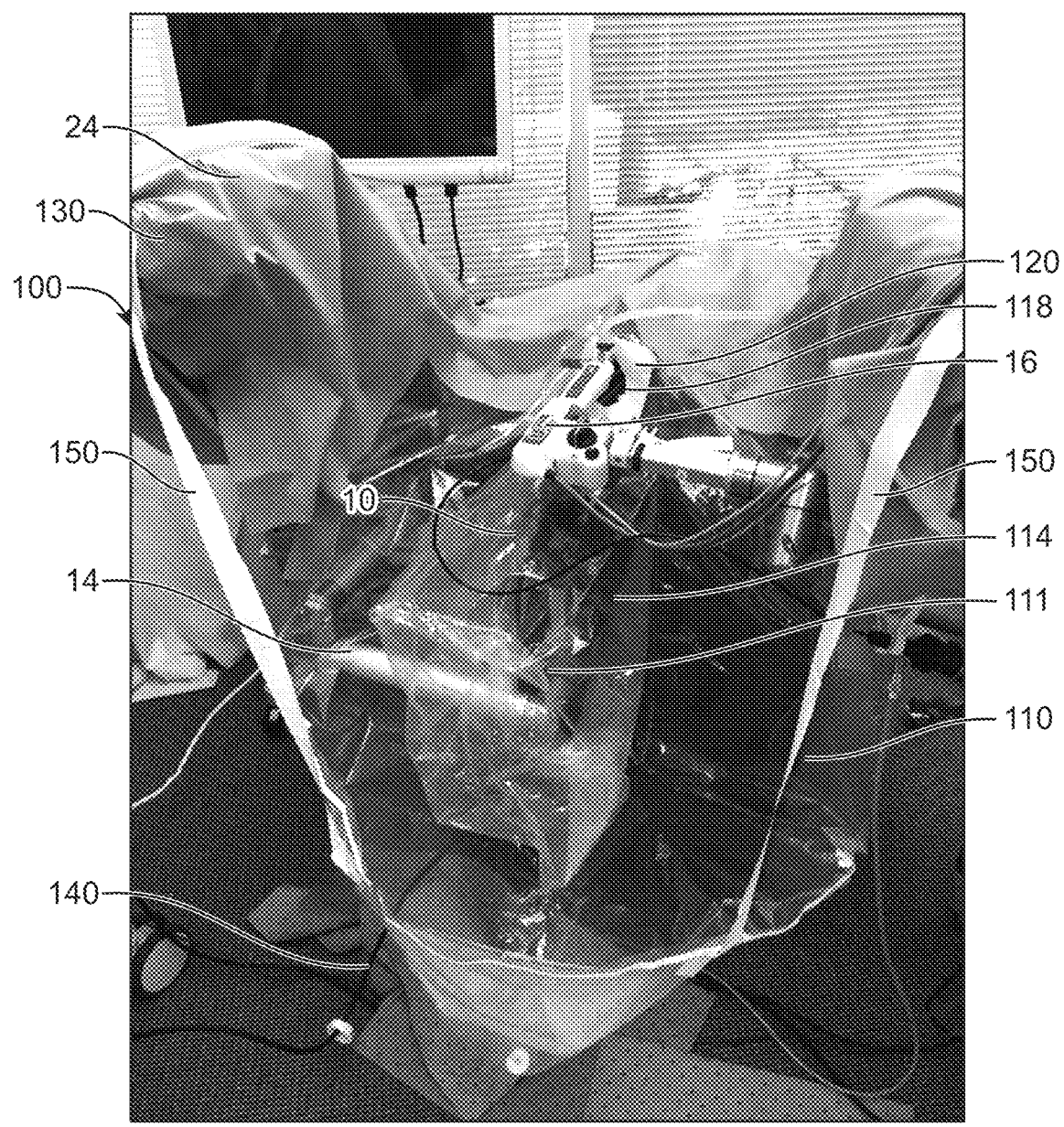
FIG. 29 shows an image of surgical drape used to conduct experimental testing, in accordance with some embodiments.

FIG. 29 shows an image of surgical drape 100 used to conduct experimental testing. The inventors conducted several experiments to determine the advantageous structures, elements and portions of the drape and other elements as described herein. The surgical drape shown in FIG. 29 includes many of the elements and structures shown and described above with reference to FIG. 1B. This testing was used to determine appropriate shapes and structures and material properties of the drape to provide the beneficial functions and structures as described herein, such as fluid management, stiffening structures and dimensions of the canopy and container, return of the canopy, and the dimensions and material properties of the porous structure, as described herein.

As one of ordinary skill in the art will appreciate in view of the present disclosure, the surgical drape comprises a sterile side that generally faces away from the patient and a non-sterile site that generally faces toward the patient, in order to provide a sterile barrier between the patient and the sterile side of the drape when placed on the patient. Alternatively or in combination, the surgical drape can be configured to cover the feet or legs of the patient, for example with the second portion comprising the torso portion as described herein extending so as to cover one or more of the feet or legs of the patient.

In some embodiments the user of the drape places a handpiece down and/or resectoscope on top of the drape on the patient's stomach, and the drape may comprise a fastener, such as a strap or Velcro or tether or tape portion configured to allow the user to place the handpiece at locations away from or on the patient's stomach. Alternatively or in combination, the patient drape may comprise an adhesive material to adhesively couple to the handpiece and/or resectoscope to limit movement of the surgical instrument. The adhesive can be covered with a peel or other material, such that the adhesive material is not exposed until the peel has been removed from the surface of the adhesive by the user such as a physician or attendant. Securing the handpiece and/or resectoscope on the drape above the stomach can inhibit instruments from sliding down into the fluid container as described herein, which would be less than ideal because the container may contain fluids and/or wrappers/gauze from earlier in the surgical procedure.

In some embodiments, the surgical drape comprises fasteners such as one or more of tape or Velcro section on one or more sides of the patient's legs for wire and cable and tubing management, which can be used to bundle these together.

In some embodiments, the surgical drape as described herein comprises a packaging enclosure to store the surgical drape or portion thereof when the surgical drape comprises an initial compact configuration prior to be expanded to the extended configuration, for example in its original state prior to use. The packaging portion may comprise an extension of the surgical drape configured to cover the drape in a compact configuration, for example with a lower non-sterile side of a portion of the drape folded so as to be exposed to a non-sterile exterior environment. An internal sterile side of the folded portion of the drape corresponding to the upper sterile side of the drape can be folded so as to a remainder of the drape, when the drape comprises the compact configuration prior to expansion to the extended configuration as described herein.

Although reference is made to alternatives in the present disclosure, one or ordinary skill in the art will recognize that these alternatives can be combined in accordance with the teachings of the present disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus comprising:
a surgical drape for covering a patient;
a transrectal device;
a surgical arm coupled to the transrectal device;
a canopy portion sized and shaped to at least partially cover a proximal portion of the transrectal device, the canopy portion configured to permit a user to manipulate the transrectal device through the canopy portion; and
a torso portion coupled to the canopy portion, the torso portion sized and shaped to cover at least a portion of a torso of the patient;
wherein the canopy portion is configured to allow manipulation of the transrectal device through the canopy portion, to cover at least the surgical arm and the proximal portion of the transrectal device such that the canopy portion collectively moves with the surgical arm and the proximal portion of the transrectal device, and to permit the user to manipulate the surgical arm that supports the transrectal device through the canopy portion;
wherein the proximal portion of the transrectal device is mounted on the surgical arm and the canopy portion is configured to cover at least a portion of the surgical arm and the proximal portion of the transrectal device when the distal portion of the transrectal device has been inserted into the patient; and
wherein the canopy portion is configured to permit the user to move the transrectal device by holding and moving the proximal portion of the transrectal device through the canopy portion with the canopy portion disposed between a hand of the user and the transrectal device and wherein the canopy portion is configured to move with the proximal portion.

2. The surgical drape of claim 1, wherein the canopy portion comprises a full volume in a fully extended configuration and is configured to collapse to less than the full volume in a free-standing configuration.

3. The surgical drape of claim 1, wherein the canopy portion is configured to collapse to less than its full volume when the canopy portion is covering the proximal portion of the transrectal device.

4. The surgical drape of claim 1, wherein a second portion comprising the torso portion comprises a weakened material extending along angle or an offset to a midline of the second portion to assist removal of the surgical drape by allowing the second portion to separate along the weakened material.

5. The surgical drape of claim 4, further comprising a second weakened material extending in a second direction transverse to the midline in order to facilitate removal of the surgical drape around a base of a traction device coupled to the patient with a catheter extending along a urethra of the patient.

6. The surgical drape of claim 4, wherein the second portion comprises perforations extending along an angle or an offset to midline to the second portion to assist removal of the surgical drape.

7. The surgical drape of claim 6, wherein the second portion further comprises a material disposed on top and/or below the perforations, wherein said material is impervious to fluids.

8. The surgical drape of claim 7, wherein said material comprises a tape covering the perforations from below and/or above the perforations.

9. The surgical drape of claim 8, wherein the tape comprises a first tape layer on top of the perforations and a second tape layer below the perforations such that the perforations are sandwiched between the first and second tape layers.

10. The surgical drape of claim 6, further comprising a sliding mechanism configured to slide along the perforation to open the perforations.

11. The surgical drape of claim 1, further comprising a container coupled to the torso portion and the canopy portion to receive fluid from the canopy portion.

12. The surgical drape of claim 11, wherein the canopy portion comprises an inverted portion to direct surgical fluids toward the container.

13. The surgical drape of claim 11, wherein the canopy portion is designed such that fluid flows downward toward the container when the canopy portion is in an inverted configuration.

14. The surgical drape of claim 13, wherein the inverted configuration prevents the fluid from accumulating or pooling on the canopy portion.

15. The surgical drape of claim 13, wherein the inverted configuration comprises one or more sloping surfaces that aid the fluid to flow downward toward the container.

16. The surgical drape of claim 1, wherein the canopy portion and the torso portion are detachably coupled to each other.

17. The surgical drape of claim 1, wherein a first portion comprising the canopy portion comprises a sheet of material comprising joined edges.

18. The surgical drape of claim 1, wherein the canopy portion is integrally formed with the torso portion from a single piece of material.

19. The surgical drape of claim 1, wherein the canopy portion comprises a separate sheet of material that is attachable to the torso portion.

20. The surgical drape of claim 1, wherein the canopy portion and the torso portion are formed together as one piece.

21. The surgical drape of claim 1, wherein the canopy portion and the torso portion are joined together as one piece.

22. The surgical drape of claim 1, wherein the canopy portion is coupled to a cut-out formed in the torso portion.

23. The surgical drape of claim 1, wherein one or more of the torso portion, the canopy portion or a container portion comprises thermoformed material shaped with a mold to define a shape of the one or more of the torso portion, the canopy portion or the container portion.

24. The surgical drape of claim 23, and wherein the canopy portion and the torso portion have been formed from a single sheet of thermoformed material.

25. The surgical drape of claim 24, wherein the canopy portion disposed between the proximal portion of the transrectal device and the hand of the user is configured to move from a first position to a second position when the proximal portion of the transrectal device moves from a first position to a second position and wherein the canopy portion is configured to return at least partially from the second position toward the first position when the hand of the user releases the proximal portion.

26. The surgical drape of claim 25, wherein a return of the canopy portion toward the first position allows the user to hold the proximal portion of the transrectal device and move the proximal portion of the transrectal device from the second position to a third position.

27. The surgical drape of claim 1, wherein the canopy portion is sized and shaped to at least partially cover a surgical arm coupled to the transrectal device.

28. The surgical drape of claim 1, wherein the surgical drape comprises a volume within a range from about 100 $cm^3$ to about 4,000 $cm^3$ in a compact configuration when stored in a compact configuration within a sterile storage container and wherein the canopy portion comprises a volume within a range from about 750 $cm^3$ to about 70,000 $cm^3$ when the surgical drape comprises an expanded deployed configuration.

29. The surgical drape of claim 28, wherein the container portion comprises a volume within a range from about 1000 $cm^3$ to about 40,000 $cm^3$ in the expanded deployed configuration.

* * * * *